United States Patent
Whyard

(10) Patent No.: US 10,039,287 B2
(45) Date of Patent: Aug. 7, 2018

(54) BIOLOGICAL CONTROL OF INSECTS

(71) Applicant: UNIVERSITY OF MANITOBA, Winnipeg (CA)

(72) Inventor: Steve Whyard, Winnipeg (CA)

(*) Notice: Subject to any disclaimer, the term of this patent is extended or adjusted under 35 U.S.C. 154(b) by 0 days.

(21) Appl. No.: 15/022,759

(22) PCT Filed: Sep. 18, 2014

(86) PCT No.: PCT/IB2014/064643
§ 371 (c)(1),
(2) Date: Mar. 17, 2016

(87) PCT Pub. No.: WO2015/040574
PCT Pub. Date: Mar. 26, 2015

(65) Prior Publication Data
US 2016/0227787 A1    Aug. 11, 2016

Related U.S. Application Data

(60) Provisional application No. 61/880,498, filed on Sep. 20, 2013.

(51) Int. Cl.
*C07H 21/04* (2006.01)
*A01N 63/00* (2006.01)
*C12N 15/113* (2010.01)
*A01K 67/033* (2006.01)

(52) U.S. Cl.
CPC .......... *A01N 63/00* (2013.01); *A01K 67/0333* (2013.01); *C12N 15/113* (2013.01); *A01K 2207/05* (2013.01); *A01K 2227/706* (2013.01); *C12N 2310/14* (2013.01); *C12N 2330/50* (2013.01)

(58) Field of Classification Search
CPC ..................................................... A01N 63/00
See application file for complete search history.

(56) References Cited

U.S. PATENT DOCUMENTS

| | | |
|---|---|---|
| 2013/0058890 A1 | 3/2013 | Raemaekers et al. |
| 2013/0137747 A1 | 5/2013 | Zhu et al. |
| 2013/0237586 A1 | 9/2013 | Whyard et al. |

OTHER PUBLICATIONS

Nene et al. Science Jun. 22, 2007, vol. 316L 1718-1724.*
Alphey et al., "Sterile-Insect Methods for Control of Mosquito-Borne Diseases: An Analysis," *Vector Borne Zoonotic Dis.*, 2010;10: 295-311.
Baum et al., "Control of coleopteran insects through RNA interference,"*Nat. Biotechnol.*, Nov. 4, 2007;25: 1322-1326.
Bloem et al., "SIT for codling moth eradication in British Columbia, Canada. In Area-Wide Control of Insect Pests: Integrating the Sterile Insect and Related Nuclear and Other Techniques," *Proceed-* *ings, FAO/IAEA Symposium, Penang, Malaysia* Universiti Sains Malaysia, Penang, Malaysia, 1999.
Diatchenko et al., "Suppression subtractive hybridization: a method for generating differentially regulated or tissue-specific cDNA probes and libraries," *Proc Natl Acad Sci USA*, Jun. 11, 1996; 93(12): 6025-6030.
Franz et al., "Improved stability of genetic sex-separation strains for the Mediterranean fruit fly *Ceratitis capitate,*" *Genome*, 1994; 37(1): 72-82.
Gempe and Beye, "Function and evolution of sex determination mechanisms, genes and pathways in insects," *Bioessays*, 2010; 33:52-60.
Helsinki et al., "Mating competitiveness of male *Anopheles arabiensis* mosquitoes irradiated with a partially or full sterilizing dose in small and large laboratory cages," *J. Med. Entomol.*, 2008; 45(4):698-705.
Hendrichs et al., "Increased effectiveness and applicability of the sterile insect technique through male-only release for control of Mediterranean fruit-flies during fruiting seasons," *J. Appl. Entomol.*, Jan. 12, 1995; 119: 371-377.
Holbrook et al., "Mating competitiveness of unirradiated and irradiated Mediterranean fruit flies," *J. Econ. Entomol.*, 1970; 63(4):1175-1176.
International Search Report and Written Opinion for PCT/IB2014/064643, issued by the Canadian Patent Office as the International Search Authority, 14 pgs., 2014.
International Preliminary Report on Patentability for PCT/IB2014/064643, issued by the International Bureau of WIPO, 9 pgs., 2013.
Jacque et al., "Modulation of HIV-1 replication by RNA interference," *Nature*, Jul. 25, 2002;418(6896):435-438.
Chapter 1, Klassen et al., "Overview of the Joint FAO/IAEA Division's Involvement in Fruit Fly Sterile Insect Technique Programs," in *Overview of Joint FAO/IAEA Involvement in SIT.* Calikins et al. (Ed.) CRC Press, Inc: Boca Raton, Florida; 1994, Cover page, publisher's page and pp. 3-26.
Knipling, E.F., "Sterile-male method of population control," *Science.*, Oct. 9, 1959;130(3380): 902-904.
Knipling, E.F., "The Eradication of the Screw-Worm Fly," *Sci. Am.*, Oct. 1, 1960; 203(4):54-61.
Livak and Schmittgen, "Analysis of Relative Gene Expression Data Using Real-Time Quantitative PCR and the 2-$^{\Delta\Delta C}$T Method," *Methods*, 2001;25:402-408.
Lofgren et al., "Release of chemosterilized males for the control of Anopheles albimanus in El Salvador. III. Field methods and population control," *Am J Trop Med Hyg.*, Mar. 1974; 23(2): 288-297.
Mayer et al., "Mating competitiveness of irradiated flies for screwworm fly eradication campaigns," *Prev. Vet. Med.*, Jul. 17, 1998; 36(1): 1-9.
Robinson, A.S., "Genetic sexing strains in medfly, *Ceratitis capitata*, sterile insect technique programmes," *Genetica*, Sep. 2002; 116:5-13.

(Continued)

*Primary Examiner* — Kimberly Chong
(74) *Attorney, Agent, or Firm* — Mueting, Raasch & Gebhardt, P.A.

(57) ABSTRACT

Provided herein are modified insects having decreased expression of a testis-specific coding region compared to a control insect. In one embodiment, the modified insect includes the characteristic of reduced fertility, reduced fecundity, or a combination thereof, when compared to the control insect. Optionally and preferably, the competiveness of the modified insect is not significantly reduced compared to the control insect. Also included herein are methods for making a modified insect, and methods for using the modified insects, including making populations of modified insects and use of the modified insects in sterile insect technique for biological control.

14 Claims, 14 Drawing Sheets

(56) References Cited

OTHER PUBLICATIONS

Saccone et al., "Sex determination in flies, fruitflies and butterflies," *Genetica*, 2002;116:15-23.
Salvemini et al., "Genomic organization and splicing evolution of the doublesex gene, a *Drosphila* regulator of sexual differentiation, in the dengue and yellow fever mosquito *Aedes aegypti*," *BMC Evol Biol*, 2011;11(41): 19 pgs.
Sambrook et al., *Molecular Cloning: A Laboratory Manual, Books 1-3*, Cold Spring Harbor Laboratory Press, Cold Spring Harbor, NY, 1989; title page, publisher's page and table of contents only (30) pgs.
Shukla et al., "Sex determination in beetles: Production of all male progeny by Parental RNAi knockdown of transformer," *Scientific Reports*, Aug. 24, 2012; 2(602):2-9.
Sui et al., "A DNA vector-based RNAi technology to suppress gene expression in mammalian cells," *PNAS*, Apr. 16, 2002; 99(8):5515-5520.
Thailayil et al., "Spermless mailes eleicit large-scale female responses to mating in the malaria mosquito *Anopheles gambiae*," *Proc Natl Acad Sci USA*, Aug. 16, 2011;108(33):13677-13681.
Vreysen et al., "*Glossina austeni* (Diptera: Glossinidae) eradicated on the island of Unguja, Zanzibar, using the sterile insect technique," *J. Econ. Entomol.*, Feb. 1, 2000; 93: 123-135.
Whyard et al., "Ingested double-stranded RNAs can act as species-limited insecticides," *Insect Biochem. Mol. Biol.*, 2009;39: 824-832.

* cited by examiner

Fig. 1-A

Vectorbase Accession Number: AAEL001684
GenBank Accession Number: AaeL_AAEL001684
SEQ ID NO:227
ATGTCGATACCGAACCCTGCGGGACAGATAGACGGCGCACTGGCTGCGCCCAAGTACGGT
ACGCTCATTCCGAACCGGGTATTCGTCGGTGGTATCAGTGGCGACACGACGGAAGCGGAA
CTGTGCCGGTTATTCAGCTCGTACGGCAACGTCAAGTCAACGAAAATCATCGTAGATCGG
GCGGGCGTCAGCAAAGGCTACGGATTCGTAACGTTCGAAACCGAACACGAGGCACAAAGA
CTGCAGAGCGATGGAGACTGTATCGTGCTGAGGGACCGTAAGCTAAACATAGCACCAGCG
ATTAAGAAGCAAGTAAGTTGGCACCATACAATCTGCGCGACGAACGGTGCCGTGTACTAC
GCAGCCACACCCCCGACGCCGACGATCAACAACATCCCCATCGAGCAGTTTGCGACGGCA
GTCTATCCGCCCGGTGTGCCAACAATCTATCCTCCGACGATGACGCCCTACCAGCCGTTC
TACCAGTACTACAGCGTGCCAATGAATGTACCGACAATTTGGCCTCAGAACTATCAAGGT
ATGTAA Vectorbase Accession number: AAEL002275
GenBank Accession Number: AaeL_AAEL002275
SEQ ID NO:228
ATGTCTTTGGATTTGACCCTGGACGCGGGCGAGGAGATGCGTTTCCTGAACAAAGTTAGT
CGTTTGGTGCGGCGTTTGGAGAAGAAAACCCATTTCACGCACCGGGAGTTGGAGGTTTGT
CTGTTGATCTACTACAAACTGACCAAGGATGAGGAGGACAACAAGGGGCATGTTTCCCGG
CATCAGTTGGACGTCCTGTTTGATAGCGTTTTCGGGATATCTGATAGCGAAACTGTTGGA
AGGATTTGTACGGCGCTGGACAAAAGTGTCACGACCTTTATGAGTATGGAATCGTGGGTC
AAAATGTTGTCGTTGTTCTTGAAAGGAACATTCGACGAGAAGATCGAGCACTGTTTCCGA
GCTTATGATATCGGCGGAGAAGAGTTACTTCGGAGAGAACACATGATGATATTGTTGCGG
AGTTGTTTCATCAAGCACCAAGAAGAGGAAGTCGAAGAATCGGTTAAGGACATGGTCGAA
ATTCTTATCCGTCGAATGGACGTTGATCGAGATGGAGCCATTTCCTTGGATGACTTCCGA
CAATCCGTTCACAAGTCACCAGAACTTCTAGAGTGCTTCGGCCAGGCACTTCCAGATCGG
GCCCATGTATACGCTTTCTCTAAAACCTTCCTCGACCAGTCGGCTGAGTTCTAA Vectorbase Accession Number:AAEL004231
GenBank Accession Number: AaeL_AAEL004231
SEQ ID NO:229
ATGCAACATTTCTATTTCAAGGCACTCTGTATGGGTCCCAAAAAAGCCAAAGGAAGTACG
GTCATCGATGGGGTGGACACATCCAGTATGTCCCGCGAACAGCTAGAACAGTTTGCGCTC
CGGCTTCGCAACGAGATGGAACGGGAACGCGAGGAGCGAAACTTCTTCCAGCTGGAGCGG
GACAAACTGCGCACGTTCTGGGAAATCACGCGCAAACAGCTCGAGGAAGCGAAAGCCGTG
ATACGCAACAAAGAACGTGACGTAGAGGTTGCCCAAGAACTTGCCGACCAGGACACGAAA
AATGTGATGCAGGAGATGAAGCATCTGCAGTACGAGCATCAGTCGCACATCGGAGAGCTG
AAAGCGGAAATGATGACACAGCTGAAGATGGCTCAGGAAGATCACTCGCTACAGGAACGA
GAACTTCTCAACGACAAACGTGACCTGCGACGGTTACTGCGAGAGAAGGAGGAAAACTCT
GAACTAGAAGTACAGCAGCTTAAACTAAAGCACAGCGAACTGCTGAGCCAAGAACGCGGA
AAGTTTAAAGAGGAAATTGACGCAATGACCAAATTGTTTGAACAGCGCCTACAGAGCTAT
AAAGAAGAAGCTGAAGTGCGCCACGAAATGGAATTGTCAGAGGTCGAAGAACGAAAGAAC
GGCCAAATTTCCGAACTGATCCAAACCAATGAAAACGCCTACAAGGAAATGAAGGGTTAC
TACAACGACATTACCCTGAACAACTTGGCACTCATCAACAGTATGAAAGAACAGATGGAA
GAGTTGCGTATTCAATCAGACAAGGACCTGAAGAACCATTCGGAAGTGATGGCGGAGAAC
AGAAGACTCGTTGAACCGTTGAAGCAGTCCCAATCAGAGTTGGTCGAGTTGCGCAAAAAG

Fig. 1-B

```
TTGCAATACTACGATCGCGACAAGGCTACGCTCAATCGAGTGAAAACTCGGCTCGCTTCG
ACGCAGAAACAGCTCAGTAGCTTGAAGCTCGAATCGGACGTCCTGCAGATGCGCTGCGAG
AAGCTGGTCGAAGAACGCGATCAGCTGAAGAATATGTTCGAGAAGTCTATACTGGAGCTG
CAACAGAAGTCAGGTTTGAAAAATTCCTTATTGGAGCGAAAACTAGAATACATCGAGAAG
CAAACGGAACAACGGGAAGCCATTTTAGGGGAGGTGCTATCGCTTGCCGGAATCGAACCG
CAGTCGTTGAGTATCCGAATTGAAAAACTTCTGGTGCAGAAAAACGACAAAATCCAAGAC
CTACGCTACGAACTGGCCCGCGTTAGCAAAATGTACGACGACTTGCTGTCGATGATGGAG
GCTAAATTGGCAAAGTATGGCATAACTTTAAAGGATCTGGAGCTGAGCAGCATGAGATTG
GAAAAGTGAATTTGGCACAAGAGAAAACTTTTCGACTTTAAATAAGTTGTTGCACAGGTT
TGCAAATAAACTTTTGGACACAGT
```

Vectorbase Accession Number:AAEL004471
GenBank Accession Number: AaeL_AAEL004471
SEQ ID NO:230

```
ATGGCCGCCTATCTTAACCGTACCCTGTCGATGGTGACGGGCTCGAATGGGTCGGCCTCG
ACGGGATACGACACGGCGGCACTGATCGATGCGAACACATCGTCGCCGCGGGTCTGCAC
ACGGCCACTGGTGGCGGGGCTGCCGGCCACAACGACGTCTCGCCGTTGCAGATTTTCGTC
CGCGCCAAGAAGAAGATCAACGACATCTTCGGCGAGATCGAGGACTATGTGGTGGAGACA
ACCGGATTCATCGATGCCCTCCCGACGATGGTGGAAATCGTGGACAAAGCCGAGTCGGAG
CTATTCCGGAGCTATGTGCTGAAAGTGTCCGGCATCCGGGAGGTGCTCGCCCGTGACCAC
ATGAAGGTGGCCTTCTTTGGGCGCACCTCCAACGGGAAAAGTTCAGTGATCAACGCTATG
CTGCGGGACAAAATCCTACCGAGTGGTATCGGCCACACCACCCATTGCTTCTGCCAGGTG
GAGGGCATCGATGGCGACGAGGCATACCTAGTCAAGGAAGGTTGTGATGAGAAGCTGAAT
GTAACGTCGATTAAACAACTTGCCAATGCGCTATGCCAGGATAAACTCTCGGAAAGCTCA
TTGATCAGGATATTCTGGCCACGTAAACGATGTAACTTGCTAAGGGATGATGTAGTTTTC
GTTGATTCGCCCGGAGTCGATGTGTCACCTAATTTGAACGATTGGATAGACAATTTCTGC
TTAAATGCTGACGTTTTCGTGTTGGTTCTCAATGCTGAATCCACTATGACCTTGGCGGAA
AAACACTTCTTCCACGAAGTCTCAACCCGGCTTTCGAAACCGAACATTTTTGTGCTGAAC
AACCGTTGGGATGCATCGGCCTCAGAGCCGGAGTTCCAGGAATCGGTCAAAGCACAACAC
CAGGAACGATGCGTCGATTTCCTCGTGAAGGAGTTGAAGGTTGCATCCGGAAAGGAGGCA
GAGGAACGCGTCTTCTTCGTGTCAGCGCGTGAAACACTGCAGGCCCGATTGAAGGAAGCC
GAAGGTCTGCCAGCGATTGCCGGCGCTTTGGCTGATGGTTTCCAGAACCGGTACTTTGAG
TTCCAGGACTTCGAACGGAAGTTCGAGGAATGCATCTCGAAAAGTGCAGTCAGAACCAAA
TTTGAACAGCACAGCTCTCGCGGCAAGAGCATCTCAACGGAGATGCGCATGATGCTGGAC
AACATCTTCGACCGGGCGAATGTCCTGCGCAATCAGAAGCTGGAACAGAAGAAGAAACTG
ACTGATCGGATCGCAAATACCGAAACACAACTGATGCAAGTGACACGAGAGATGAAAATG
AAGATCCACAACATGGTCGAGGAAGTCGAGCAAAAAGTGGCCAAGGCACTGAACGAGGAA
ATTTGGCGACTAAACGTGCTGGTGGATGAGTTCAACCTGCCTTTCCACACGGATCCATTG
GTTCTGAACGTTTACAAAAAAGAAATCAACGCCCACGTGGAAAGTGGCCTTGGTTCGAAT
CTGAGGGCGCGACTTAGCACAGCTTTAGCCATGAACGTCGAAACAGCGCAAAGGGAAATG
ACCGACCGCATGACTGCGCTGATCCCGTCGGAAAAGATCATCACCCACACGCATCACGTC
GTTGCGCGGAATCAACCGTTCGAGATGCTGTACACGCTGAACTGTCAAAACCTATGTTCC
GATTTCCAAGAGGATCTGAATTTCCGCTTCTCCTGGGGAATCACTGCGTTCATAGCGAGG
TTTAATGGCAAAATGCGAGCGAACAGCAAGAAGCAATTTCGCACAATAGGCAAAGTAGC
AATATGAATGTATCGCAAGTAATGTCTCCTACTTCACCGATGTGTCTTATGCCGGATAAC
GAACTGATCACAGAAGAGCAGCTGTCGGTGATATCGAAGGTGGCGATAGCTTCGATCGGA
```

Fig. 1-C

```
TCCCAGGGCACCCTGGGGCTTCTGGTGGCCGGTGTGCTCCTGAAAACAATTGGCTGGCGA
GTGATTGTGGGTGCCGGCATCCTGTATGGCAGCGTGTATCTCTACGAGCGCCTGTCCTGG
ACCAACGCCGCCAAAGAGAAGAATTTCAAAAACCAGTATGTGCAGCACGCCACACGGAAG
CTGAAGTTGATTGTCGATCTCACTTCGGCCAACTGCAGCCACCAGGTGCAACAGGAGCTG
TCCAGCACCTTCGCCCGATTGTGTCGCGTTGTCGATACCGCTACCACAGAGATGAACACT
GAACTGAAGGACATCGAAACCTCCCTGGCCGTGATCGAGGCCAACCAGAAGCAAATCAAG
GTGCTCAGCAATAAGGCCAACTTCATCCAGCGCGAGCTGGAAATCTTCGACAGCAACTAT
ATCAAGGAGAACTAAGTTGAACCCTTCTGAAGAGGGTAGCAAGAGTTAATGTTTAATATA
TTGTATTCTCGCCAGGAGACAGCGTCACTCAAACCGGTATCGAAACCAAACAAAGTTTGT
AGCTTGGATGGATGTGACAGAAAGTTTAGTTACATAGAACCTACGTTCCTTGTTCACACT
TTTTACCTGATTCGATACTTTGCAAACATTGCTATATTTATATTTTTAAATGTTATATGC
TTTAGTTTCCAATTTTGATTAGTTGCTGTGCACCAACATATTTGGTTGGATAGTTATCGT
CACCTCCAAAGCAAGAATCTACACACCAACCGAATATGTACTACAAAGATTATTGATGCA
AGTGAGTGAAACTTACTTAGAGAATACGCTAATGAATCCCTAACAAAATATTTCAATGTA
ACTGTGTATAATATATCCTAAGACTTAGTACTGTAGGAGAGGTCGTTTTCTTGTACAGGT
ATTACCGTACAGACTAAAGGCAGTTAGATATTTCTGTTAACGATAGATGAGGGCTGTTG
TAAAAATAAATTAAATCTATCGAAAAAGCTAAAATCGGAAACTAGACCAAGCGTTGATTG
CAGAAGCTAGACCGCAAACCGTTAGATAAATTGGGTATCCCTGTTTTGTACTGTTGTACC
ACGTTGACTCAATCCTTGATTTACTTCGATCAAATTGTACCGAAAATTATAACTGAAAAA
TTGAACCCTGAAATAAAGTATTTCCAACTTC

Vectorbase Accession Number:AAEL004939
GenBank Accession Number: AaeL_AAEL004939
SEQ ID NO:231
ATGCGTGAAATCGTTACTCTTCATCTTGGACAATGTGGCAACAAAATCGCCCAGACATTC
TGGGAAACTATCTGCGAGGAGCACTGCCTAAACGAGCGCGGCCAGTTTATAGGGAAACAC
TTTCTGCCACTTCAACGGATCAACGTGTACTTTGAGGAGGCTCCCTGCTGCAATTTCGTA
CCAAGGGCAATCTTTGCCGACCTGGAACCGGGTGCGATGGTCGGTTTGAAATGCAGCCGC
TTCGGGCAGCTCTTTTCCCCGGAAAGCATGGTCAACGGGATGCTCGGAGCTGGGAATAAC
TGGGCTCGAGGCTACCACACGGAAGGCGCCGAAATGTTGGACAGGATCATGAATGTGGCT
CGGAAAATGGTGGAAGGTTGTGATTGTTTCCAGGGGTTCCAAATGGTACATTCGATTGGC
GGCGGAACCGGATCCGGATTGGGAACGCTGATGATGGAGAACATGAAAGATGAATTTCCT
CGGAAGATACTCAACACTTTCAGTGTGATCCCGTCCGAAAAGGTTTCGGAGGTCGTTGTA
GAACCATACAATGCAGTTTTCGCTTTAAACTCCATGACGGATTGCAGTGATGAAACGTTC
TGCCTGGATAACGAAGCCCTGTACAACATAAATATGACAACGCTTCGAGTCGACAAACCC
ACCATAGACGATTTGAATCACCTTATTTCGATGGCAATGTCTGGCATTACCTGCAGTTTC
CGGTATCCTGGGCAGCTGAACTCGGATCTTCGAAAACTTCTGACCAACATGGTACCCTAT
AGGAAACTTCACTTTTTCGTACCGGGTATTGCGCCGCTAACATCGAAGGAAAGTCAATGC
TACAGAAGTCTCTCCGTTTCGGAGTTAGTCTATCAAATTTTTGATGAACAAAACCTCATG
GCAGCTTGCTCGCCATCCAGAGGAAAATATCTAACGGCTGCTGCCCTCTTCCGGGGACGA
GTATCTACCAGAAATGTGGAAGAACAAATCGCCAACGTAAGGCAGAAAAATCACGGTACC
TTCTCGCATTGGATCCCAAATAATGTCAAATCAGCCATTTGTGACATTCCGCCTGCCGGA
ATGAAGATGTCTGCAACATTTATAGCGAACACCACCGCCATCACTCAGTTGTTTCAACGG
TTGCTGAATCAGTTTGGAACCATGTATCGGAGGAAAGCTTTCCTTCACTGGTACACGGGA
GAGGGAATGGAAGAAAGGAGTTTGTCGACGCCGAGCAAAGCTTGAGGGAGCTGATCAAG
GAGTACGAAAGTCAAGAAGAAGCAGGCCGGCAGGATCTACGAAGGGTTCGATGCTTGAT
GACGAATAA
```

Fig. 1-D

Vectorbase Accession Number:AAEL005010
GenBank Accession Number: AaeL_AAEL005010
SEQ ID NO:232
ATGTCCACCAAGACTGACACCGGGAGCAAGAAGGCCGTCGAGTCAAACGGTGGAAGTGGA
TTGTCCGTATTCGGGTCGAAGTCCTCCATTACACGGGCGCTGAATCTGCATGGATACCAC
ATGGGCATAAAGATCGGGAAGGGATCGTTTTCGTCGGTCCGGTTAGCCAAATACATCAGC
AAGAATCAGAACGTCCAAACGCTGGCCTGTAAGGTGATCGACGTCCGCAAGGGGACTGAA
GAATTCATCAAGAAGTTCTTTCCCCGGGAGCTCAGCGTGTTGATGAAGATCCGCCATCCA
AACATCATCAAAATCCACAGCATTCTGAAGCGGGAACGGATGGTGTTCATCTTTATGGAT
TACGCCGAAGGTGGAGACCTGCTGAAGTACATCAACAAGAACGGAATCATCAAGGAGACC
CAAGCCAAGCGATGGTTTGCGCAGTTGGTCAGTGCCCTGCAATATCTGCACTCGATCGAC
ATCGCCCATCGGGATCTGAAGTGCGAGAACATCCTTATTTCGAAGAAGGGAACAGTCCTA
CTCGCTGACTTCGGCTTCGCCAGGGTCTGCGGCGAAGAGAACGGGACCTTTTCGAACACC
TACTGCGGTTCGGCAGCCTACGCAGCTCCGGAAGTGATCCTCGGTAAACCCTACAATCCG
ATGCGGGCTGACGTTTGGTCACTCGGAATCATTCTGTTCGTGATGCTCAACGCTGCGATG
CCTTTTGACGATCGGAATCTGAAGAAGCTGGTCGAGGACCATTGGAGTCGAAACTTCGGG
TTCGACCAGACCGTGGACAAACAGCTGAGCGTGGCTGCCAAGCGGACGGTGTTTGAGTTG
TTGAATCCGGATCCGGCGGAGAGAGTGGAGCTGGAGCAGTTGAAGGGACTGGGATGGATC
GACGAAGACTCGGGTAAGGAGAAGAAACGAAGGATGGGAGAGCTTTGCGTGAGGGGAGCG
AGTAAGGGCGGCCGAAGTGGATCGGGGACCAAGACCGGATGTAATTGTTGA Vectorbase Accession Number:AAEL005975
GenBank Accession Number: AaeL_AAEL005975
SEQ ID NO:234
ATGAAGTCCGAGCAAATGCCGCCTGCTAAACCTATCGTCTGCACTGCAATGCTGCAAATT
CGCGCTCCGGCCGGTACGGCAATAACGCGTACGCCAGCGACCCTCCAAATCCGTGCGACC
ACGCCCACAATAGTATCGCGCCAAACCGCAGCCACCAACAACACGACGGTTACCACCAAA
ACGATCCGTAGTCAAACACCGGCCGTGGTCTCGGTAGCAGCTGCTGCAGCAGCAGCGGCC
GCTGCGGCATCTGGTTCCACGGCCACTCAGGTCAAGCAAGTGACAGCAATTAGTAACAGC
AATGTAGTCGTCGCAGCCTCAACACCATCAACGGCACCTGGTCTTGTAGTGACCGGGACA
CAACCGTTGCCAGCGTTAGCACTTAGCTCTTCCGCCGTGGCCACTTTGAATAATGCTAGT
AATAGTAATAGTTCTACGAGTTTGATCAGTACAAGCATCCCTTCTACGACGACCGTAGTT
GTCAGTACGGCTCCTAGTATCAGTACTGCAATCACTAGCAGTATTACTAGTAATAATAGT
AGTGCCAGTCAGGTAACTACTGCTAGCACTAGCAGTTCTTCCACCACGGTCACCACTTCC
AGTAGTAAATCAAGTTCAGGATCAAAATCACAGGGCTCGTCGGCGGGCACGAAAAAGAAA
GCAAATGCTAGTGCTGCCGTGAGTTCTGTTGATCCTAACGATCCGACAGCAGCTAAGAAA
GCAGCCTCTATGCAATCCTCTTTTTATCAGCATCACGTGTCTTCCTCAATGTACGGGGAT
GATGATATCAACGACGTTGCGGCCATGGGTGGTGTCAACTTGGCGGAGGAAACCCAACGA
ATTCTCGGTTCAACGGAATTTGTGGGGACACAGATTCGATCTTGTAAAGACGAAATATTT
TTGCACATGTCGGCGCTGCAAGCGAAAATACGGGGATTGTCGCGAGGCACGGACTGGAG
GAACCGAGCAGTGAGGTCGCAGTACTAATATCCCATGCCTGCCAAGAACGACTGAAAAAC
ATCGTGGAAAGTTGGCCGTAGTTGCCGAGCATCGAATCGATATTATCAAGGTTGACCCA
CGGTACGAAGTGACGAAGGACGTACGGGGCAAATCAAGTTCCTAGAAGAGTTGGACAAG
GCGGAACAAAAGCGACACGAGGAACAGGAACGTGAAATGTTGATGCGAGCAGCCAAGTCT
CGATCAAAAACGGAAGATCCGGAGCAAGCTAAACTTAAGGCTAAGGCGAAGGAAATGCAA

Fig. 1-E

CGAGCAGAGATGGAGGAACTTCGACAGCGAGACGCTAATTTGACGGCCCTGCAAGCCATT
GGACCACGGAAAAAGCCTAAACTGGAGGAGGGAGCAACTACGACTGTTACGGTTAGTTGT
CCAGCACTTGTTTCGGTCTTCACATGTTTTTCAACTCCGTTTTTCTGTTTTTTTTAGCC
TGGTGCATCCGGCATTGGAGTGGGAGCAAGCGGGAAGACCGCCACCCCGTTGAGGCCTCG
AATCAAGAGGGTCAACTTGCGTGACATGCTCTTCTATCTGGAACAGGAGAAGGAAAGCTG
CAGAAGTCAAATGCTCTACAAGGCCTACCTCAAGTGATCGATTGTGGTGGTAAAACAGCT
AAAAATGGTGATAAAAATATGACGATCGTTCTCTGCTGAAGCCGTGAACGGCGCCCAAG
GTAAGGACCAACCACCGATCCACGCCGCCAGCGAAGGAGGTTTAAACTAGAAATCCGGTG
GCAAGTGTGTTTCAGCTTGGAAGCGCGCGAAAGAGGTTTTGGCCCAATCAAAATGCGTTT
CATGGTCAGTTCAGGTCAGATGTCAAGAGTCAGAGGAAGATTGGAGCACAGTTTGTGTAA
AAGTGAGAGCGAATCATCAGGATGTTTATGTGTATGCGTGTGTGCGTGATTTTTGAGATT
TTTTTGTAAATATTTCAATTGGCCGCTACGGTGGAATATCAGGAATCGTGCGCATGAGTG
ATGACGAGAAGGATTTGCCGGGTAGACCAGTTTGGTATGGATTCGCCGACCGAACTGTTT
TTGACGTTTTATTTAATTTGGAAAACTAACTTCGAAATCAAGTGTACAGAAAACAACACA
TTATAGGGTAAAGTGCACGAGCGAGTCTAGGTATGTAGGTAAAACAGAGAAGAAAGGAAA
AAATAGGTCTAAAATAGTGAAAACAGATTTAAAAACAATTGTGTAATTAATTTTGAGTCC
TCTAGAGCTGTGTGCTTGGCGGAACAAAAGAAAAAAAAAACTGGTCAGCCGCAAGCATTG
TTTTTGTTTGTTTATCATTTTAAGTCTATATCGATAGGAACAAAATAAAACTCAATAGAA
ATCATAAAAAAACATTAAGGAAAACAAAAATCTGAAAATTTCAACCGAAAGGATAAAAAA
TAGTTTATATATCTATTGAATCGCCGTTTTCTCGGAAACAAAAATCGATATGTTATAAAT
TATATTGACGAACAGTCAATGAGTAACAAGCTTTGTTTGTGATTATATCACT

Vectorbase Accession Number:AAEL006975
GenBank Accession Number: AaeL_AAEL006975
SEQ ID NO:235
TTTTGCCCTGCAATCGATGCGTGCCTTCCGGAATGCATATGGAGCTCTCCTGCGACGCAA
ATTTTCCACCAACATCGGAGAAAATCGGGCAGAGGTGAGTTGGTTAACCGTTTGATCCAG
TCCGAAGACTTCAACATTTCCTTGAATTTCCAGAAAGGATTGGTTCTGGGCCTGTACGAG
CAGGAAATTGAAACGGACGAGCCTCGCTTGACTCCAGTGGCCGGCCATTTCGATGCCAAA
ACGGAAGGACAGCTCGTAAATCTAATCAAAGAGTCAAATCTGAAAGGAAAAGTTGGACAA
GTCAAGGTGTTCAACAACATCGATCCGGACTTCGGTTCGGTGGCCGTTGTAGGACTCGGT
TTGGAAGGGCTCGGGTACAATGAGCTTGAACAGCTGGACGAAGGCCTCGAGAACGTTCGT
ATCGCGTCTGGTGTAGGTGCTAAGTGTCTAGCGAAGCAAGGATGTTCCCGGATTTCAGTC
GACCCAATGCAAGCGGCAGAACAAGCAGCGGAAGGAAGCGGTCTTGCCACCTGGAAGTAC
CAGGCCAATCGAATGAAGTCGGAGCGGATTCCAACGCCGAAGTTGGAGTTGTTCGATTCG
CCGGACGGAGATGCATGGACGAGAGGCTTGTTCAAAGCTGATGCGCAGAATCTAGCACGA
AGCTTATCCGATGCACCGGGAAATCAGATCACTCCGACGGCCTTTGCGCAAGCAGCTGTG
GACGCTCTTTGCCCATGTGGAGTTAGCACCGAGGTGAGAAACATGGACTGGATTGAGTCG
AAAAGCCTGGGCAGCTTCTTGGCGGTGGCCAAGAGCTCGTGTGAACCACCAATCTTCCTG
GAAATCAGCTACTGTGGAGAACACGATTCAGGACGTCCGATTATGCTGGTTGGCAAAGGA
ATTACGTTCAACAGTGGTGGTTTATGCCTGAAGGAGCCGCATGGTATGTCACAGTACCGT
GCGAGTATGTCCGGAGCGGCCTCCATCGTTGCCACCATTCGAGCCGCGGCAGCGCTTTCA
CTTCCGGTCAATCTAGTAGGCCTCATCCCACTGTGTGAGAACATGCCTTCAGGAATGGCA
TTCAAGCCGGGAGATGTCATTACTACCCTTAACGGAAAGACGGTTGCCATACACGACACC
AGCAATGCAGGACGTCTGATCATGGCCGATACGTTCATCTACGGCCAGAATACATTCAAA
CCCAAGGTGGTGATGGACGTTGCGACGCTTACGAATGGAGTAACACACGCACTGGGTGGA
GCCGCCAGTGGAGTATTCTCCAACTCGGACTTCTTGTGGAAGCAGATGCAGAAAGCCGGA

Fig. 1-F

GCCATCACCGGAGACCGTGTGTGGAGAATGCCCCTGTGGAAGTACTACACGCATAAAGTT
ACAAATTATACGAATGTGGACATCAGCAACACTGGCCAGGGCAAGGGCAGTGCCTGTTTG
GGTGCCGCATTCCTGAAAGAGTTTGTCCCGTGCGTGGACTGGATTCATCTGGACATTACC
GGCGTCGGAATGCTGAAGAAGGAGTCGGTATTCCGTACCTCGCGGAAGAGCGCATGACT
GGCCGACCAACGAGGACGCTGGTGCAGTTCTTGTACCAGATGGCATGCCCGGATGAGCAG
GTGAAGAGCCTTTCGAAGGAATCGTGCGGTGCAAATTAG

Vectorbase Accession Number:AAEL007188
GenBank Accession Number: AaeL_AAEL007188
SEQ ID NO:236
AAGGAGATTACTCGCTTGCAGCGCCAATATCTGAACATAGCCAATTCAACTGCCGCTTCC
AAAGATGTCCAGATTATGCGATGTCTGGAGAAGAAGCTCAAGTACTTGCAACGGGAAAAG
ACGGAACTCAAAACCAAGCTTAAGGTTGCGTACGCTCCCTGCCACGTTCGACGATACGAT
CGACAGGTTCAACTGGTGGAAGCCCACGTTCGCGTGCAGGATGATCTGGTCTTGAAAATG
AACGGCCTTCGAACGGAGATTCGTCACCTGGAATCGCAAATGAAGCGGCTCGATAAGGAG
AGGAAGGAGCTTCAGAAGGTTTCGCAGTCGGATTACTTCTTCTACAATCGGGTTACGAAA
GCTAAGAAACGACTAGCGACGTTGGAAGATCGATTGTATCACCTGAAGAAGCGGGAAGCT
ACGAATATCACCAAGAACCACAAACTGAAGAGCGTGATTAAGGATATGTTGGTGGATAGG
AAGCTGTTTCACCAGCATTGGAGAAGGATGATAGACACTTTGGGGTACGATAAGAAGTTT
TTGATCGATATGATTGAAAGGACGATACTGGCGTTCAACCAGGGGCAGGAGCTGTGCCAC
AAAATTGACGCCGTCAAGAATCACGCTGCAAGAGAAGAGAAGTCTCAACGACAGGAAATG
ATGGAGCTACAACGAAGAATCAATAACGACCAAAAGAATCATGAGTTTTTGCGGGTGAAA
GGCTTCCATCGGGATATGTGCGATTTGGATCCAAGAGAGGTTCGCCGAAGAAATATGATG
AAAGACGATTACGGAAGGAAGCTTGAACTGTACCAAAAAATCATCGAAAAGACAAAACTG
TTCTGTGGAGTTGAAGATATCTCGCATTTGATTGAGAAGTATCAAAAACAGGAAGACACG
TTTTTCGCTCATTTCAATTACCTGAACGAATTGAATCACCAGTATGAACAGCTGAACTGT
ATCCTCATGGATTTGTACACAAGTGTGAATGACTTGAAGGAACAGAAGCTTAGAAAAGAA
GTAAGCCAAGATCATGCTTTCAAGCAGCTGCACGAAAAGCTACTAAAGGAGACAGAGAAA
ACTCAAAAACTGCAGTCAACGGTGAAATCAAACGATTCGGAGCTCCTTGAGCAATTTGAA
GAAATTGACGAAATTTTGTTGGATGTCGGGTATGATCGATCGGACGTGAAAAACCTCCTA
GGTGAGCATCGGAAAGTGACCAAACACAACGTGAAACGATTCCTAGCGGCACTGGAAATC
AAACTGAACGAGCGTCTGGCGGTAGTCTACACTCATCTACAACCCGAGGAAGAACCAGCT
CTGAGGCGACCTGTTGCTCGCAGCTCGCAGGAAATTATTCGCATCGAAGAAGTTGTAACT
ACTCAACAATGTGCGGAATGTGCCGAGGGACAGGACGTCAATAAGTACGATGAGGCCATT
GTGCTCCCGAAGGAGATGTCTGAAATCCGGGAGGGAATGAAAGCAAAGGTTAAAGCCCCG
GATATGCAGTACCGGTTGCATAATTTAAGCAAGTGCAAGCTTCCTCGGTCGCGGATTCTG
GTCAATAAGAGATACCAATGA Vectorbase Accession Number:AAEL007434
GenBank Accession Number: AaeL_AAEL007434
SEQ ID NO:237
ATGGAATATTCGTCGACGAAAAATTTGAGTTCAGACACATTCAACAACGCTCTGTCCTCG
CCCAATGAATGGAACCGCAAAGAGGTTAAAAAACAACTTTCGGAGCGAGGTTATCTGATC
GGGCAATCCATCGGCGAGGGTTCCTACTCGAAGGTGTACTACTCGGAATACCGTAAATCA
GGCCAACAGCAGCATTTCCCGGAACGGAGAGCATGCAAAATCATCAATCGAAACAAAAGT
TCAATGGAGTATTCGCAGTTCCTTCCGAGGGAGATCAAAACGATGATAGCGCTGTCCCAT

Fig. 1-G

CCGAATATCGTTTCGGTTTATTCGGTGTTTGAATTTGGTCCTTATGTTTGCATTTTCATG
GATTATTGCCGGTGCGGAGATTTACTGCAGAGGATCCAAAGCCATGGGAAATTGTCCGAG
TCGAAAGCTAGACTACTCTTTCGGCAGTTGGCTTCCGCTGTTCAGCACATGCATTCGCGA
GGATTCTGCCATCGGGACATTAAGTGCGAAAACGTGTTGCTCTGCAGCCCATCGCATGTC
AAGCTGTCTGACTTTACGTTTGCAAAGAAGTGTCCCTGCGAGGAAGCGTCGCAAAAGCTT
AGCGCCACTTTCTGCGGCTCTGCGGCTTATGCAGCCCCGGAGATCCTCAAGGGCATTCCC
TATCATCCCAAAAGGTATGACATGTGGTCGTTAGGGTGCGTTCTGTTCATAATGGTTACC
GGAACGATGCCATTCGACGAGCGCAATATTCCGGAAACGATTGAGCGACAGGAACGGAAA
CAGTACTTCTACCCCGATGGAGTGAAACCAAACCCGACAATTATCGAACTGATTGACAGC
CTAATCGAACCGGATGTGAACGCCAGGGCAAGCATCGATCAGGTCGTGGACTGTGCGTGG
TTGCAGGAAGTGGAGTAG

Vectorbase Accession Number:AAEL010639
GenBank Accession Number: AaeL_AAEL010639
SEQ ID NO:238
ATGGCGCAAAGAAGGATTGATGAGCAAATTTTCGATGAATATGAACCAACCGAGGAGGAG
AAACATTTTGAATTTAATATTCAAAAATACAATGGCCCAAGGAATTCTCGGTTTGAACCG
CATGGTGAAGGCAGAGCAAAATTCTTTGCTGGCGGTCGATACGAGGGACAGTTTAGAAAA
GGCTTACTTCATGGGAAAGGTCGTTTGGTATTGCAAGACAGCCACAGGTACGATGGGCAT
TGGCGCAAAGGCATGAAGCATGGCATGGGTCGAATGTATTACCCAGACTGTTCGCGATAC
GAAGGAGAGTTCAGAAAAGACCAACGGCAAGGTATTGGTATTTATTACTATCCGAATGGC
GCACGTTATGATGGGAATTGGTTCAAGAACAAGCGCCACGGTGTAGGAAATTACGTTTTT
AGCCGCGGAGATGTTACCTTGAAGGGAACATGGATCGAAGGAATCGCTCGCGGTCCCGCA
GAGATCGTCTTTGAAGAGTATCGGTTCCATGGATATTGGGATGTAGACAAACCCAGAGGT
CCAGGTAGTTTCACTTTTGACGCCAAAGTTATGATCAGTGGAAAGTACTTCGTCGATGAG
AAAGAGGGATGTGATGCAAGGGAATTGGTGTGGCAACCGTTTTTGATTGAGAAATACGAC
TATTCAAAGCTACCACTGGAACCCCTTCCTTTTCCAGTAGACGAGTCGGACGTGTCAGAC
ATAAGCTCTTCTGAAGATGAAGATTGTGATTCAGAAGGGTCGTCTAACAAGGAATTACTC
ACGACGTTTGGTGTCGGCCATGTTTGA Vectorbase Accession Number:AAEL011310
GenBank Accession Number: AaeL_AAEL011310
SEQ ID NO:239
ATGGCTTCTCCAGCATCATTCCTAAGCTTAGAAAGCGATGCTAGCGAAATTCGTGGATCA
TCCATGCAGAAACCGGGCAAAGGAGAACCCGTCGACAACGATGAGTTCGAGTCGTGGGTC
AAGTCCAAGCAGCTGCTCAAACCGGATGATCAACTGGATCTAACGGAGGCCGAGCTGGGT
GAAGAGATTCCCAAGCTTCTGTCAACGGAGAATCGACATCTACCGAGGAATTTGGTGATC
TACAACTTCCATGAGGGAACATACGAACCGGTTCCACCACCGGAAACACAGTAACTCTC
TTGGAGTTTGAAGGAACTTCTCTTCATAAGGATACACCCGAGGCGAAGGAACAAATTGCG
CGCAAAGGAACTGATGAACTGAATGTCACCTTGGATAAACCACCGGAACCGAGCCCGGAA
GAGGAAGTACCGCCGCCCCATCAGAAACTCCGGACGGTGAAGATGCCGAGCGAGAGGAA
GATGAAGGAGAAGCCGATGGCGAAGCGCAGGAACAGGAAGAAGAAGTTCAGGCTGCTCCA
GAGGAGGAAGCTCCGAAGAAGAAGTTAACCAACCAGTTTAACTTTTGCGAACGCGCTGCG
CTGACTATAGCGAATCCATCCAGGTCGGTCGATACGCAAACGATTCCGCCGCCCCGGTCC
ACCTATGGATCCAGCGTGCTGCAGTGGGTTATTTACGACTCGTACTCCGAGGACTACGCA
CAGCAGCAGCGCGAAAAGGAGCGGGAAAAGGAGAAGAAGCCGATGCTGCACAAGCGTGAT

Fig. 1-H

```
GAAAAATCGCGCAAGGACGACAAGGCAAAGCAGACGGAAGAGTTCAACAAGCGCTATCTG
CAGGCCTGTCAGATTATCGAGCGGATGGTGAACCAGAACATTTACGACGAAATCGCACAA
GATTACCGCTACTGGGAGGATCCTTCGGACGAGTTCCGCGAGGAAGAGGGCACCCTGCTG
CCTCTGTGGAAGTTCTCCTACGAGAAGACCAAGAAGATGTGCGTAACTGATTTGTGCTTC
AATACGCTGTACTACGATTTGTTTGCTGTGTGCTTCGGAACGTTGGATTTCATGAAACAA
GGCAACGAAGGAGCAGTGTGTTTATTCACGATCAAAAATCCATCCTTTCCGGATTACAGA
ATAACGACCGAGAGTGGAGCCATGTGCTGCGATATTCACCCGAAGTATCCGTATCTAATT
GCGGTTGGATTGTACGACGGGAACGTGATCGTTTACAACCTACAGGTTGGCACCAAGGAG
CCGGTCTATATGTCCCATGGCGTCAATGGCAAACACTCGGAATCGGTGTGGGAACTCAAG
TGGGGACCGGACATGCAGGATGGAGAGATTAACTTCTTCACGGTTTCCGGAGACGGGCGG
GTGTTTAACTGGGTGTTGATGCAGAATAAGCTCGCTATTACGACGATTATATCGCTGTTT
TTGGACATTGACACGGTTGGGGACCGGATGGGAGCAGTCTGAAGTTGAAGGGTTGCGGC
ATGTGTATGGTGTTTCATCCCAATAACCCGGAGACGTTTTTGGTTGGAACGGAGGAGGGA
TACATTTTCAAGTGCAGTACCGCGTATAGCTCCAAATATCTGATGACCTATTATGCGCAC
TACCTTTCCGTTCACCGCATGGACTACAACAAATTCAACTCGAACATTTTCGCATCCTGC
AGCGGCGACTGGCGCGTCAAGATATGGGAGGATATGAGACCCGAACCGTTGTTCATCTTC
GACCTGGGCGCTTCGGTGGGCGATGTCAAGTGGGCTCCATACTCCAGTACGGTGTTTGCG
GCGGTCACAACCGAGGGCAAAGTGTTTGTATTCGACCTGAGCGTGAACAAGTACAAAGCG
ATTTGTGTGCAGGCGGTCGTCTCTAAGCGGAAGAACAAACTCTCTCGGATTGCCTTCAAT
CACAAGCTACCGTTCATCATCGTCGGGGATGACAAGGGCACAACAATTACGCTCAAACTG
TCGCCCAACCTGCGCATCAAGACGAAGGCACCGAAGAAAACCGTCCCGGTAGATCCACAC
TCGCTGGAAGTACAGAAACTGGACCGATTGCTGTCGCTGGTGAGGGAGCTGCCGGAAGGT
GAACTGGTGAAGGAGACGGTTTCCACCGTAGCTTCCAACTAG
```

Fig. 2-A

CG4727
SEQ ID NO:240
ATGCACAAAATAGCAGCAGCGCCGCCTCCATCGGCAACGCCCGGCGGAGG
ACTGGAGACGCCCCTGGCGGCGCCAAAATACGGCACACTAATACCCAATC
GCATCTTTGTGGGTGGCATCAGCGGCGATACCACCGAGGCTGATCTAACC
CGCGTCTTCAGCGCCTATGGCACGGTAAAGAGCACCAAAATCATCGTGGA
TCGAGCAGGTGTGAGCAAGGGCTACGGATTCGTCACCTTCGAGACGGAGC
AGGAGGCGCAAAGACTGCAAGCGGATGGTGAATGCGTGGTACTAAGAGAT
CGGAAGCTGAACATTGCACCGGCCATCAAAAAGCAGCCCAATCCTCTGCA
GTCAATTGTGGCCACAAACGGAGCCGTCTACTATACCACCACGCCGCCGG
CACCGATCAGCAATATACCCATGGATCAGTTCGCAGCCGCTGTATATCCG
CCAGCCGCTGGAGTGCCAGCCATCTACCCACCTTCAGCCATGCAATATCA
GCCATTCTATCAGTACTACAGTGTGCCAATGAATGTACCCACCATTTGGC
CTCAGAACTACCAAGAAAACCATTCGCCATTGCTGCACTCGCCGACGTCA
AACCCGCATTCGCCACACTCCCAGTCGCATCCACAATCCCCATGCTGGAG
TATCGAGGATCTGAGGGATACTTTGCCGAGGGTATAG

CG3565
SEQ ID NO:241
ATGAAGGACCTGGACGGCTCCTTGGACACTCTGGAGAATGCCCGCTTCAA
CTACGTGTATATGAAGGACATTGCTCGCCTGGCAAAGGACTCGATCTTCT
CGCATAACGAGCTGATTAGCATTGTAATGCTCTACCATAAGTTTGTGCTG
GTCAATGGGCCGAGAGCAAAGTACATGACCATTCAGCAACTCTCTGCGCT
GATGGAGCTCTTGTTTGAGATCGTGGATCGCGATCTCATTGCGACCATTG
TGTATAGAATAGCCCATACACCAGGTTCCAGGCCTCCTGACTTCTTTTCC
GACAAGCATATACACTTGGAGTCCTTTGTGCGGCTTTTCACCGTATACTT
CACCAAAGATCTTCAGCTGAAAATGGAATTCGCATTCTCGGTCTACGATA
AAAGCGATTCCAAGCAGTTGAATGGCGAGCAAGTTGGGTTCTTCGTCGGC
AAGTTCTTTGAGAGCGAGGATGAAGACGAATCCATTGAGCTGCGCTTGGA
CATGAAGGAGATGCTGTTCCTCAAATTCGACTTGGACAAGGATACCAACA
TTGGGGTTGATGAGTACTACGAGGTGGTCCGCCGACAGCCCATGCTGCTG
GAGTGCTTTGGTCGCGTGTTTCCCCCGAATCCCCAGATGGAGGTCCTTGC
GCTGTGCGCCAATGTAATGTCTTGGTTTGACGATTCGCCCAATCCCAGGA
TTATGATAAAACCAGACGGCGGCAAGGCCAGCTAG

CG14271
SEQ ID NO:242
ATGCCGCCTAAAGGGAAAAAGGGCAAAAAAGGCAAAAAATTGCCAGTGCT
CATCGATGGCGTGGACACCTCGGCGATGACTCGCGACCAGCTGGAGGCAT
TTGCTCTCCGGCTAAAAGCGGAAATGGATCGTGAGCGGGAGGAGCGTAAC
TACTTCCAGTTGGAGCGGGACAAGATTCGCACTTTCTGGGAGATCACGCG
CCAGCAGCTGGATGAGACCCGCTACGAGCTGCAGCAGAAGGACAAGGAGA
TCGAGGCCACGCAGGATCTGGCGGATATCGATACCAAGCATGTGATGCAG
CAGATGAAGCATCTGCAGTTTGAGAACCACAATAGGCTCGGTGAGGTTCG
GGCTGAGGCGATGACCCAACTAAAGCTGGCGCAGGAGCACCATGTTCTGC
AGGAAAACGAGCTTCAGCGGGACAAGCGACAGTTGCGCCGAATGCTGCGC
GAAAGAATGGAGATGAGCGAGATGCAGCTGCGCCAAATGGAGGCTCACTT
CAATGAGAAACTGCTAGAGCAGCGCATCACCTTCGAACGCGAGCGCAAGG
ACAACGAGATGCTGCACGAGGAGAAATGATCGAGCAGAAGGCCAAGCTA
GACCTTTTCTACGGCACACAAATGTTCGAGGTAGAGGAGCGAAAGAACCA
GCAGATAAAGGACCTACAGGACCACCATGACCTAGCCTTTAACGATATGA

Fig. 2-B

```
AGAACTATTACAACGATATCACGCTTAACAACCTGGCGCTAATTGGCAGC
ATGAAGGAGCAGCTAGAGCATCTGCGCAAGCAGGCCGAGAGATCCGATAG
AATCGCCGCAGACACGGCAGCTGAGAATCGGCGACTGAAGGAGCCTTTGG
AGCATGCCAATATCCAGTTGAACGAGTATCGTCGCAAACTGGAGTTCTAC
GAGCGGGATAAGCAGCAATTGAGTCGCCTCAAGACGCGCAACACTCGGCT
GGAAAAGAAGGTGAAGGGTCTCACTTGGGAGGCGGAAACTCTGATCCTGC
GCAACGACTCGCTGGTGGCAGAACGGGAGGGCCTGAAGGAGCGTTTCAAC
GACGTGATCGTCGAGCTGCAGCAGAAGACAGGACTAAAGAATGTCCTTCT
GGAGCGCAAGATTGCCGCATTGATGCGCGAGGATGAGAAGCGCAGCATTG
TCCTACACGAAACGATTGCCACCTGCGCTCCCAATTTCGCCGAAAAGTTA
ACCAGCTTGGATGAACGGGTGGGCAACATCATCGATGAGAAGAACAAGAT
AATCCTTGACCTGCGCTATGAGGTAACTAAGGCGCGAAAGGCACACGACG
ATCTACTGGAAACCTACGAGTGCAAGCTCAAGCAATATGGTGTGCCCACT
GACGAGTTGGGCTTCAAGCCCATCAGGAATCGGGACCAACAGCAGCTGTA
CGTGTGCGGTCCTGCGGGAATAATCACCGAGAATAAGTAG

CG4568
SEQ ID NO:243
ATGGCGGAATCTGACTCCGGAGAAAGTACGTCGTCGGTGTCCTCGTTTAT
ATCCTCATCGTCGTCTTCGCGATTAAGTGAGTTTGTGGACGCAAAGACAG
AACTGCAGGATATATATCACGATTTGAGTAATTACCTGTCCAATTTCCTA
ACCATTTTGGAGGAGACTGTCCTGTTAAAAGATCGACAAATGCTGGAGCA
CCTGTGCGCCTTCTCCAGCAGGGTGGAGGCCATTGCAAAGGTTCTTTCAC
GTGATCGAATGAAGGTGGCATTTTTTGGACGCACCTCAAATGGAAAAAGT
GCCGTGATCAATGCACTTCTGCATGAAAAAATCCTGCCCAGCGCCATGGG
CCATACCACCAGCTGTTTTTGTCAAGTGCAAGCTAATGGCTCGAATGAAA
CCGAGCACGTAAAGGTCGAGCAGGAGGATGAGCATATGGAACTGAGTGCC
CTAAGCCAACTGGCCAGTGCACATTCTCCTGGGGCCCTAAAACCCTCAAC
TCTGCTGCAGGTCAATATGGCCAAGAACCGTTGCTCGATATTGGATTACG
ATGTGGTTTTGATGGATACACCTGGAGTGGATGTAACAGCGCAACTGGAC
GATTGCCTAGATAGCTACTGCATGGATGCGGATGTTTTCATTCTAGTTCT
CAACGCCGAGTCCACTGTTTCGCGCGTGGAAAGGCAGTTCTTCAAGGACG
TGGCATCCAAACTCTCGCGTCCAAATCTCTTTATACTCAACAATCGATGG
GATAAGGCCAGCAGTCTGGAGCCGGAAATGGAGCAGAAGGTAAAGGATCA
GCATATGGAACGTTGCGTTAACCTGCTCGTGGATGAATTAGGTGTTTATT
CAACTGCACAGGAAGCGTGGGAAAGGATCTATCATGTTTCAGCACTGGAG
GCATTGCATATAAGGAATGGTCAGATTACGAATCCCTCGGGACAAACCCA
ACAGCGATATCAGGAGTTTCTGCGTTTCGAAAATGATTTTTCGAATTGCC
TCGCGGTGTCAGCGTTAAAAACCAAATTTGGTCCACACTTGCTAAGTGCG
CAGAAGATTTTAAACCAGTTAAAATCAACTCTGATATGCCCTTTCATAGA
GAAAGTAAGTCGTCTTATCGATGAGAATAAGGAGAGAAGAGCTAACTTGA
ATGCCGAAATAGAGGACTGGTTAATACTAATGCAAGAGGATAGAGAAGCG
CTTCAATATTGTTTCGAAGAACTGACTGAAATGACACAAAGAGTAGGTCG
GTGCGTTTTGAACGACCAGATAAAAACGTTAATACCCTCGTCTGTGCTAT
CATTCTCGCAACCATTTCACCCGGAATTCCCAGCACAAATAGGCCAGTAC
CAACGCTCGTTATGTGCCCATTTGGATAAACTTCTTGAAGATCGTGTCCT
TCAATGTCTCTCCATACCCCTACAAAGAAAAATATTAGATATAGAGAAAG
AAATTGGGCTTCCGATCGCCGAGAACTCTTGCGATTGGCAACTAATCTAC
GGCCTGGATTGCCAATCCTATATGAGTGACTTTCAGCCAGATCTTAGGTT
TCGATTTTCTTTGGGTTTTACTGCCCTGTGGCATCGTCTTGAAGGCAACC
TACCGTTGCACGCAAGTCCATTTCGAATTCAAAAGTTACAAAATGGTCAC
AAGAAATGTTCGCCCCTGCCACCTTTAGTTAACGGAAACCATTGGCAGAT
```

Fig. 2-C

GCTGGAATCTTTGGTGAAGTCTAAAGGTAGCTTGGGCACCGTTTTACTGA
GCGCCATGGCCATCCGTTCGTTCAACTGGCCAATTGTATTGATCCTTGGT
GGGCTCGTCGGATCCTTTTACATCTACGAGTACGCCGCTTGGACAACTGC
CGCCCAAGAGCGAAGTTTCAAGAGCCAGTACGCCAGGCTCTTGCAACAAC
GTCTGCGGTCGGATGTGCAGCAAACTGTTAGCCGTTTTGAGCTCCAGTTG
CGACAGCACCTGGCAACGGTCCGAAATTGCTGGGAAGCCCAGTCCAATGA
GACACTGAATGACCTGAACGTAAGGACCGCGGAGCTGACCAAACAAATAC
AATCGATGGAGGTGTTGCAGCTCAGCCTGAAGAAGTTTCGGGACAAGGGA
CAGCTGCTGGCCAGTCGGTTGGGAGACTTTCAAGAGACCTACTTGACCAA
GAGCTGA

CG32396
SEQ ID NO:244
ATGAGGGAGATTGTCACACTGCAGATCGGCGGAGCCGGAAATGCCATCGG
AGATTCTTTCTGGCACGTGATTTCACATGAACACGGTGTGGATTATGCTT
CTGGTCGATTTGGCGGCACCAGTCCACTTCAGCTGGAGCGGATCAATGTG
TTCTTTTAACGCAACGGCCAGCAAACGGTTCTATGCCCGCACCATACTGAT
AGACACGGAAGCCAGCACCATTCAGCGTCTCAACGCCAGCAGTCAGCTGT
ATAGGCCGGAGAACTTTGTGGCTGGATCGGAGAGTGCTGGGAACAACTTT
GCACGTGGCTATCATACGGATGGTGCCGCCATTCTAGATCAGGTGCTAGA
AAATACCCGCCGGGAGGTCGAATCGGTGGATTCGTTGCAGGGCTTTCAGT
TGCTCCACTCTATCGGAGGCGGAACTGGCTCCGGCTTGACCTCTCTAATA
ATGGAGGCCCTGGTGGAGCAGTATCCGGATAATTTACTCTGCAACTATGT
GACCATTCCGTCGCCGAATATGTCGCAGGTGGTTGTGGAACCCTATAATG
CCCTACTTAGTACTCCCGCCTTGGTTAACAATTCGCATTTAACCTTCTGC
CTTGATAACGAGGCACTGTTCCAAATCTGCAATAGAAACCTGAAGCTCAA
GATGTCCGGCTACGAGCACATTAACCACATAGTAGCCCTGACCATGTCGG
GTATAACCACTTGCCTGCGGTTTCCTGGCCAACTGAATGCTGGATTGCGC
AAGATCTATGTAAATATGGTGCCATTCCCGCGGCTGCACTTCCTCATACC
GGGATTCGCACCATTGGTCACTTGCAAGCAGCAGCAGTTCAGCAAGGGTA
CCGTTTCGGAGCTGGTGCAGCAGATCTTCTACAGTAATAATCTGCTCTGT
GCCATCGATCTTCGAAAGGGCAAACTGCTGACCGCTGCTGGAATTTTCCG
AGGAAGAATGTCACCGCGTGAGGTGGATCAACTGATGACTGGGGTGAGAA
ATAAGAATATCAACAATTTCGTGGACTGGATACCCAACAATATCAAGACG
GCTATTTGCGATATACCGCCGAGGGGCCTCAAGATGTCAGCTACATTCAT
TGGCAACACAACGGCGATTCAGACGCTGTTCCAGCGATTACTGGACGCTT
CCATGTCCATGTTGCGGCGCAAGGCCCATCTTCACTGGTACACGGGAGAG
GGAATGGAGGAACAGGAGTTCCAGGATGCGCAGCAGGAGTTACAAGCCAT
CATCGATGATTACCGCAGTAGTGCTGAGGGCGAGGATTCCGGTGGTGGCG
GTGGAGGAGGCGGTGGCCGAAGTGGAAGCGCCGAAAGCGGTGAAGAGGAG
GCCACGCCCGAAGCCCATTGTCAATATTGCACCGAATAA

CG15259
SEQ ID NO:245
ATGTCAATTATTTCCCTTGAAGTTCCTATTCAGCCGTATGCTGGTCAGCT
GCTCATCATCAATGATCTGATTCTGCCGGACTCAGGCTCTCAGGATGCAA
GCAAGGCAAAAGTCTCCATAAAGAAAAATCAACGTGCATCCTTCTTTGAC
CGCAGCAGTATCTACAAAAAGATAATGAAGCACTTGTCCCAGGGCAACCA
GGCGGATGATATCAACATTTCCGAGCAAGAATGGCTCCTGGATTCTTTTT
TGGCCGCCTTGGAGACCTACATGAAACATGTGGTCAAGAAGACTATCGAA
TTGTGCGAGCATCGAACAAGCTATCATCTGCACAACGACGAACGTTGTGT
GATGAAGAACGATATGAGGGTCACGATGATGTTCCTCAACGATCTCGAGA

Fig. 2-D

TTGCCGACTATGGATCATCGGATGACGAGACCGGCTTTTATCGCAAGCGC
CGGGCAGAGAACATCGACGAGGAGAGAAAGGTGGCTCGTCTGGAATCGGT
GAATGATACGGCCTTGCTAGCCATCTCCGGTCGAAAGCGCCCGGGAGAAC
AACTAGCCCCAGAATCTGCTCCAAGTGGTTCGAAAGTCGCCAAATTGACC
GGTGCTCCGATCCAGCGAGCATGTGCTCCGCGATTTAAGCATATGAACAT
CAGGGATGTACTGCAGTTTATGGAGGAGGACAGACGATACGCCCGGTCCA
ACATGCTCTTCGAAGCATATTTAAAATACAAGTCATAA

CG18369
SEQ ID NO:246
ATGGCATCCACACGCATGATCAGTGCTTTTACGCGCAATCCAAGATTATA
TCAACAGGTCACGGCACCCTGGAAATCGTACAATCTGTTTGGAACACCAC
TTTTTAACCACAGACTTCAGCCAGCGGATTCTCAAATCTGGAGGGGATTA
GCAGACAAGTGTGACAACAAGACTGTTATCAAGGGCGTGGTGGTGGGCGT
CTACTCCAAGGAGGGCGACGGTAAGGAGGTCAAGATGACGTCCAGCGGCG
AGAAGTTCGACGACCGAACTCAGGGCAAGGTCTCGGAGCTGTTGCGCGAA
ACTGGAATCAAGGGGGAACTGGGCAAGGGTAAGGTCTTCATGAACGTGGA
TGCCGAATTCCGGGCAGTGGCTGTGGTGGGTTTGGGCCAAGAAGGTGCCG
GCTTCAATGACCTGGAGAATATCGACGAGGGTATGGAGAATGCCCGCGTT
GCCGCTGGCGTCGGAGCTCGGGCATTGCAACTGCAGGGTTGCACGGAAGT
CTTTGTGGACTCCATGGAATATCCGGAGCAGGCGGCGGAGGGCAGTGCTC
TGGCCATCTGGCGTTACAATAGCAACAAGCGCAAGCAGGATCGCACTCAG
GTACCCAAACTGGATCTGTACGACTCACCGGATGTGGATGCCTGGACGAG
GGGTCTCTTCAAGGCGGAATCTCAGAACTTGGCTCGAAGATTGAGCGATT
CGCCGGCTAATCAGATGACCCCCACCATATTCGCCCAATCGGCGGTGGAT
GCCCTGTGTCCGTGCGGCGTTTCCGTGGAGGTGCGATCCATGGATTGGAT
AGAAATGAATCATCTCAATTCGTTTCTAATGATAGCCAAAGGCAGCTGCG
AGCCACCGGTGGTCCTGGAGGTCAGCTACTGCGGCACAGCACCCGAGGAT
CGGCCCATTCTGCTGTTGGGCAAGGGTTTGACCTACAACAGTGGCGGATT
GTGCCTGCGGCCAAAGGATTGCCTGCATATGTACCGCGGCTGCATGGCGG
GAGCAGCCGTTTGTGTGGCCGCCGTTCGAGCTGCGGCAGCCCTTTCCCTG
CCTGTAAACATCACGGCCGTACTGCCGCTCTGCGAGAATATGCCATCGGG
AATGGCTGTAAAGCCGGGTGATGTGGTCACCCTGCTCAATGGCAAGACGA
TGGGTATTGTGGATGTGAGCAAAGCTGGAACGGTGGTATTGGCTGATCCC
CTGCTCTTTGCCCAGACGACGTACAAGCCTCGTCTGGTGGTGGACTTGGC
CACCGTTGGCTATGGCGTCTGTGCTGGCCTTGGAGAATCGGCTGCCGGAT
TGTTTACCAATTCCAATTTCATAGCCAAGCAGTTCGAGAAGGCTGGCGGC
CTGACTGGAGATCGTTTATGGAGGCTGCCCTTGTGGCGCTACTTCAAGCA
GCTGGTAACCCCGAATCTCACCTTCGACATCAGCAATAGGGGCATTGGTC
CCGCCTCCAGTTGCATTGCTGCCGCCGTGCTGCACGAACTGGTTCCATGC
GCGGATTGGGCCCACATTGATATCCGGAATGTGGGCATGCTGACACGCCA
CAATCCGCTGCCGTATCTGCTCAAGGATCGGATGACCGGCCGACCCACCC
GCACCATCGTACAGTTCCTGTATCAGATGGCCTGTCCGGAAAGCAAGTAG

CG17083
SEQ ID NO:247
ATGGAGGAAATCAAGAAGTTTGACAAGCTTGCCTTCCTGGAAAGCTACCT
GCTGAAGCACAAGGAATTGGGCAAGCGACAGCGCGAGTACAAGAAGATCC
TGTCCAGCAAACTCAAGACCCGCAAGGAGACCATCATCGAGGCCAGCTTT
GAGACGGCCATCGATCAGCTGGAGGAGGAGAAAAACGATCTGCGTGCCCA
GATCTGGGTGGCCAGTGGTACGACCCACAAAAAACAGAACAATCGCTGGC
TGGAGCTGATTCGCTGCCATGTCGAGTGCCAGGAGAATCTGTCGCAGGAC

Fig. 2-E

ATTAACTCTCTGAAGACATCGATTTCCAACATGGAGAAGGAGATAAGTCG
CATGTCCAAGCAAATATACAACCTGAATCGTTTAACCATTCCGGATCAGC
AACATCAGGCCTATGTAATGCGAGCACGGAAAAGGATGACCATTTTGGAG
AATTCCCTGGAGGTGGGAGTGCGTCAGGAGTGCGGTTTTACGGCACCCAA
TGCGGATCTGCGAGAGCAGCTTATCCGCATCCTGAATCATCGCACCTTCT
TCAATGATTCATACACCAAAATGGTGCAGAAGCTGAACAGCGAGAAAAAG
TATCTCATAGATCTGATCGAATACGCTCTGAATACCTTCGATGGCTGCAT
TGAGGTGTACGAGAAAATTGATTTGTTGGCCAAAAGGGAGGCCAAGGAGC
GCGATATGAGACGTGTGGAGATGCAGGGTATTATGCGAAAGGTGGCAGCC
GATGGTGATAACACCGCCTTCCTGAATTGCAAGTCTAAGCCTCGAGAGCT
GGCCGATTTGCAGCCCAAGGAGTACAAGCGAAGGGATGAATTCCGACGGG
TGCACAACAAAAGATCAATCTCTACAACTCGGTGCTGCAGAAGATTCTC
CAGTATACGGAATCTAGCAATATGGACGAGGTGATCGATAAGTTTCAGCA
GCAGGAGAGTCTCTATTACTCGTTCTTCAACTATGCCAACGAAATGAGCT
ACCACATAACTATGCTGAATAATTCGGTGAATCGCCTGTTTGAGGATATA
GTTAACCTGAAAAAGGATAACTCCAACACGCTGCAGGACCAACTGGATCA
GATTTCCAGTCTGGAGAACAAGGTGCGTAACAAACAGGAATCCAACATGG
AACTGCACAAGGCGCGGGAAAACAACGATGCACGTTTGGAGAATCTTCTA
CAGGGCGTGGAGACGGTCTGCGAGATGTGTTCCATAGATGCCAGTCCGCT
GACCAAACTCCTTGGTGACCACACCCACGTCAATCTGGTTAATGTCAATC
GATTCTTGAAGCTGCTCGAGACAAGGGTCCAGGAGCTGACGGCTAGTGTT
TATGTGATGGAGCGCCAAGAGGAGGGCCGCTTCGACTATGTGGTCAAGCA
GATCGAGAAGATCTGCGAGCTGCCCACCGATCTCAATGACATTGTGCTCA
CCCAGCAGTGTCCCGAGTGCGCCGAGGGTGAAGCCTTCAACATGGATGAG
GGCGGCGATGGTGTCCTTGTCCACACGGTCGCCGAGGCCAAGAAGAAGCT
GTACGAGAAGGTTACGCAGCCGGAGATGCAGTACCGCCTGCACAGCATCA
GCCAGTGTCGTCTGCCGCGATCCCGTCTCCTGGCCGCCAAGCGCAACATG
TAG

CG9313
SEQ ID NO:248
ATGGCCACAAAACCGGGAAAAGGTGACGGCAAGCAGGTGAAGGGAAAAAG
GACCTCCAAGAACAAGACAGATGGCCCCGGCGGTGGTGGCGGCGATGCCG
ATGACTTCGATGCCTGGATGAAGTCGCGCCAGCTGCTCAAGCCCGATGAC
CAGCTCGATCTCACCGAGGCGGAACTGGGCGAGGAGATCACCAAGGTGCT
GACTCCCACCAACACGAACATCGTTCGCAATCTCGTGGTCTATAGCTTCA
AGGAAGGCGAGTTTGTTCCGGCTCCGTTGCCCGGCAATACGGTCACCCTA
ATCGCCTTTGCCGGCAACTCACTTCACGTGGACTCCGATGAGGGTCGCCG
TCAGATCGAGGAGTCCGACGAGATTGGCTACCCACTGCCCATGCCCAACT
ACACTGTGGTGGAGCAGCGCGAGACGGATAACGTCGACGGTGAGGAGGGA
GAGGGCGAGGAGGATGATGATGGGGCCACCGCAAAGGACGCCGCCGTAGA
AGACGAGGATGTCGAGGAGGAGGACGACGAGGAGGCCAAGGGCACCGAAG
GCGATGAGGGCGAGGGCGAAGGCGAGGGAGAGGGTGCTGCTGCCCGCCAG
GAGGACGATGAGCCCGCCCACCAAGCGGCGGCCGTTTCATCCAAGAAACG
CAAGCTAATCAACCAGTTCAACTACTGCGAACGTGGTGCCCTCACCTACA
CAAATCCCAAAAGGAATGTAGACACCCAGACCATACCCCCACCCCGTTCC
CAGTTTGGAGCCAATGTGCTGCAGTGGGTCATCTATGATTCCTATATGGA
GAACTTTGCGGAGTCCCAGAAGGACGGCACCAAGAAGGAGGAGCGCAAGC
GCGGCAAGAGGGAGAAGAAGTTCCGGGATAAGTCGGCCATTGCCGAGCAG
CTCAACAAGAAGTATCTCAAATGCTGGCAGATACTCGAGCGCATGATCAA
TCAGAATATCTACGATGACATCGCCCACGACTATCGCTACTGGGAGGATC

Fig. 2-F

```
CGGCTGATGAGTTTCGTGAGGGTGAGGGCAACCTGCTGCCACTCTGGAAG
TTTCAGTACGACAAGACCAAGAAGATGAACGTCACCGACATCCTGTTCAA
TCCGAGCTACTATGATCTCTTCGCCGTCTGTTTCGGATCGCATGACTTCA
TGAAGCAGACCAATGAGGGTTACTTGTGTCTGTTCACCGTTAAGAATCCC
TCATTCCCGGACTATATAATTCAAACCGACTGTGGTGTCATGTGCTGTGA
CATCCACCCAACGTATCCTTTCCTGGCCGTAATCGGTCTCTATGACGGCA
ATGTGGCGGTCTACAATCTGCGCGAGGACTGCAAGGAACCACTCTATGTG
TCCAGAGGAGTCAACTGCAAGCACGGCGAGTGCGTGTGGCAGATCAAGTG
GGGTTTGGACATGGCCGATGGCGAGGTGAACTTCTTTTCGGTGTCCTCCG
ATGGGCGCGTCTTCAACTGGATTCTCATGCAGAACAAACTGTGGGTAACC
ACCATCATCACATTGTACCGCGAAAACGGACTGGTTGACGGACCAGATGG
CACAAAGGTCACGCTGAAGAGCGGAGGATCCTGCATGGTGTTCCATCCAG
TGGATAATAAGATATTTCTGGTGGGCACCGAGTGTGGTTACATCTACAAG
TGCAGCACGGCGTTCAGCTCCAAATACCTGATGACCTACTATGCCCACAA
CATGTCCGTCTATCGCATTGACTTCAATCGCTTCAACAGCAACATCTTCG
TGTCCTGTGGCGCCGACTGGATGGTCAAGGTGTGGGAGGATATGCGTCCA
GATCCGCTGTTCATATTCGATCTTGGTGCCGCCGTTGGCGATGTCAAGTG
GGCACCTTACTCGAGCACCGTCTTCGCAGCGGTGACCACCGAGGGCAAGG
TCCACGTTTTCGACCTAAATGTGAATAAGTACAAGGCCATCTGCATCCAG
GCCGTGGTGCCCAAGCGAAAGAACAAGCTCACCAGGTTATCCTTCAACGA
GAAGCTCGCCTTCATTGTGGTGGGCGATGAGAAGGGCGTCACCACTTCGC
TGAAGCTATCGCCCAATCTCCGGATGATGGTGAAGCCGCCGAAGAAGCAG
CTGTATCTCGACCAGAACACCCTCCAGATTGGCAAGTTGGAGAAGCTGCT
TTCCCTGGTGCGGGAACTTCCGGAAGGTTCAACTGCGGTGCCCGATGCAG
CCACAACCGTGCGAAGTTAA
```

BIOLOGICAL CONTROL OF INSECTS

CROSS-REFERENCE TO RELATED APPLICATIONS

This application is the § 371 U.S. National Stage of International Application No. PCT/IB2014/064643, filed 18 Sep. 2014, which claims the benefit of U.S. Provisional Application Ser. No. 61/880,498, filed Sep. 20, 2013, which are incorporated by reference herein.

BACKGROUND

The sterile insect technique (SIT) is a species-specific biological control method that can reduce or eliminate populations of pest insects without the need of chemical pesticides. The technique requires the release of large numbers of sterilized males, which then compete with wild males for female mates to reduce the population (Knipling, 1960; Vreysen et al., 2000; Klassen et al., 1994; Hendrichs et al., 1995; Bloem and Bloem, 1999). Radiation or chemosterilants are typically used to sterilize males for SIT, but these treatments can decrease their ability to compete for mates, which often necessitates the production and release of many more sterile males to increase efficacy (Holbrook and Fujimoto, 1970; Mayer et al., 1998; Helsinki and Knols, 2008). SIT is considered more effective if females are not released (Knipling, 1959; Robinson, 2002), as sterile female insects can still damage crops or transmit disease. Genetic sexing techniques have been developed for some insects, such as the medfly, to preferentially eliminate females before they mature. These typically involve chromosomal translocations that link the male-determining chromosome to a dominant selectable marker, while the females are homozygous for a recessive deleterious gene. Unfortunately, these translocations tend to break down when insects are mass-reared due to male chromosomal recombinations (Franz et al., 1994).

Conventional SIT has been used to control mosquitoes previously (Lofgren et al. 1974), but has not been used extensively due to the limited competitiveness of the sterile males. New transgenic methods, using genetically altered mosquitoes that carry and spread deleterious genes are being developed (Alphey et al, 2010), but the release of genetically-modified insects in many communities/countries may be prohibited or delayed until public opinion and regulatory issues are fully considered.

SUMMARY OF THE APPLICATION

Provided herein are modified insects. In one embodiment, a modified insect includes decreased expression of a testis-specific coding region compared to a control insect. In one embodiment, the modified insect is male. In one embodiment, the modified insect includes, when compared to the control insect, reduced fertility, reduced fecundity, or a combination thereof. Optionally and preferably, the competiveness of the modified insect is not significantly reduced compared to the control insect.

In one embodiment, the modified insect is a member of the family Culicidae (e.g., *Aedes* spp., *Anopheles* spp., or *Culex* spp.), the family Tephritidae (e.g., *Ceratitis capitata*, *Anasirepha* spp., or *Bactrocera* spp.), the family Tortricidae (e.g., *Cydia pomonella*), the Order Diptera (e.g., *Cochliomyia hominivorax* or *Glossina* spp.), or the Order Lepidoptera (e.g., *Orgyia anartoides*). In one embodiment, the modified insect is a mosquito, such as *Aedes aegypti*, *Aedes albopictus*, *Aedes vexans*, *Anopheles gambiae*, *Anopheles farauti*, *Anopheles quadrimaculatus*, *Anopheles stephensi*, *Culex pipiens*, *Culex quinquefasciatus*, or *Culex tarsalis*. In one embodiment, the testis-specific coding region is selected from Table 2 or a homologue thereof. The expression of more than one testis-specific coding region may be decreased.

In one embodiment, the modified insect further includes decreased expression of a coding region encoding a sex differentiation polypeptide, such as a doublesex female splice variant, compared to a control insect.

Also provided herein are methods for making a modified insect. In one embodiment, the method includes administering to an insect, such as a juvenile insect, a composition that includes a double stranded RNA (dsRNA) that inhibits expression of a testis-specific coding region. The juvenile insect is allowed to mature into an adult, wherein the adult insect has reduced fertility, reduced fecundity, or a combination thereof, compared to a control insect. In one embodiment, the testis-specific coding region is selected from Table 2 or a homologue thereof. The expression of more than one testis-specific coding region may be decreased.

In one embodiment, the method is used to make a modified insect that is a member of the family Culicidae (e.g., *Aedes* spp., *Anopheles* spp., or *Culex* spp.), the family Tephritidae (e.g., *Ceratitis capitata*, *Anastrepha* spp., or *Bactrocera* spp.), the family Tortricidae (e.g., *Cydia pomonella*), the Order Diptera (e.g., *Cochliomyia hominivorax* or *Glossina* spp.), or the Order Lepidoptera (e.g., *Orgyia anartoides*). In one embodiment, the modified insect is a mosquito, such as *Aedes aegypti*, *Aedes albopictus*, *Aedes vexans*, *Anopheles gambiae*, *Anopheles farauti*, *Anopheles quadrimaculatus*, *Anopheles stephensi*, *Culex pipiens*, *Culex quinquefasciatus*, or *Culex tarsalis*.

In one embodiment, the administering includes feeding the composition to the insect. The dsRNA may be present in bacteria that are fed to the insect, and the bacteria may be living or inactivated. In one embodiment, the insect is a larva or a pupa. In one embodiment, the testis-specific coding region is selected from Table 2 or a homologue thereof. In one embodiment, the composition further includes at least one additional dsRNA that inhibits expression of a testis-specific coding region. In one embodiment, the method further includes administering to the insect a second dsRNA that inhibits expression of a coding region encoding a doublesex female splice variant. Also provided is a modified insect produced by the method, and a population of an insect produced by the method.

Further provided herein are methods for biological control of an insect. In one embodiment, the method includes releasing into an environment a population of a modified insect described herein, wherein the number of viable progeny in the next generation is reduced. In one embodiment, the reduction is determined by comparison to release of a wild-type insect into the environment.

Also provided herein are methods for producing a population of an insect that is male-biased. In one embodiment, the method includes administering to a population of an insect at a juvenile stage a composition that includes a double stranded RNA (dsRNA) that inhibits expression of a coding region encoding a doublesex female splice variant, and wherein the population of the insect has a reduced number of males compared to a population of the insect not administered the composition.

Also provided are the double stranded RNAs disclosed herein, including the single stranded RNA polynucleotides and single stranded DNA and double stranded polynucleotides corresponding to the double stranded RNAs.

The tern "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Conditions that are "suitable" for an event to occur, or "suitable" conditions are conditions that do not prevent such events from occurring. Thus, these conditions permit, enhance, facilitate, and/or are conducive to the event.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. Testis-specific coding regions of *Aedes aegypti* encoding polypeptides.

FIG. 2. Testis-specific coding regions of *Drosophila melanogaster* encoding polypeptides.

DETAILED DESCRIPTION OF ILLUSTRITIVE EMBODIMENTS

Provided herein are methods of producing insects, such as mosquitoes, that are sterile and/or have reduced fecundity. Such insects may be used in sterile insect technique (SIT) programs to eradicate pests and thereby reduce disease transmission and/or economic losses that can be caused by pests. SIT is a biological method of controlling pest insects by releasing large number of sterile males into a locality, where they compete with wild males for mates, and can effectively reduce or eliminate the pest population. Existing methods of producing sterile males for mosquito or other pest insects have traditionally relied upon the use of radiation or broad-spectrum chemosterilants to sterilize males, but these methods typically render the males weak and not highly competitive when they are released. Some new methods that rely on producing genetically-modified mosquitoes have been developed, but these approaches require the release of insects that can spread the gene into the population, which may have unforeseen impacts on the population beyond the region of concern.

Accordingly, provided herein are methods for making modified insects. As used herein, the term "modified" refers to an insect that has been altered "by the hand of man" through the introduction of an exogenous polynucleotide. As used herein, an "exogenous polynucleotide" refers to a polynucleotide that has been introduced into an insect and includes, but is not limited to, a polynucleotide that is not normally or naturally found in an insect. In one embodiment, the exogenous polynucleotide is a double stranded RNA (dsRNA). In one embodiment, a modified insect described herein has decreased expression of a testis-specific coding region compared to a control insect, decreased expression of a female-specific coding region compared to a control insect, or a combination thereof. A modified insect having decreased expression of a testis-specific coding region and/or decreased expression of a female-specific coding region may include an exogenous polynucleotide. A modified insect may be at any developmental stage, such as larva, pupa, or adult. In one embodiment, a modified insect is a larva or pupa that will develop into an adult that has reduced fertility, reduced fecundity, or a combination thereof. In one embodiment, a modified insect is an adult and has reduced fertility, reduced fecundity, or a combination thereof. As used herein, a "control" insect is the same species of insect but is unmodified relative to the modified insect.

Insects that may be modified using the methods described herein include, but are not limited to, pests, such as insects that act as vectors for viral, bacterial, and/or parasite-based diseases; and/or inflict damage on crops, fruits, vegetables, animals, and/or humans. In one embodiment, an insect is a member of the family Culicidae. Examples of such insects include mosquitoes, such as *Aedes* spp. (e.g., *A. aegypti, A. albopictus,* and *A. vexans*), *Anopheles* spp. (e.g., *A. gambiae, A. farauti, A. quadrimaculatus, A. stephensi, A. arabiensis*), and *Culex* spp. (e.g., *C. pipiens, C. quinquefasciatus,* and *C. tarsalis*). In one embodiment, an insect is a member of the family Tephritidae. Examples of such insects include fruit flies such as *Ceratitis capitata* (commonly referred to as the Medfly), *Anastrepha* spp. (e.g. *A. ludens, A. suspense, A. oblique*) and *Bactrocera* spp. (e.g., *B. tryoni, B. dorsalis,* and *B. oleae, B. cucurbitae*). In one embodiment, an insect is a medical or animal pest that is a member of the Order Diptera, such as a screw worm fly (*Cochliomyia hominivorax*), or tsetse fly (*Glossina* spp, such as *G. palpalis, G. fuscipes, G. morsitans, G. tachinoides, G. longipalpis, G. fusca, G. tabaniformis, G. brevipalpis, G. vanhoofi, G. austeni*). In one embodiment, an insect is a member of the Order Lepidoptera (e.g. member of the Lymantriidae family, e.g. *Orgyia anartoides*) or of the family Tortricidae, e.g. *Cydia pomonella*).

In one embodiment, a method for making a modified insect includes administering to an insect a composition that includes a polynucleotide. As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences such as regulatory sequences. Coding sequence, non-coding sequence, and regulatory sequence are defined below. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

In one embodiment, the polynucleotide may be a double stranded RNA (dsRNA) that inhibits expression of a testis-specific coding region. In another embodiment, the polynucleotide may be a DNA sequence that encodes a dsRNA. It should be understood that the sequences disclosed herein as DNA sequences can be converted from a DNA sequence to an RNA sequence by replacing each thymidine nucleotide with a uridine nucleotide. The insect may be juvenile or adult. A juvenile insect includes all stages except adult, e.g., larva and pupa. In one embodiment, the insect administered a composition described herein is a larva.

As used herein, a "coding region" is a nucleotide sequence that encodes an unprocessed preRNA (i.e., an RNA molecule that includes both exons and introns), and is processed to result in an mRNA that is translated into a polypeptide. The boundaries of a coding region are generally determined by a transcription initiation site at its 5' end and a transcription terminator at its 3' end. As used herein, a "testis-specific coding region" is a coding region that is expressed in the testis, but is either absent or expressed at undetectable levels (using qRT-PCR techniques) in other male tissues or in females. As used herein, a "female-specific coding region" is a coding region encoding a sex differentiation polypeptide that is expressed in both males and females, but a different splice variant is expressed in males and females. A "female-specific coding region" is the variant that is expressed in females only.

As described in Example 1, testis-specific coding regions have been identified that, when expression is decreased, result in decreased fertility and/or decreased fecundity, and do not significantly reduce competitiveness. In one embodiment, the testis-specific coding regions encoding polypeptides that may be decreased in a modified insect include, but are not limited to, the coding regions available at the Genbank accession numbers AAEL001684, AAEL002275, AAEL004231, AAEL004471, AAEL004939, AAEL005010, AAEL005975, AAEL006726, AAEL006975, AAEL007188, AAEL007434, AAEL010639, and AAEL011310. Each of these coding regions are transcribed and processed to result in an mRNA sequence, which is shown in FIG. 1 and Table 1.

TABLE 1

| Genbank No. | SEQ ID NO: of mRNA (see FIG. 1) |
|---|---|
| AAEL001684 | 1 |
| AAEL002275 | 2 |
| AAEL004231 | 3 |
| AAEL004471 | 4 |
| AAEL004939 | 5 |
| AAEL005010 | 6 |
| AAEL005975 | 7 |
| AAEL006726 | 8 |
| AAEL006975 | 9 |
| AAEL007188 | 10 |
| AAEL007434 | 11 |
| AAEL010639 | 12 |
| AAEL011310 | 13 |

In one embodiment, the coding regions shown in Table 1 may be used in methods where the insect administered a dsRNA is a member of the family Culicidae. In one embodiment, the insect is *Aedes aegypti*. In other embodiments, a dsRNA directed to a coding region that is a homologue of a coding region shown in Table 1 may be used with other insects. For instance, Example 1 shows that dsRNA directed to a coding region of *Drosophila melanogaster* that is a homologue of a coding region shown in Table 1 reduces fertility and/or fecundity, and does not have a significant effect on competitiveness in *D. melanogaster* (see Table 7). This evidence that coding regions silenced *A. aegypti* genes, a member of the family Culicidae, also worked in *D. melanogaster*, a member of the family Tephritidae, shows the applicability of the methods described herein for use with other insects. Thus, coding regions present in other insects that are homologues of the coding regions disclosed herein (e.g., in Table 1 and the *D. melanogaster* coding regions shown in Table 7) can be used for making dsRNAs to silence testis-specific coding regions with the expectation that the dsRNAs will reduce fertility and/or fecundity in other insects.

Coding regions that are homologues are coding regions that share ancestry, e.g., they are both derived from a coding region present in a common ancestor. The skilled person can easily determine if a coding region in a non-*A. aegypti* insect is a homolog of a coding region disclosed herein through the use of routine methods. In one embodiment, the skilled person can use the nucleotide sequence of a coding region disclosed herein and design degenerate PCR primers for use in a low stringency PCR. Low stringency PCR is a routine method for identifying homologs of known coding region. In another embodiment, the skilled person can use readily available databases to identify in another insect a homolog of a coding region disclosed herein. Examples of suitable databases include, but are not limited to, VectorBase (available through the world wide web at vectorbase.org) and GenBank (available through the world wide web at ncbi.nlm.nih gov/genbank).

In another embodiment, the skilled person can identify a homolog of a coding region disclosed herein by the level of sequence identity between the coding region disclosed herein and another coding region. In one embodiment, when two nucleotide sequences are being compared, percent identities greater than 50% are taken as evidence of possible homology. The E value (Expect value) indicates the number of hits (sequences) in the database searched that are expected to align to the query simply by chance, so a E value less than 0.01 (i.e., less than 1% chance of the sequence occurring randomly), coupled with a percent identity of greater than 50% is considered a suitable score to identify a probable homolog. Methods for determining nucleotide sequence identity between two sequences are readily available and routine in the art. In one embodiment, coding regions in an insect that are homologues of the coding regions in Table 1 may be identified using the BLAST-X algorithm against the non-redundant database at NCBI with default parameters. A candidate coding region is considered to be a homologue of a coding region disclosed in Table 1 if the candidate coding region has at least greater than 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% nucleotide sequence identity to the respective coding regions in Table 1.

Decreased expression of one or more of the coding regions disclosed in Table 1 may result in decreased fertility, decreased fecundity, or a combination thereof in an insect. Fertility refers to the ability of a population of males to yield viable eggs after presentation to a virgin mate (see Table 4). A population of males receiving one or more dsRNA that targets one or more mRNA is considered to have sufficiently decreased fertility if at least 50% of the males in the population are sterile, e.g., unable to produce viable eggs after presentation to a virgin female. Decreased fecundity refers to a reduction in the number of progeny produced by an incompletely sterile male. A fertile male is considered to have sufficiently decreased fecundity if the number of progeny produced by an incompletely sterile male is reduced by at least 50% compared to a control male.

While decreased expression of a testis-specific coding region often results in reduced fertility and/or reduced fecundity, it was expected that certain mutations in testis-specific coding regions would also reduce the competitiveness of the male. Competitiveness refers to the ability of a male insect to seek mates and compete with wild-type male insects for a female insect. Releasing a population of modified male insects in an environment for population control is ineffective if the males are unable to compete with the wild males for females. As described in Example 1, several testis-specific coding regions were identified in which silencing did not have a significant effect on competitiveness of the insect. Competitiveness can be measured by deteii-nining whether males administered one or more dsRNA that targets a coding region disclosed in Table 1, or a homologue thereof, (and having decreased fertility and/or decreased fecundity) causes a reduction in population when competing with control males (see Table 6). Decreasing expression of a coding region disclosed in Table 1, or a homologue thereof, does not significantly alter competitiveness of a male insect if a population size is reduced by at least 20%. Methods for determining whether competitiveness is altered are described herein. In one embodiment, competitiveness can be determined by exposing 5 dsRNA-treated males and 5 untreated males to 10 virgin females, determining the number of progeny, and comparing to the number of progeny from mixing 5 untreated males to 10 virgin females.

In one embodiment, the method includes administering to the insect a dsRNA that inhibits expression of a sex differentiation polypeptide. Examples of suitable sex differentiation polypeptides include those that, when silenced in a developing insect, inhibit the development of females and increase the likelihood the developing insect will be male by the adult stage. When used with a population of developing insects, a method that includes administration of such a dsRNA will result in a male-biased population. For instance, a population of developing insects administered such a dsRNA will result in a population of adults that are, are at least, or are no greater than, 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 100% male. In one embodiment, an insect is administered a dsRNA that decreases expression of one or more testis-specific coding regions and a dsRNA that inhibits expression of a sex differentiation polypeptide.

Examples of suitable sex differentiation polypeptides that may be targeted in some insects include, but are not limited to, doublesex, sex lethal, and transformer. The function of these proteins have been well described in the model insect species *Drosophila melanogaster*, and related genes encoding some or all these proteins have been identified in a variety of insects (Gempe and Beye, 2010). Typically, a sex differentiation polypeptide is expressed in both males and females, but a different splice variant is expressed in males and females. The doublesex gene has been found in all insects examined to date, and usually functions in a manner similar to that observed in *D. melanogaster* (Salvemini, 2011). The transformer gene has been found is many insects examined, and evidence suggests that it is differentially spliced in females and males. A dsRNA for use in silencing a sex differentiation coding region is designed to target an mRNA that is necessary for the development of females. Thus, the splice variant that is expressed in insects that will become female is targeted, while the splice variant that is expressed in insects that will become male is not targeted. The identity of these splice variants is known for many insects. For those insects where the identity of the splice variants is not known, it can be easily determined by the skilled person by comparison with the known splice variants. Any dsRNA that decreases expression of the protein encoded by the doublesex gene may be used. Examples of two dsRNAs are shown in Table 2, and one or both may be used.

A dsRNA used in a method described herein includes a sense strand and an anti-sense strand. The sense strand is at least 19 nucleotides in length; however, longer lengths are generally more desirable. Thus, the sense strand may be, but not limited to, at least 50, at least 100, at least 200, at least 300, or at least 400 nucleotides, for instance. In all vertebrates, dsRNAs greater than 30 nucleotides in length will induce an interferon-mediated cell immune response, leading to cell death. Invertebrates, including insects, lack this interferon-based response, and hence, longer dsRNAs can be delivered. The sense strand is substantially identical, or identical, to a mRNA that is targeted by the dsRNA, i.e., a target mRNA. As used herein, the term "identical" means the nucleotide sequence of the sense strand has the same nucleotide sequence as a portion of the target mRNA. As used herein, the term "substantially identical" means the sequence of the sense strand differs from the sequence of a target mRNA at some number of nucleotides, but the ability of the complementary antisense strand to bind to and silence expression of the target mRNA is maintained. For instance, the sequence of the sense strand differs from the sequence of a target mRNA at 1, 2, 3, 4, 5, 6, 7, 8, 9, 10, or more nucleotides, while the remaining nucleotides are identical to the sequence of a polynucleotide, such as a mRNA.

The other strand of a dsRNA polynucleotide, referred to herein as the anti-sense strand, is substantially complementary, or complementary to the sense strand. The term "complementary" refers to the ability of two single stranded polynucleotides to base pair with each other, where an adenine on one polynucleotide will base pair to a thymine or uridine on a second polynucleotide and a cytosine on one polynucleotide will base pair to a guanine on a second polynucleotide. An antisense strand that is "complementary" to another polynucleotide, such as a target mRNA, means the nucleotides of the antisense strand are complementary to a nucleotide sequence of a polynucleotide, such as a target mRNA. As used herein, the term "substantially complementary" means the antisense strand includes 1, 2, 3, 4, 5, 6, 7, 8, 9, 10, or more nucleotides that are not complementary to a nucleotide sequence of a polynucleotide, such as a target mRNA.

Also provided herein are the single stranded RNA polynucleotides and single stranded DNA polynucleotides corresponding to the sense strands and antisense strands disclosed herein. Also provided herein are the double stranded polynucleotides disclosed herein, including the complements of the single stranded polynucleotides.

A dsRNA described herein may include overhangs on one or both strands. An overhang is one or more nucleotides present in one strand of a double stranded RNA that are unpaired, i.e., they do not have a corresponding complementary nucleotide in the other strand of the double stranded polynucleotide. An overhang may be at the 3' end of a sense strand, an antisense strand, or both sense and antisense strands. An overhang is typically 1, 2, or 3 nucleotides in length. In one embodiment, the overhang is at the 3' terminus and has the sequence uracil-uracil (or thymine-thymine if it is a DNA). Without intending to be limiting, such an overhang may be used to increase the stability of a dsRNA. In one embodiment, if an overhang is present it is not considered when determining whether a sense strand is identical or substantially identical to a target mRNA, and it is not considered when determining whether an antisense strand is complementary or substantially complementary to a target mRNA.

The sense and antisense strands of a double stranded RNA described herein may also be covalently attached, for instance, by a spacer made up of nucleotides. Such a polynucleotide is often referred to in the art as a hairpin RNA or a short hairpin RNA (shRNA). Upon base pairing of the sense and antisense strands, the spacer region typically forms a loop. The number of nucleotides making up the loop can vary, and loops between 3 and 23 nucleotides have been reported (Sui, 2002; Jacque, 2002). In one embodiment, an shRNA includes a sense strand followed by a nucleotide loop and the analogous antisense strand. In one embodiment, the antisense strand can precede the nucleotide loop structure and the sense strand can follow.

A dsRNA described herein may be modified. Such modifications can be useful to increase stability of the polynucleotide in certain environments. Modifications can include a nucleic acid sugar, base, or backbone, or any combination thereof. The modifications can be synthetic, naturally occurring, or non-naturally occurring. A dsRNA can include modifications at one or more of the nucleic acids present in the polynucleotide. Examples of backbone modifications include, but are not limited to, phosphonoacetates, thiophosphonoacetates, phosphorothioates, phosphorodithioates, phosphoramidates, methyl phosphonates, chiral-methyl phosphonates, 2-O-methyl ribonucleotides, and peptide-nucleic acids. Examples of nucleic acid base modifications include, but are not limited to, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), or propyne modifications. Examples of nucleic acid sugar modifications include, but are not limited to, 2'-sugar modification, e.g., 2'-O-methyl nucleotides, 2'-deoxy-2'-fluoro nucleotides, 2'-deoxy-2'-fluoroarabino, 2'-O-methoxyethyl nucleotides, 2'-O-trifluoromethyl nucleotides, 2'-O-ethyl-trifluoromethoxy nucleotides, 2'-O-difluoromethoxy-ethoxy nucleotides, or 2'-deoxy nucleotides. Polynucletotides can be obtained commercially synthesized to include such modifications (for instance, Dharmacon Inc., Lafayette, Colo.).

A dsRNA useful herein is biologically active. A biologically active dsRNA causes the post-transcriptional inhibition of expression, also referred to as silencing, of a target coding region. Without intending to be limited by theory, after administration of dsRNA to an insect, the antisense strand of the dsRNA will hybridize with a target mRNA and signal cellular endonucleases to cleave the target mRNA. The result is the inhibition of expression of the polypeptide encoded by the mRNA. Whether the expression of a target coding region is inhibited can be determined by, for instance, measuring a decrease in the amount of the target mRNA in the cell, measuring a decrease in the amount of polypeptide encoded by the mRNA, or by measuring a change in a phenotype associated with expression of the polypeptide encoded by the mRNA.

Examples of polynucleotides that may be used to silence the expression of mRNAs encoded by the coding regions disclosed in Table 1 and in Table 7 are shown in Table 2. Also included in Table 2 are examples of polynucleotides that may be used to silence the expression of mRNAs encoded by the female splice variant of the doublesex coding region.

TABLE 2

| target mRNA encoded by coding region at Genbank No. | Exemplary dsRNA for use in silencing expression (only one strand shown). |
|---|---|
| AAEL001684 | CTGTGCCGGTTATTCAGCTCGTACGGCAACGTCAAGTCAACGAAAATCATCGTAGATCGGGCGGGCGTCAGC<br>AAAGGCTACGGATTCGTAACGTTCGAAACCGAACACGAGGCACAAAGACTGCAGAGCGATGGAGACTGTATC<br>GTGCTGAGGGACCGTAAGCTAAACATAGCACCAGCGATTAAGAAGCAAGTAAGTTGGCACCATACAATCTGC<br>GCGACGAACGGTGCCGTGTACTACGCAGCCACACCCCCGACGCCGACGATCAACAACATCCC<br>(SEQ ID NO: 14) |
| AAEL002275 | AGATCGAGCACTGTTTCCGAGCTTATGATATCGGCGGAGAAGAGTTACTTCGGAGAGAACACATGATGATAT<br>TGTTGCGGAGTTGTTTCATCAAGCACCAAGAAGAGGAAGTCGAAGAATCGGTTAAGGACATGGTCGAAATTC<br>TTATCCGTCGAATGGACGTTGATCGAGATGGAGCCATTTCCTTGGATGACTTCCGACAATCCGTTCACAAGT<br>CACCAGAACTTCTAGAGTGCTTCGGCCAGGCACTTCCAGATCGGGCCCATGTATACG<br>(SEQ ID NO: 15) |
| AAEL004231 | AGCCAAAGGAAGTACGGTCATCGATGGGGTGGACACATCCAGTATGTCCCGCGAACAGCTAGAACAGTTTGC<br>GCTCCGGCTTCGCAACGAGATGGAACGGGAACGCGAGGAGCGAAACTTCTTCCAGCTGGAGCGGGACAAACT<br>GCGCACGTTCTGGGAAATCACGCGCAAACAGCTCGAGGAAGCGAAAGCCGTGATACGCAACAAAGAACGTGA<br>CGTAGAGGTTGCCCAAGAACTTGCCGACCAGGACACGAAAAATGTGATGCAGGAGATGAAGCATCTGCAGTA<br>CGAGCATCAGTCGCACATCGGAGAGCTGAAAG<br>(SEQ ID NO: 16) |
| AAEL004471 | CGCGCCAAGAAGAAGATCAACGACATCTTCGGCGAGATCGAGGACTATGTGGTGGAGACAACCGGATTCATC<br>GATGCCCTCCCGACGATGGTGGAAATCGTGGACAAAGCCGAGTCGGAGCTATTCCGGAGCTATGTGCTGAAA<br>GTGTCCGGCATCCGGGAGGTGCTCGCCCGTGACCACATGAAGGTGGCCTTCTTTGGGCGCACCTCCAACGGG<br>AAAAGTTCAGTGATCAACGCTATGCTGCGGGACAAAAT<br>(SEQ ID NO: 17) |

TABLE 2-continued

| target mRNA encoded by coding region at Genbank No. | Exemplary dsRNA for use in silencing expression (only one strand shown). |
|---|---|
| AAEL004939 | TATCCTGGGCAGCTGAACTCGGATCTTCGAAAACTTCTGACCAACATGGTACCCTATAGGAAACTTCACTTT<br>TTCGTACCGGGTATTGCGCCGCTAACATCGAAGGAAAGTCAATGCTACAGAAGTCTCTCCGTTTCGGAGTTA<br>GTCTATCAAATTTTTGATGAACAAAACCTCATGGCAGCTTGCTCGCCATCCAGAGGAAAATATCTAACGCT<br>GCTGCCCTCTTCCGGGGACGAGTATCTACCAGAAATGTGGAAGAACAAATCGCCAACGTAAGGCAGAAAAAT<br>CACGGTACCTTCTCGCATTG<br>(SEQ ID NO: 18) |
| AAEL005010 | GTTTTCGTCGGTCCGGTTAGCCAAATACATCAGCAAGAATCAGAACGTCCAAACGCTGGCCTGTAAGGTGAT<br>CGACGTCCGCAAGGGGACTGAAGAATTCATCAAGAAGTTCTTTCCCCGGGAGCTCAGCGTGTTGATGAAGAT<br>CCGCCATCCAAACATCATCAAAATCCACAGCATTCTGAAGCGGGAACGGATGGTGTTCATCTTTATGGATTA<br>CGCCGA<br>(SEQ ID NO: 19) |
| AAEL005975 | TGGACAAGGCGGAACAAAAGCGACACGAGGAACAGGAACGTGAAATGTTGATGCGAGCAGCCAAGTCTCGAT<br>CAAAAACGGAAGATCCGGAGCAAGCTAAACTTAAGGCTAAGGCGAAGGAAATGCAACGAGCAGAGATGGAGG<br>AACTTCGACAGCGAGACGCTAATTTGACGGCCCTGCAAGCCATTGGACCACGGAAAAAGCCTAAACTGGAGG<br>AGGGAGCAACTACGACTGTTACGGTTAGTTGTCCAGCACTTGTTTCGGTCTTCACATGTTTTTCAACTCCGT<br>TTTTCTGTTTTTTTTTAGCCTGGTGCATCCGGCATTGGAGTGGGAGCAAGCGGGAAGACCGCCACCCCGTTG<br>AGGCCTCGAATCAAG<br>(SEQ ID NO: 20) |
| AAEL006726 | GCATTCCTGTTCTCGTTCCCCAAACACTTGTGGCGATTTTGCGAACGCGGTCGTCTTGAAACGTTGTGTCAC<br>AATCTGACTTCTATCCTTTCACCTGGTGCGTGGACTCGGAAGCGTAAAGCCTTAACTCTACTTTATTTGACC<br>CAAGAGAGCCGCAAGGGACACAACAAATACGCATTGATTTTTATCGGATGTGAGATTCTCAACTTTTTCATA<br>GTCCTCCTGAACATGTTCTTGATGAACTTCTTGTTCGGAGGTTTTTGGGCCAGTTACCAACCGGCCATTCAG<br>GCACTGCTTTCACTGGACATGAACGCCTGGACTTCGTATAATTCTCTGGTCTTTCCGAAGCTGGCCAAATGT<br>GACTTCA<br>(SEQ ID NO: 21) |
| AAEL006975 | GCCATTTCGATGCCAAAACGGAAGGACAGCTCGTAAATCTAATCAAAGAGTCAAATCTGAAAGGAAAAGTTG<br>GACAAGTCAAGGTGTTCAACAACATCGATCCGGACTTCGGTTCGGTGGCCGTTGTAGGACTCGGTTTGGAAG<br>GGCTCGGGTACAATGAGCTTGAACAGCTGGACGAAGGCCTCGAGAACGTTCGTATCGCGTCTGGTGTAGGTG<br>CTAAGTGTCTAGCGAAGCAAGGATGTTCCCGGATTTCAGTCGA<br>(SEQ ID NO: 22) |
| AAEL007188 | GCAGCGCCAATATCTGAACATAGCCAATTCAACTGCCGCTTCCAAAGATGTCCAGATTATGCGATGTCTGGA<br>GAAGAAGCTCAAGTACTTGCAACGGGAAAAGACGGAACTCAAAACCAAGCTTAAGGTTGCGTACGCTCCCTG<br>CCACGTTCGACGATACGATCGACAGGTTCAACTGGTGGAAGCCCACGTTCGCGTGCAGGATGATCTGGTCTT<br>GAAAATGAACGGCCTTCGAACGGAGATTCGTCACCTGGAATCGCAAATGAAGCGGCTCGATAAGGAGAGGAA<br>GGAGCTTCAGAAGGTTTCGCAGTCGGATTACTTCTTCTACAATCGGGTTACGAAAGCTAAGAAACGACTAGC<br>GACGTTGGAAGATCGATTGTATCACCTGAAGAAGCGGGAAGCT<br>(SEQ ID NO: 23) |
| AAEL007434 | CTGTCCTCGCCCAATGAATGGAACCGCAAAGAGGTTAAAAAACAACTTTCGGAGCGAGGTTATCTGATCGGG<br>CAATCCATCGGCGAGGGTTCCTACTCGAAGGTGTACTACTCGGAATACCGTAAATCAGGCCAACAGCAGCAT<br>TTCCCGGAACGGAGAGCATGCAAAATCATCAATCGAAACAAAAGTTCAATGGAGTATTCGCAGTTCCTTCCG<br>AGGGAGATCAAAACGATGATAGCGCTGTCCCATCCGAATATCGTTTCGGTTTATTCGGTGTTTGAATTTGGT<br>CCTTATGTTTGCATTTTCATGGATTATTGCCGGTGCGGAGATTTACTGCAG<br>(SEQ ID NO: 24) |
| AAEL010639 | GCGCACGTTATGATGGGAATTGGTTCAAGAACAAGCGCCACGGTGTAGGAAATTACGTTTTTAGCCGCGGAG<br>ATGTTACCTTGAAGGGAACATGGATCGAAGGAATCGCTCGCGGTCCCGCAGAGATCGTGTTTGAAGAGTATC<br>GGTTCCATGGATATTGGGATGTAGACAAACCCAGAGGTCCAGGTAGTTTCACTTTTGACGCCAAAGTTATGA<br>TCAGTGGAAAGTACTTCGTCGATGAGAAAGAGGGATGTGATGCAAGGGAA<br>(SEQ ID NO: 25) |
| AAEL011310 | GGATATGAGACCCGAACCGTTGTTCATCTTCGACCTGGGCGCTTCGGTGGGCGATGTCAAGTGGGCTCCATA<br>CTCCAGTACGGTGTTTGCGGCGGTCACAACCGAGGGCAAAGTGTTTGTATTCGACCTGAGCGTGAACAAGTA<br>CAAAGCGATTTGTGTGCAGGCGGTCGTCTCTAAGCGGAAGAACAAACTCTCTCGGATTGCCTTCAATCACAA<br>GCTACCGTTCATCATCGTCGGGGATGACAAGGGCACAACAATTACGCTCAAACTGTCGCCCAACCTGCGCAT<br>CAAGACGAAGGCACCGAAGAAAAC<br>(SEQ ID NO: 26) |
| CG4727 (bol) | GCGGATGGTGAATGCGTGGTACTAAGAGATCGGAAGCTGAACATTGCACCGGCCATCAAAAAGCAGCCCAAT<br>CCTCTGCAGTCAATTGTGGCCACAAACGGAGCCGTCTACTATACCACACGCGCCGGCACCGATCAGCAAT<br>ATACCCATGGATCAGTTCGCAGCCGCTGTATATCCGCCAGCCGCTGGAGTGCCAGCCATCTACCCACCTTCA<br>GCCATGCAATATCAGCCATTCATCAGTACTACAGTGTGCCAATGAATGTACCCACCATTTGGCCTCAGAAC<br>TACCAAGAAAACCATTCGCCATTGCTGCACTCGCCGACGTCAAACCCGCATTCGCCACACTCCCAGTCGCAT<br>CCACAATCCCCATGCTGGAG<br>(SEQ ID NO: 27) |
| CG3565 | CTGGAGAATGCCCGCTTCAACTACGTGTATATGAAGGACATTGCTCGCCTGGCAAAGGACTCGATCTTCTCG<br>CATAACGAGCTGATTAGCATTGTAATGCTCTACCATAAGTTTGTGCTGGTCAATGGGCCGAGAGCAAAGTAC<br>ATGACCATTCAGCAACTCTCTGCGCTGATGGAGCTCTTGTTTGAGATCGTGGATCGCGATCTCATTGCGACC |

TABLE 2-continued

| target mRNA encoded by coding region at Genbank No. | Exemplary dsRNA for use in silencing expression (only one strand shown). |
|---|---|
| | ATTGTGTATAGAATAGCCCATACACCAGGTTCCAGGCCTCCTGACTTCTTTTCCGACAAGCATATACACTTG<br>GAGTCCTTTGTGCGGCTTTTCACCGTATACTT<br>(SEQ ID NO: 28) |
| CG14271 (Gas8) | GCCTCAAGACGCGCAACACTCGGCTGGAAAAGAAGGTGAAGGGTCTCACTTGGGAGGCGGAAACTCTGATCC<br>TGCGCAACGACTCGCTGGTGGCAGAACGGGAGGGCCTGAAGGAGCGTTTCAACGACGTGATCGTCGAGCTGC<br>AGCAGAAGACAGGACTAAAGAATGTCCTTCTGGAGCGCAAGATTGCCGCATTGATGCGCGAGGATGAGAAGC<br>GCAGCATTGTCCTACACGAAACGATTGCCACCTGCGCTCCCAATTTCGCCGAAAAGTTAACCAGCTTGGATG<br>AACGGGTGGGCAAC<br>(SEQ ID NO: 29) |
| CG4568 (fzo) | CGCGGTGTCAGCGTTAAAAACCAAATTTGGTCCACACTTGCTAAGTGCGCAGAAGATTTTAAACCAGTTAAA<br>ATCAACTCTGATATGCCCTTTCATAGAGAAAGTAAGTCGTCTTATCGATGAGAATAAGGAGAGAAGAGCTAA<br>CTTGAATGCCGAAATAGAGGACTGGTTAATACTAATGCAAGAGGATAGAGAAGCGCTTCAATATTGTTTCGA<br>AGAACTGACTGAAATGACACAAAGAGTAGGTCGGTGCGTTTTGAACGACCAGATAAAAACGTTAATACCCTC<br>GTCTGTGCTATCATTCTCGCAACCATTTCACCCGGAATTCCCAGCACAAATAGGCCAGTAC<br>(SEQ ID NO: 30) |
| CG32396 (β-tub) | GCTTGACCTCTCTAATAATGGAGGCCCTGGTGGAGCAGTATCCGGATAATTTACTCTGCAACTATGTGACCA<br>TTCGGTCGCCGAATATGTCGCAGGTGGTTGTGGAACCCTATAATGCCCTACTTAGTACTCCCGCCTTGGTTA<br>ACAATTCGCATTTAACCTTCTGCCTTGATAACGAGGCACTGTTCCAAATCTGCAATAGAAACCTGAAGCTCA<br>AGATGTCCGGCTACGAGCACATTAACCACATAGTAGCCCTGACCATGTCGGGTATAACCACTTGCCTGCGGT<br>TTCCTGGCCAACTGAATGCTGGATTGCGCAAGATCTATGTAAATATGGTGCCATTCCCGCGGCTGCACTTCC<br>TCATACCGGGATTCGCACCATTGGTCACTTGCAAGCAGCAGCAGTTCAGCAAGGGTACCGTTTCGGAGCTGG<br>TGCAGCAGATCTTCTACAGTAATAATCTGCTCTGTGCCATCGATCTTCGAAAGGGCAAACTGCTGACCGCTG<br>CTGGAATTTTCCG<br>(SEQ ID NO: 31) |
| CG1S259 (nht) | TGCGAGCATCGAACAAGCTATCATCTGCACAACGACGAACGTTGTGTGATGAAGAACGATATGAGGGTCACG<br>ATGATGTTCCTCAACGATCTCGAGATTGCCGACTATGGATCATCGGATGACGAGACCGGCTTTTATCGCAAG<br>CGCCGGGCAGAGAACATCGACGAGGAGAGAAAGGTGGCTCGTCTGGAATCGGTGAATGATACGGCCTTGCTA<br>GCCATCTCCGGTCGAAAGCGCCCGGGAGAACAACTAGCCCCAGAATCTGCTCCAAGTGGTTCGAAAGTCGCC<br>AAATTGACCGGTGCTCCGAT<br>(SEQ ID NO: 32) |
| CG18369 (S-Lap5) | GCAACAAGCGCAAGCAGGATCGCACTCAGGTACCCAAACTGGATCTGTACGACTCACCGGATGTGGATGCCT<br>GGACGAGGGGTCTCTTCAAGGCGGAATCTCAGAACTTGGCTCGAAGATTGAGCGATTCGCCGGCTAATCAGA<br>TGACCCCCACCATATTCGCCCAATCGGCGGTGGATGCCCTGTGTCCGTCGGCGTTTCCGTGGAGGTGCGAT<br>CCATGGATTGGATAGAAATGAATCATCTCAATTCGTTTCTAATGATAGCCAAAGGCAGCTGCAGCCACCGG<br>TGGTCCTGGAGGTCAGCTACTGCGGCACAGCACCCGAGGATCGGCCCATTCTGCTGTTGGGCAAGGGTTTGA<br>CCTACAACAGTGGCGGATTGTGCCTGCGGCCAAAGGATTGCCTGCATATGTACCGCGGCTGCATGGCGGGAG<br>CAGCCCGTTTGTGTGGCCGCCGTTCGAGCTGCGGCAGCCCTTTCCCTGCCTGTAAACATCACGGCCGTACTGC<br>CGCTCTGCGAGAATATGCCATCGGG<br>(SEQ ID NO: 33) |
| CG17083 | TCGGTGAATCGCCTGTTTGAGGATATAGTTAACCTGAAAAAGGATAACTCCAACACGCTGCAGGACCAACTG<br>GATCAGATTTCCAGTCTGGAGAACAAGGTGCGTAACAAACAGGAATCCAACATGGAACTGCACAAGGCGCGG<br>GAAAACAACGATGCACGTTTGGAGAATCTTCTACAGGGCGTGGAGACGGTCTGCGAGATGTGTTCCATAGAT<br>GCCAGTCCGCTGACCAAACTCCTTGGTGACCACACCCACGTCAATCTGGTTAATGTCAATCGATTCTTGAAG<br>CTGCTCGAGACAAGGGTCCAGGAGCTGACGGCTAGTGTTT<br>(SEQ ID NO: 34) |
| CG9313 | GCCCACAACATGTCCGTCTATCGCATTGACTTCAATCGCTTCAACAGCAACATCTTCGTGTCCTGTGGCGCC<br>GACTGGATGGTCAAGGTGTGGGAGGATATGCGTCCAGATCCGCTGTTCATATTCGATCTTGGTGCCGCCGTT<br>GGCGATGTCAAGTGGGCACCTTACTCGAGCACCGTCTTCGCAGCGGTGACCACCGAGGGCAAGGTCCACGTT<br>TTCGACCTAAATGTGAATAAGTACAAGGCCATCTGCATCCAGGCCGTGGTGCCCAAGCGAAAGAACAAGCTC<br>ACCAGGTTATCCTTCAACGAGAAGCTCGCCTT<br>(SEQ ID NO: 35) |
| Aedes Dsx-F female-specific exons, DQ440532.1 and DQ440533.1 | GGTCAAGCCGTGGTCAATGAATACTCACGATTGCACAATCTGAACATGTTTGACGGTGTGGAGTTGCGCAGT<br>ACGACGCGCCAGTCCGGATGATAGACTTTTTACACGATCAGCACGACCCACTGCGCTGTGGCAAAGGTCGAA<br>CCGAAACAAGAATAAAGCACGAAGATCAGATGATCGATTTGACGGAAGAAGCAATCGAATACAAAGAAGAAT<br>CGGAACGAAGAAAACTCTAAAGCATCGCATATTTACAAAGCATAACGGAAAACCCGCAAGTTCAAACTAGTG<br>ATTAGTGTAAGATGAAGCAAAGCAGAAATGTGGTATGTAGATTTTTCGCGTTAGTTTACAAAGATAAGAAA<br>TGAGGTTGGACACACAATCGTGGGTATTCGTCTGAGTTCGTCACAACTGCACCGGAAACTGTGAAACAGAAT<br>AGAGCCAACCTGTGCGCGGAGAATGTTG<br>(SEQ ID NO: 36) |
| | GCAAATGCTGTTTAACGATAATAGCGACATGCAGCCATTCTGGGGCTACCACGTGTAGCTCTACTTGTGAGA<br>CAGCGTTCCTAAAGAGTGTGAAAGTGCAAACAAGTGATGAAACCAATAGTGCAAAGCAAGTTTAGAGGGAAA<br>ATTTAAAAAAATGCAAAACAGCAGTAGTACTTAACTTTTAAGATTGTGTTTCGAAAGCCGAAGTGTGTTCCA |

TABLE 2-continued

| target mRNA encoded by coding region at Genbank No. | Exemplary dsRNA for use in silencing expression (only one strand shown). |
|---|---|
| | TCTGCCACCGGAAAAAAACGACGACAGCAGAATCATCAACAAGCAACATCCATCCGAAAAAATCCGGGAAAC<br>CGGATCTTCAACCAACCATCCTACAATCTACAAACCAGAGATTATATCTCTTCAATCGTTTCCGACATCGGT<br>CGGTTTCGGTGCCCAAAATGATCTGATAAACACTTATCTCTCTGTAGCTTGCATGCCATTGCGAGCGTATTT<br>TGGTAGCTGGCCGTTGCCAAACGGCTCCGAC<br>(SEQ ID NO: 37) |

The skilled person will understand that a portion of each of the exemplary dsRNAs shown in Table 2 may be used to silence expression of a target mRNA, and that longer dsRNAs may also be used. Also understood by the skilled person is the ability to use other dsRNAs to silence expression of the target mRNAs disclosed in Table 2.

dsRNA polynucleotides useful in the methods described herein can be designed using methods that are routine and known in the art. For instance, candidate dsRNA polynucleotides that inhibit the expression of one of the mRNAs described herein may be identified using readily available algorithms. A candidate polynucleotide is the polynucleotide that is being tested to determine if it decreases expression of one of the coding regions described herein. The candidate polynucleotide can be identical to nucleotides located in the region encoding the polypeptide, or located in the 5' or 3' untranslated regions of the mRNA. Candidate polynucleotides may be screened using publicly available algorithms (e.g., BLAST) to compare the candidate polynucleotide sequences with coding sequences. Those that are likely to form a duplex with an mRNA expressed by a non-target coding region are typically eliminated from further consideration. The remaining candidate polynucleotides may then be tested to determine if they inhibit expression of a coding region.

In general, candidate polynucleotides are individually tested by introducing a candidate polynucleotide into a cell that expresses the appropriate polypeptide. In one embodiment, the candidate polynucleotides may be prepared in vitro and then administered to an insect, or to a cell that expresses the target mRNA. Methods for in vitro synthesis include, for instance, chemical synthesis with a conventional DNA/RNA synthesizer. Commercial suppliers of synthetic polynucleotides and reagents for such syntheses are well known. Methods for in vitro synthesis also include, for instance, in vitro transcription using a circular or linear vector in a cell free system. In one embodiment, the candidate polynucleotide may be administered as a dsRNA. In one embodiment, a candidate polynucleotide may also be administered to an insect, or to a cell that expresses the target mRNA, as a construct that encodes the candidate polynucleotide. Such constructs are known in the art and include, for example, a vector encoding and expressing a sense strand and an antisense strand of a candidate polynucleotide, and RNA expression vectors that include the sequence encoding the sense strand and antisense strand of a candidate polynucleotide flanked by operably linked regulatory sequences, such as an RNA polymerase III promoter and an RNA polymerase III terminator, that result in the production of an RNA polynucleotide.

A cell that can be used to evaluate a candidate polynucleotide may be a cell that expresses the appropriate target mRNA. A cell can be ex vivo or in vivo. As used herein, the term "ex vivo" refers to a cell that has been removed from the body of an insect. Ex vivo cells include, for instance, primary cells (e.g., cells that have recently been removed from an insect and are capable of limited growth in tissue culture medium), and cultured cells (e.g., cells that are capable of extended culture in tissue culture medium). As used herein, the term "in vivo" refers to a cell that is within the body of an insect.

Methods for introducing a candidate polynucleotide into a cell, including a vector encoding a candidate polynucleotide, are known in the art and routine. When the cells are ex vivo, such methods include, for instance, transfection with a delivery reagent, such as lipid or amine based reagents, including cationic liposomes or polymeric DNA-binding cations (such as poly-L-lysine and polyethyleneimine) Alternatively, electroporation or viral transfection can be used to introduce a candidate polynucleotide, or a vector encoding a candidate polynucleotide. When the cells are in vivo, such methods include, but are not limited to, feeding the candidate polynucleotide to an insect or soaking the insect in a composition that includes the candidate polynucleotide.

When evaluating whether a candidate polynucleotide functions to inhibit expression of a target mRNA described herein, the amount of target mRNA in a cell containing a candidate polynucleotide can be measured and compared to a control cell (e.g., the same type of cell that does not contain the candidate polynucleotide). Methods for measuring mRNA levels in a cell are known in the art and routine. Such methods include quantitative reverse-transcriptase polymerase chain reaction (RT-PCR). Primers and specific conditions for amplification of a target mRNA can be readily determined by the skilled person. Other methods include, for instance, Northern blotting, and array analysis.

Other methods for evaluating whether a candidate polynucleotide functions to inhibit expression of a polypeptide encoded by a target mRNA includes monitoring the polypeptide. For instance, assays can be used to measure a decrease in the amount of polypeptide encoded by the mRNA, or to measure a decrease in the activity of the polypeptide encoded by the mRNA. Methods for measuring a decrease in the amount of a polypeptide include assaying for the polypeptide present in cells containing a candidate polynucleotide and comparing to a control cell. Whether a cell expresses one of the polypeptides can be determined using methods that are routine and known in the art including, for instance, Western immunoblot, ELISA, immunoprecipitation, or immunohistochemistry.

In one embodiment, a candidate polynucleotide is able to decrease the expression of a target mRNA by at least 5%, at least 10%, at least 15%, at least 20%, at least 30%, at least 40%, at least 50%, at least 60%, at least 70%, at least 80%, at least 90% or 100% when compared to a control cell.

A dsRNA described herein can be encoded by a polynucleotide present in a vector. A vector is a replicating polynucleotide, such as a plasmid, phage, or cosmid, to which another polynucleotide may be attached so as to bring about the replication of the attached polynucleotide. Construction of vectors containing a polynucleotide described herein employs standard ligation techniques known in the art. See, e.g., Sambrook, 1989. A vector can provide for further cloning (amplification of the polynucleotide), i.e., a cloning vector, or for expression of the polynucleotide, i.e., an expression vector. The term vector includes, but is not limited to, plasmid vectors. A vector may result in integration into a cell's genomic DNA. Typically, a vector is capable of replication in a bacterial host, for instance *E. coli*. A polynucleotide described herein can be present in a vector as two separate complementary polynucleotides, each of which can be expressed to yield a sense and an antisense strand of the dsRNA, or as a single polynucleotide containing a sense strand, a loop region, and an anti-sense strand, which can be expressed to yield an RNA polynucleotide having a sense and an antisense strand of the dsRNA.

Selection of a vector depends upon a variety of desired characteristics in the resulting construct, such as a selection marker, vector replication rate, and the like. Suitable host cells for cloning or expressing the vectors herein are prokaryote or eukaryotic cells. Suitable prokaryotes include members of the domain Bacteria and members of the domain Archaea. In one embodiment, a suitable prokaryote is *E. coli*.

An expression vector optionally includes regulatory sequences operably linked to the polynucleotide of the present invention. Typically, the promoter results in the production of an RNA polynucleotide. Examples of such promoters include those that cause binding of an RNA polymerase, such as an RNA polymerase III complex, to initiate transcription of an operably linked polynucleotide of the present invention. In one embodiment, examples of such promoters include U6 and H1 promoters. A promoter may be constitutive or inducible. Another regulatory sequence is a transcription terminator. Suitable transcription terminators are known in the art and include, for instance, a stretch of 5 consecutive thymidine nucleotides.

The polynucleotide, such as a dsRNA, is administered to the insect. Methods for administering a dsRNA to an insect include, but are not limited to, administration by direct injection into an insect, administration by feeding, and administration by exposing the insect to conditions where dsRNA penetrates the cuticle (e.g., soaking the insect in a composition that includes one or more dsRNAs. The polynucleotide is present in a composition suitable for the chosen route of administration. Thus, a composition that is to be injected is formulated to be suitable for injection, for instance, isotonic with the recipient insect, and the like. A composition that is to be used for administration by soaking is suitable for maintaining the viability of the insect. An example of such a composition is an aqueous solution that is free of chlorine and pesticides. A dsRNA may be administered to an insect at the larva stage, the pupa stage, or the adult stage The polynucleotide may be complexed with a compound suitable for the chosen route of administration. For example, a polynucleotide may be associated with nanoparticles (see, for instance, Zhu et al., US Published Patent Application 2013/0137747), and/or other compounds that promote the uptake of a polynucleotide by a cell (see, for instance, Whyard et al., US Published Patent Application 2013/0237586). In one embodiment, the polynucleotide is present in solid form that is fed to an insect. Different solid forms may be used depending upon the insect that is to be targeted, and the use of different solid forms is known to the skilled person and routine. In one embodiment, the solid form is a cell. The cell may be any cell that will be ingested by the insect and that can be engineered to express the dsRNA. The cell may be a prokaryotic cell or a eukaryotic cell. Examples of prokaryotic cells include members of the domain Bacteria and members of the domain Archea. One example of a Bacteria is the routinely used host cell *Eschericia coli*, and another example is *Pseudomonas* spp. Examples of eukaryotic cells include, but are not limited to, unicellular microbes such as yeasts, such as *Saccharomyces cerevisiae*, and plant cells. Other solid forms that may include the dsRNA and be fed to an insect are routinely used during laboratory culture of insects and are readily available. In one example, a cell is combined with a nutrient source and a matrix, such as agar or other gelatinous substance, which is then fed to an insect, such as a larva. An example of a composition that includes a cell having a dsRNA, a nutrient source, and an agar is disclosed in Example 1. In one embodiment, a dsRNA combined with a nutrient source and a matrix is not present in a cell. Also provided herein is a cell that includes a dsRNA disclosed herein.

A cell that is fed to an insect may be capable of replication or may be inactivated, i.e., incapable of replication. A cell may be inactivated in any way, provided the dsRNA in the inactivated cell remains biologically active, e.g., does not lose the ability to silence a target coding region. Methods for inactivation of a cell are known in the art and routine, and include, for instance, heat, high pressure, antibiotics (bacteriostatic or bacteriocidal), and the like.

The dosage administered to an insect is sufficient to result in decreased expression of the polypeptide encoded by the target mRNA. Such dosages can be easily determined by the skilled person. In one embodiment, when the dsRNA is injected, the concentration of dsRNA is, is at least, or is no greater than, 0.01 milligrams/milliliter (mg/ml), 0.05 mg/ml, 0.1 mg/ml, 0.5 mg/ml, or 1 mg/ml. In one embodiment, when more than one mRNA is injected the concentration of the combined dsRNAs is, is at least, or is no greater than, 0.01 milligrams/milliliter (mg/ml), 0.05 mg/ml, 0.1 mg/ml, 0.5 mg/ml, or 1 mg/ml. In one embodiment, the volume injected is, is at least, or is no greater than, 5 nanoliters (nl), 10 nl, 15 nl, 20 nl, or 25 nl. An insect may be injected once, or more than once. In one embodiment, an insect may be injected at different developmental stages.

In one embodiment, when the dsRNA is administered by soaking the insect, the concentration of dsRNA in the aqueous solution is, is at least, or is no greater than, 0.01 mg/ml, 0.05 mg,/ml, 0.1 mg/ml, 0.5 mg/ml, or 1 mg/ml. In one embodiment, when more than one mRNA is present, the concentration of the combined dsRNAs is, is at least, or is no greater than, 0.01 milligrams/milliliter (mg/ml), 0.05 mg/ml, 0.1 mg/ml, 0.5 mg/ml, or 1 mg/ml. The insect may be exposed to the dsRNA continuously or for shorter periods. In one embodiment, the insect is exposed to the solution with the dsRNA(s) for, for at least, or for no greater than, 30 minutes, 1 hour, or 2 hours each day. In one embodiment, the exposure is for, for at least, or for no greater than, 1, 2, 3, 4, 5, or 6 days. In one embodiment, the insect is a larva or a pupa and exposure is for each day of that developmental stage.

In one embodiment, when the dsRNA is administered by feeding it to the insect, the insect is fed the composition 1 or more times each day. In one embodiment, the exposure is for, for at least, or for no greater than, 1, 2, 3, 4, 5, or 6 days. In one embodiment, the insect is a larva and exposure is for each day of that developmental stage.

In one embodiment, more than one dsRNA may be administered to an insect. For instance, an insect may be injected more than once with separate compositions, each of which contain one type of dsRNA, or injected once with a composition that includes different types of dsRNAs. Likewise, an insect may be fed a composition that includes different microbes, each of which contains one type of dsRNA, or may be fed a single microbe that has been engineered to include more than one type of dsRNA. When more than one dsRNA is administered to an insect, the different types of dsRNAs may target the same mRNA or different mRNAs. Some combinations of dsRNAs that target different mRNAs are synergistic in the effect they have on reducing fertility, reducing fecundity, and/or increasing male bias. Examples of combinations that are synergistic are shown in Table 14. It was also found that dsRNAs that not reduce fertility and/or fecundity when used alone can result in significant reductions of fertility and/or fecundity when used with other dsRNAs. For instance, dsRNAs directed to AAEL001156, AAEL002084, AAEL006841, AAEL007544, AAEL011098, AAEL012096, or AAEL014408, when used in combination with other dsRNAs, resulted in a synergistic effect (Table 14).

Also provided herein is a modified insect, including, but not limited to, a modified insect produced by the methods disclosed herein. The insect may be a larva, a pupa, or an adult. In one embodiment, the modified insect is male. In one embodiment, a modified insect has the phenotype of decreased fecundity, decreased fertility, or the combination thereof, compared to a control. Optionally, the modified insect has no significant alteration in competitiveness compared to a control.

Also provided herein is a population of modified insects. The insects of the population may be a larva, a pupa, adult, or a combination thereof. The population has decreased fecundity, decreased fertility, or the combination thereof, compared to a control population. Optionally, the modified insect has no significant alteration in competitiveness compared to a control. In one embodiment, the population includes adults that are male biased. For instance, the population is, is at least, or is no greater than 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 100% male. Further provided are methods for making a population of modified insects, including making a population that is male biased. In one embodiment, a population of modified insects may be produced by mass breeding in a containment facility. In one embodiment, a population of modified insects may be produced by exposing insects in an environment to one or more polynucleotides, such as a dsRNA. For instance, insects in a natural environment may be exposed to a dsRNA by adding dsRNA to baited food that is present in a natural environment. Insects, such as insects at the larval stage, ingest the baited food and the dsRNA. A composition that includes a food substance to act as a bait may also include an attractant, such as a pheromone, to attract insects. The size of a population of insects is not intended to be limiting, and may be, for instance, at least 100, at least 10,000, at least 100,000, or at least 1 million modified insects.

Also provided are methods of using the modified insects described herein, In one embodiment, a method is directed to biological control of an insect. Biological control refers to decreasing the population of a target insect in a defined area, and includes controlling reproduction in a population of the target insect. The area may be a laboratory setting, or a natural environment. The method includes releasing into an environment a population of modified insects. The method results in a reduction of the number of viable progeny of the insect in the environment, thereby causing a reduction in the numbers of the insect in the environment. The method may result in the elimination, suppression, containment, or prevention of a target insect in a defined area.

The environment may be any location where the target insect is present. The insects that are released may be in any developmental stage, e.g., larval, pupal, or adult, or a combination thereof. In one embodiment, the released insects are adults. Methods for releasing insects into environments for use in biological control, such as sterile insect technique methods, may vary depending on the insect, and are known in the art and routine. Alternatively, baited food may be used in a natural environment.

In one embodiment, the insect (for instance, *Aedes aegypti*) is fed double-stranded RNA (dsRNA), and the ingested dsRNA induces gene-specific RNA interference (RNAi), reducing the expression of one or more targeted genes, rendering the males sterile. In addition, the insects may be simultaneously fed dsRNA that targets a female-specific gene, thereby inhibiting female development. As described in the Example, combinations of dsRNAs resulted in the production of male-only mosquitoes, and when tested in mating competitions with fertile males, the sterilized males were highly effective in reducing the population of mosquitoes. An extensive search for male-reproduction genes found that not all genes, when targeted by RNAi, would render the males sterile, and others failed to leave the males able to compete for female mates.

Also provided herein is the observation that feeding the insects dsRNA during their larval development can induce sterility in the adult. This result was unexpected and surprising; in many insects, gene silencing following ingestion of a dsRNA may be more pronounced in gut tissues, and silencing beyond the gut may be considerably reduced if non-existent. This result demonstrates that the RNAi phenotype can persist during the insect's development, and that the dsRNA can reach the gonad to induce the desired phenotype.

This method of producing sterile, male-only insects is an improvement over other existing methods where sex-sorting is challenging (such as when irradiating or treating with chemosterilants), and is an improvement over the use of genetically-modified insects, where the potential of spreading the transgene into non-target populations is a concern.

The present invention is illustrated by the following examples. It is to be understood that the particular examples, materials, amounts, and procedures are to be interpreted broadly in accordance with the scope and spirit of the invention as set forth herein.

EXAMPLE 1

To produce sterile insects without the use of radiation, non-specific chemosterilant compounds, or transgenic insects, a method of sterilizing insects using orally-administered double-stranded RNA (RNA) delivered to the larval stages of the insects was developed. In this invention, several genes are identified, that when targeted by RNAi, can sterilize male insects. Until this study, it was not clear whether ingested dsRNAs would be effective in silencing genes in all tissues beyond the gut, and in particular, the gonads of the insects. In addition to silencing genes associated with male (and female) fertility, it was also determined that the sex-ratio can be altered by feeding larvae with dsRNA targeting the female variant of the doublesex gene, which is involved in sex differentiation. Combining both testis-specific and female-specific dsx dsRNAs, it was possible to produce a population of mosquitoes that were almost entire male and either fully sterile or with severely reduced fecundity. It was also found that these dsRNAs could be expressed in bacteria, and that feeding the live or heat-killed bacteria to the mosquitoes had the same effect.

Results

1. Testis-Specific Genes are Identified in the Mosquito *Aedes Aaegypti*.

Using a suppressive subtractive hybridization technique (see Methods), 37 genes were identified that are predominantly or exclusively expressed in male *Aedes aegypti* testes (Table 3). Despite having been assigned accession numbers in VectorBase (available through the World Wide Web), the function and the tissue-specific expression of these genes had not previously been determined in the mosquito. RT-PCR continued that all 37 genes are expressed in testes in this species, with 15 genes showing no evidence of expression in larval stages, other adult male tissues, nor in female ovaries. Using bioinformatics searches, putative homologues for all but three of the 37 genes were found in the sequenced genomes of some other insects, including the model species *Drosophila melanogaster* (Table 3).

TABLE 3

Genes expressed predominantly or strictly in the testis of *A. aegypti* genes. Genes were identified in a SSH screen, selectively amplifying genes expressed in testes relative to the rest of the male's body. RT-PCR was used to assess whether the genes showed any expression in other male tissues, in late instar larvae, or in female ovaries. Genes are ordered in ascending gene accession numbers.

| Aedes aegypti accession # | D. melanogaster homologue | Testis-specificity | Expressed in larvae? | Expressed in ovary? |
|---|---|---|---|---|
| AAEL001033 | CG8208 (MDB-like) | No | Yes | Yes |
| AAEL001156 | CG5280 | Yes | No | No |
| AAEL001684 | CG4727 (bol) | Yes | No | No |
| AAEL002084 | CG14220 | Yes | No | Yes |
| AAEL002275 | CG3565 | Yes | No | No |
| AAEL003501 | CG10252 | Yes | Yes | No |
| AAEL003757 | CG4434 | No | Yes | No |
| AAEL004231 | CG14271 (Gas8) | Yes | No | No |
| AAEL004471 | CG4568 (fzo) | Yes | No | No |
| AAEL004696 | CG5737 | No | Yes | No |
| AAEL004939 | CG32396 (β-tub) | Yes | No | No |
| AAEL005010 | CG14305 | Yes | No | No |
| AAEL005975 | CG15259 (nht) | Yes | No | No |
| AAEL006726 | CG6647 (zpg) | Yes | No | Yes |
| AAEL006841 | — | Yes | No | Yes |
| AAEL006975 | CG18369 (S-Lap5) | Yes | No | No |
| AAEL007144 | CG12423 (klhl10) | No | No | No |
| AAEL007188 | CG17083 | Yes | No | No |
| AAEL007434 | — | Yes | No | No |
| AAEL007544 | CG10895 (lok) | Yes | No | Yes |
| AAEL007684 | CG4767 (tek) | No | Yes | No |
| AAEL008428 | CG10841 | No | No | No |
| AAEL008678 | CG18190 | No | Yes | Yes |
| AAEL009047 | CG8819 (achi) | No | Yes | Yes |
| AAEL009321 | — | No | Yes | Yes |
| AAEL009357 | CG2146 | No | Yes | Yes |
| AAEL009553 | CG12813 | No | Yes | No |
| AAEL010639 | CG5458 | Yes | No | No |
| AAEL011098 | CG8362 | Yes | No | Yes |
| AAEL011310 | CG9313 | Yes | No | No |
| AAEL012096 | CG18472 | Yes | No | No |
| AAEL012446 | CG6303 | No | Yes | Yes |
| AAEL013621 | CG17564 | Yes | Yes | No |
| AAEL013723 | CG31000 (heph) | Yes | Yes | Yes |
| AAEL013737 | CG6971 | Yes | No | No |
| AAEL014067 | CG5048 | Yes | Yes | No |
| AAEL014408 | CG4965 (twe) | Yes | No | Yes |

2. RNAi of the Testis-Specific Genes Rendered the Males Sterile or Poorly Fertile.

Using in vitro transcription, double-stranded RNAs were prepared for all 15 testis-specific genes and were injected into male pupae. QRT-PCR confirmed that RNAi was induced in the insects, with knockdown of transcripts ranging between 40 to 94% of control levels (controls were males injected with a non-mosquito-specific gus-dsRNA). Knockdown of all of the 15 targeted genes resulted in sterile or very weakly fertile males (Table 4). Not all dsRNAs, however, were equally effective; some induced high levels of RNAi and had greater impacts on male fertility, whereas other dsRNAs had weaker RNAi effects and lesser impacts on fertility or fecundity. In total, 12 dsRNAs induced sterility in greater than 50% of the treated males, lower (<50% of controls) fecundity of the males, or both high sterility frequencies and low fecundities.

TABLE 4

RNAi-mediated knockdown of some testis-specific genes resulted in increased sterility frequencies and reduced fecundities in male mosquitoes. The potential suitability of the genes to serve as RNAi targets for SIT was assessed by noting whether fecundity was reduced more than 50% (+), sterility was induced in more than 50% of the males (+), or both (++).

| A. aegypti accession # | % RNAi[1] | % sterility[2] | % fecundity[3] | Suitability as a target |
|---|---|---|---|---|
| Gus (negative control) | 0 | 0 | 100 | — |
| AAEL001156 | 48 ± 14 | 18 ± 6 | 84 ± 8 | |
| AAEL001684 | 90 ± 5 | 71 ± 5 | 5 ± 3 | ++ |
| AAEL002275 | 75 ± 4 | 59 ± 9 | 26 ± 5 | ++ |
| AAEL004231 | 94 ± 5 | 72 ± 6 | 8 ± 6 | ++ |
| AAEL004471 | 84 ± 7 | 62 ± 4 | 11 ± 5 | ++ |
| AAEL004939 | 74 ± 8 | 48 ± 9 | 32 ± 9 | + |
| AAEL005010 | 77 ± 7 | 36 ± 8 | 43 ± 12 | + |
| AAEL005975 | 72 ± 3 | 49 ± 7 | 28 ± 10 | + |
| AAEL006975 | 91 ± 3 | 72 ± 8 | 8 ± 4 | ++ |
| AAEL007188 | 80 ± 5 | 57 ± 10 | 22 ± 4 | ++ |
| AAEL007434 | 48 ± 9 | 16 ± 5 | 54 ± 7 | + |
| AAEL010639 | 40 ± 11 | 38 ± 5 | 44 ± 13 | + |
| AAEL011310 | 52 ± 12 | 32 ± 9 | 44 ± 6 | + |
| AAEL012096 | 46 ± 11 | 18 ± 4 | 92 ± 7 | |
| AAEL013737 | 42 ± 4 | 10 ± 5 | 89 ± 8 | |

[1]RNAi assessed using qRT-PCR from three samples of pooled RNA derived from groups of 5 insects.

[2]Percent sterility based on three trials of 10 insects, with each dsRNA-injected insect offered two virgin mates; individuals were considered sterile if no viable eggs were produced over a 1 week period.

[3]Percent fecundity of those individuals that produced viable eggs was calculated relative to three control matings between gus-dsRNA-injected individuals and virgin mates, which produced 43 ± 5 viable eggs/female by day 7, post-mating.

3. RNAi of Gonad-Specific Genes Rendered Both Males and Females Sterile or Poorly Fertile.

Using in vitro transcription techniques, dsRNAs were prepared for 6 genes that were identified as being expressed in both testes and ovaries, and following injection into pupae, both male and female insects were rendered sterile or with significantly reduced fecundity, relative to insects injected with dsRNA specific to the bacterial gus gene (Table 5).

TABLE 5

Impact of dsRNA injections into pupae on male or female fertility or fecundity. Values represent the means and standard errors of three replicate experiments.

| | males | | | females | | |
|---|---|---|---|---|---|---|
| Gene | % RNAi[1] | % sterile[2] | % fecundity of fertile individuals[3] | % RNAi[1] | % sterile[2] | % fecundity of fertile individuals[3] |
| AAEL002084 | 44 ± 7 | 23 ± 7 | 36 | 56 ± 9 | 28 ± 9 | 26 |
| AAEL006726 | 85 ± 8 | 53 ± 9 | 15 | 75 ± 6 | 36 ± 12 | 19 |
| AAEL006841 | 74 ± 6 | 43 ± 12 | 18 | 88 ± 6 | 47 ± 7 | 18 |
| AAEL007544 | 42 ± 7 | 26 ± 3 | 32 | 37 ± 5 | 50 ± 3 | 26 |
| AAEL011098 | 48 ± 6 | 36 ± 3 | 26 | 56 ± 4 | 56 ± 3 | 8 |
| AAEL014408 | 91 ± 5 | 76 ± 3 | 12 | 87 ± 5 | 80 ± 1 | 32 |

[1]RNAi assessed using qRT-PCR from three samples of pooled RNA derived from groups of 5 insects.
[2]Percent sterility based on three trials of 10 insects, with each dsRNA-injected insect offered two virgin mates; individuals were considered sterile if no viable eggs were produced over a 1 week period.
[3]Percent fecundity of those individuals that produced viable eggs was calculated relative to three control matings between gus-dsRNA-injected individuals and virgin mates, which produced 43 ± 5 viable eggs/female by day 7, post-mating.

4. RNAI of Some Testis-Specific Genes Also Reduced Competitive Ability of the Males.

Of the 15 testis-specific dsRNAs tested in the mosquito *Aedes aegypti*, some negatively affected male mating behaviour, while others had minimal or no negative impact on male mating fitness. Of the 15 genes examined, 3 significantly reduced the males' mating competitiveness, 3 slightly reduced male mating competitiveness, while the other 10 dsRNAs produced high percentages of sterile males that could effectively compete for female mates and thus reduce the number of progeny produced in the next generation (Table 6). These 10 dsRNAs targeted genes that represent strong candidates for further screening to identify suitable RNAi targets to produce sterile males for SIT applications in this species.

TABLE 6 dsRNA-injected males are competitive with fertile males and can reduce the number of progeny in the next generation. Five dsRNA-treated males were mixed with 5 untreated males and 10 virgin females. One week later, eggs were collected and hatched to assess the next generation population size. The values represent the means and standard errors of three replicate experiments. Male pupae injected with gus-dsRNA served as the negative controls and the maximal population size expected. A strong negative impact on mating competitiveness was indicated if the population size was not reduced by more than 10% and a partial negative impact was indicated if the population was not reduced by more than 20%.

| RNAi-targeted gene | Viable progeny | % population reduction[1] | Negative impact on competitiveness? |
|---|---|---|---|
| Gus (control) | 153.3 ± 5.7 | — | — |
| AAEL001156 | 151.3 ± 14.7 | 1 (ns) | yes |
| AAEL001684 | 90.7 ± 16.7 | 41 (P < 0.01) | no |
| AAEL002275 | 97.7 ± 5.2 | 36 (P < 0.01) | no |
| AAEL004231 | 85.3 ± 7.1 | 44 (P < 0.01) | no |
| AAEL004471 | 85.0 ± 13.5 | 44 (P < 0.01) | no |
| AAEL004939 | 100.0 ± 7.8 | 35 (P < 0.01) | no |
| AAEL005010 | 145.3 ± 11.0 | 5 (ns) | yes |
| AAEL005975 | 98.0 ± 13.3 | 35 (P < 0.01) | no |
| AAEL006975 | 101.3 ± 11.8 | 34 (P < 0.01) | no |
| AAEL007188 | 106.0 ± 7.5 | 31 (P < 0.01) | no |
| AAEL007434 | 125.3 ± 6.6 | 19 (P < 0.01) | partial |
| AAEL010639 | 136.7 ± 2.7 | 11 (P < 0.05) | partial |
| AAEL011310 | 91.7 ± 8.0 | 41 (P < 0.01) | no |
| AAEL012096 | 144.0 ± 9.4 | ns | yes |
| AAEL013723 | 127.0 ± 4.3 | 17 (P < 0.05) | partial |
| AAEL006726 | 101.2 + 12.1 | 34 (P < 0.01) | no |
| AAEL014408 | 146 + 11.8 | ns | yes |

[1]Population sizes were compared to the gus-dsRNA-treated controls, and values were compared using student t-tests.

5. RNAi of the Homologous Genes in *D. Melanogaster* Also Induced Sterility, and Some Had Limited or No Negative Effects on Male Mating Competitiveness.

*D. melanogaster* larvae were injected with dsRNAs corresponding to 9 of the previously identified 10 candidate mosquito genes (in section 4). RNAi was induced for all dsRNAs injected, and 6 of the 9 dsRNAs significantly reduced fecundity (by more than 30%) sterility, and 4 of the 6 still enabled the males to compete with fertile males for mates (population was reduced by >30% after one generation; Table 7). These findings suggest that several of the candidate genes could also serve as potential SIT targets in other insect species.

TABLE 7

RNAi of testes genes in *D. melanogaster* produce sterile males that are competing for mates.

| *Aedes aegypti* accession # | *D. melanogaster* homologue | % RNAi in *Drosophila* adults[1] | Reduced fertility or fecundity?[2] | % reduction of next generation[3] |
|---|---|---|---|---|
| AAEL001684 | CG4727 (bol) | 48 | Yes | 32 |
| AAEL002275 | CG3565 | 77 | No | 6 (ns) |
| AAEL004231 | CG14271 (Gas8) | 49 | Yes | 38 |
| AAEL004471 | CG4568 (fzo) | 58 | Yes | 30 |

TABLE 7-continued

RNAi of testes genes in *D. melanogaster* produce sterile males that are competing for mates.

| Aedes aegypti accession # | D. melanogaster homologue | % RNAi in Drosophila adults[1] | Reduced fertility or fecundity?[2] | % reduction of next generation[3] |
|---|---|---|---|---|
| AAEL004939 | CG32396 (β-tub) | 43 | No | 4 (ns) |
| AAEL005975 | CG15259 (nht) | 86 | Yes | 38 |
| AAEL006975 | CG18369 (S-Lap5) | 72 | No | 2 (ns) |
| AAEL007188 | CG17083 | 66 | Yes | 6 (ns) |
| AAEL011310 | CG9313 | 58 | Yes | 22 |

[1]Values represent the reduction in targeted gene expression based on RNA derived from 10 pooled males.
[2]Ds-RNA-treated males were mated to two virgin females, and the number of progeny produced was compared to gus-dsRNA-treated males. A male's fertility/fecundity was assessed as being reduced if there were more than 30% fewer progeny than the controls (Chi square, P < 0.05). While the cut-off for a suitable reduction in fertility or fecundity was considered 30%, all these testes genes targeted in *D. melanogaster* resulted in a statistically significant reduction of fertility or fecundity.
[3]Five dsRNA-treated males were mixed with five untreated males and 5 females. A reduction in the production of viable adult progeny of greater than 30% was considered significant, relative to control mating with 10 fertile males (ANOVA, P < 0.05). While 30% was considered significant, most of these testes genes targeted in *D. melanogaster* resulted in a reduction offspring in the next generation, except those indicated by "ns", denoting no significant difference from fecundity values relative to the negative controls.

6. Feeding Mosquito Larvae dsRNAs Can Render the Insects Sterile as Adults.

Mosquito larvae were treated with several formulations of ingestible dsRNAs targeting the testes genes. Daily 1 h exposures (for 5 days) of larvae to dsRNA dissolved in water induced partial sterility and reduced fecundity in males treated with seven of the top ten dsRNAs identified as having significant impacts on fertility (Table 8). *E. coli* bacteria expressing hairpin dsRNAs were fed continuously to larvae, either live or heat-killed. Using either live or dead bacteria, three of the dsRNAs were effective at inducing full sterility in many males, and significantly reduced fecundity in remaining males. No significant loss of potency of the RNAi effect was observed when the bacteria were heat-killed and mixed into mosquito feeding formulations. This demonstrates that is possible to mass-produce large quantities of the dsRNA using bacteria, and that the RNAi effect is sustained into adulthood. It also highlights the value of using bacteria to produce the dsRNA cheaply and in a form that is both attractive to the feeding larvae and effective in inducing RNAi.

TABLE 8

Feeding dsRNA to mosquito larvae can induce sterility and reduced fecundity in male mosquitoes. The values represent the means and standard errors of three replicates of 10 males mated to two females.

| | dsRNA in water | | Live *E. coli* expressing dsRNA | | Dead *E. coli* expressing dsRNA | |
|---|---|---|---|---|---|---|
| | % sterile[1] | % fecund[2] | % sterile | % fecund | % sterile | % fecund |
| AAEL001684 | 27 ± 5 | 32 ± 4 | 54 ± 8 | 12 ± 7 | 56 ± 8 | 18 ± 4 |
| AAEL002275 | 14 ± 3 | 73 ± 8 | 16 ± 5 | 66 ± 9 | 24 ± 7 | 54 ± 6 |
| AAEL004231 | 36 ± 5 | 33 ± 6 | 85 ± 5 | 12 ± 8 | 90 ± 4 | 10 ± 6 |
| AAEL004471 | 24 ± 5 | 23 ± 10 | 77 ± 4 | 18 ± 4 | 83 ± 6 | 12 ± 4 |
| AAEL004939 | 22 ± 7 | 76 ± 3 | 28 ± 5 | 77 ± 7 | 58 ± 6 | 66 ± 6 |
| AAEL005975 | 46 ± 6 | 34 ± 3 | 86 ± 6 | 8 ± 6 | 77 ± 5 | 10 ± 5 |
| AAEL006726 | 34 ± 6 | 53 ± 4 | 55 ± 6 | 26 ± 5 | 52 ± 4 | 27 ± 4 |
| AAEL006975 | 8 ± 5 | 96 ± 3 | 14 ± 8 | 77 ± 8 | 20 ± 4 | 32 ± 5 |
| AAEL007188 | 2 ± 2 | 101 ± 5 | 0 ± 0 | 98 ± 2 | 5 ± 2 | |
| AAEL011310 | 12 ± 4 | 86 ± 8 | 10 ± 4 | 95 ± 2 | 10 ± 5 | |

[1]Percent sterility represents the percentage of males that were completely sterile (no viable progeny) following mating with two virgin females.
[2]Percent fecundity refers to the number of viable progeny of the remaining fertile males, relative to the number of progeny derived from control males (gus-dsRNA-injected), mated to two virgin females each.

Increased concentrations of dsRNA enhanced the sterilization effect of dsRNAs (Table 9). RNAi is known to be dose dependent, and efficacy of RNAi can be enhanced by increasing the concentration of dsRNA in the water treatments.

TABLE 9

Higher sterilization rates can be achieved by increasing the concentrations of dsRNA within the water. Larvae were exposed to the dsRNAs each day for 1 h, and the males that developed were provided virgin females to test their fertility.

| | % sterility using dsRNA in water | |
|---|---|---|
| dsRNA | 0.02 mg/ml | 0.2 mg/ml |
| AAEL001684 (bol) | 24 ± 5 | 86 ± 6 |
| AAEL004231 (gas8) | 35 ± 5 | 92 ± 5 |
| AAEL004471 (fzo) | 29 ± 5 | 82 ± 5 |
| AAEL005975 (nht) | 30 ± 6 | 84 ± 5 |
| AAEL006726 (zpg) | 20 ± 5 | 72 ± 5 |

Increased sterilization rates could also be achieved by combining two different dsRNAs, targeting different genes. This phenomenon was observed when mosquitoes were either exposed to dsRNA in the water or were fed *E. coli* expressing two different dsRNAs (Table 10). Comparing sterilization rates noted in Table 9 with values in Table 10, it is clear that sterilization can be enhanced, even using lower concentrations of dsRNA of each dsRNA (e.g. 0.01 mg/ml). Even dsRNAs that alone had not been particularly potent at inducing RNAi were much more effective when mixed with another dsRNA, indicating that combinations of dsRNA could be an effective way of improving sterilization efficiency.

TABLE 10

Combinations of dsRNAs enhance sterilization effect. Mosquito larvae were either soaked daily for 1 hr in two dsRNAs (each at 0.01 mg/ml, combined to yield 0.02 mg/ml) or were fed continuously on equal concentrations of two E. coli strains.

| dsRNA(s) | % sterility Soaking in dsRNA (0.02 mg/ml total) | E. coli feeding (dead bacteria) |
|---|---|---|
| AAEL001684 + AAEL002275 | 46 ± 5 | 77 ± 6 |
| AAEL001684 + AAEL004231 | 79 ± 6 | 92 ± 6 |
| AAEL006726 + AAEL004231 | 72 ± 9 | 84 ± 7 |
| AAEL006975 + AAEL006726 | 44 ± 6 | 68 ± 10 |
| AAEL005975 + AAEL004231 | 88 ± 9 | 94 ± 5 |

7. Feeding Mosquito Larvae dsx$^F$-dsRNA Inhibited Development of Female Mosquitoes.

Doublesex is a sex-differentiation gene that is differentially spliced in male and female insects. The female splice variant of dsx produces DSX$^F$, which acts as a transcription factor that controls expression of many female-specific genes in insects. In contrast, DSX™, the protein derived from the male-specific splice variant, coordinates expression of male-specific genes. RNAi-mediated knockdown of dsx$^F$ in mosquitoes was achieved by delivering two dsRNAs targeting the female-specific exons of dsx, either by soaking the insects in the two combined dsRNAs or by feeding equal concentrations of the two dsRNA-expressing E. coli strains, each targeting the two different dsx$^F$ sequences. The dsx$^F$ dsRNA inhibited development of adult females, and feeding dsx$^F$ dsRNA resulted in a strongly male-biased population of insects (Table 11). Although some females still developed, their fertility was well below average; inspection of their spermatheca after being provided male mates for one week showed no evidence of sperm in most females, which indicates that they had not attempted to mate. Interestingly, when offered blood meals, only one of the dsx$^F$-dsRNA treated females attempted to blood feed. These results suggest that if mosquito larvae are fed dsx$^F$-dsRNA, the few females that develop from the cultures should not reduce the mating efficiency of sterilized males, and should not pose significant health risks.

TABLE 11

Treatment of mosquitoes with dsxF-dsRNA results in significantly reduced numbers of females and all females are sterile.

| dsRNA | dsRNA delivery | # larvae treated[2] | # females developed | # females that bloodfed | # females that produced progeny[3] |
|---|---|---|---|---|---|
| gus | Daily soakings | 420 | 207 | 162 | 139 |
| dsxF | Daily soakings | 440 | 6 | 0 | 0 |
| gus | Larval feeding[1] | 445 | 238 | 194 | 172 |
| dsxF | Larval feeding[1] | 460 | 7 | 1 | 0 |

[1]larvae were fed heat-killed E. coli continuously
[2]mixed sexes of larvae were treated
[3]females were provided 2 males for a period of one week, offered bloodmeals, and hatching of eggs monitored.

8. Feeding Mosquito Larvae a Mixture of E. coli That Expressed Both dsxF-dsRNA and a Testis-Specific-dsRNA Produced Mostly Male Mosquitoes, All of Which Were Either Sterile or Had Significantly Reduced Fertility.

Two E. coli strains were mixed, one expressing dsRNA targeting the female-specific dsxF transcript, the other expressing dsRNA targeting the AAEL004231 transcript. These were mixed with a feeding formulation (see Methods) to feed the mosquito larvae continuously. The adults that were produced were sexed and provided mates to assess their fertility (produced any offspring?) and fecundity (number of offspring). The insects fed on these E. coli developed almost entirely as males (96% males), indicating that the majority of females had failed to develop due to silencing of the dsxF transcripts (Table 12). The vast majority (96%) of the males were sterile, and of those males that were fertile, they produced less than 1% of the progeny produced by the control treatments, which were fed gus-dsRNA. Of the few females that were produced, their fecundity was reduced to 11% of the control females.

TABLE 12

Mosquito larvae fed on E. coli expressing dsRNA specific to dsxF and AAEL004231 developed into sterile male mosquitoes. Control larvae were raised on gus-dsRNA-expressing bacteria. The values represent the means and standard errors for four replicates of 50 larvae.

| dsRNA target | % males[1] | % males sterile[2] | Progeny/male[3] | % female fertility[4] |
|---|---|---|---|---|
| Gus | 52 ± 3 | 2 ± 1 | 62 ± 7 | 94 ± 2 (35 ± 4) |
| dsxF + AAEL004231 | 96 ± 2 | 96 ± 3 | 0.42 ± 0.04 | 4 ± 1 (4 ± 2) |

[1]The percentage of mosquitoes that developed into males after 8 days development
[2]The percentage of males that produced no progeny after being provided two virgin females for a period of 1 week.
[3]The average number of progeny produced in 1 week by the dsRNA-treated males after mating with two females.
[4]Percentage of females that was fertile after being fed the dsRNA as larvae. Numbers in parentheses indicate the number of progeny that each female produced over a one week period.

9. Mixing dsRNA-Fed Mosquitoes With Untreated Mosquitoes Results in Rapid Population Declines.

Mosquitoes derived from cultures fed on E. coli expressing the two dsRNAs targeting female development and male fertility were mixed with untreated mosquitoes in small population cages holding 50 untreated females, and varying proportions of dsRNA fed males and untreated males The mosquitoes collected from the dsRNA-fed cultures were not sex-sorted, which meant that a very small percentage of females were included in with the dsRNA-fed males. The impact on the size of the next generation was significant with even a seeding of the population of 25% dsRNA-fed insects, and the population was very strongly reduced when the proportion of sterile males exceeded 50%. (Table 13). This demonstrates that even without complete elimination of females from the dsRNA-fed insects, the sterile males are effective at competing with fertile males and reducing the mosquito population. The few non-sterile males, which have low fecundity, did not hinder the ability of the other males to reduce the population.

Mosquito larvae were also soaked in equimolar concentrations of the two dsRNAs (0.2 mg/ml), and the percent reduction on the population was equally if not slightly more effective than the bacterial feeding method (Table 14).

TABLE 13

Mixing dsRNA-fed (by *E. coli* feeding) mosquitoes into populations of mosquitoes reduces the effective size of the next generation. The values represent the means and standard errors for three replicate experiments.

| % dsRNA-fed mosquitoes[1] | Viable progeny of next generation[2] | % reduction from controls (no sterile males) |
|---|---|---|
| 0 | 952 ± 38 | 0 |
| 25 | 849 ± 36 | 11 |
| 50 | 590 ± 41 | 38 |
| 75 | 371 ± 32 | 61 |
| 100 | 67 ± 8 | 93 |

[1] The dsRNA-treated mosquitoes typically consisted of 96% males, 4% females.
[2] The number of live larvae after 12 days post-mixing of the sterilized insects with the untreated insects.

TABLE 14

Male mosquito sterilization frequencies following treatment with one dsRNA (0.02 mg/ml) or simultaneously with two different dsRNAs, each at 0.01 mg/ml. The values in the table indicate the percentages of males sterilized with just the single dsRNA (along the diagonal) or with two different dsRNAs (values above the diagonal). Not all pairwise combinations have been tested, but it is evident that some most combinations provide higher sterility than single dsRNAs. Many pairwise combinations of dsRNAs appear synergistic (marked with an asterisk *), as they show greater than a 5% increase over a simple additive effect. Some of the dsRNAs used are those identified herein, including Table 2 (e.g., dsRNA 1684 below corresponds to dsRNA AAEL001684 in Table 2).

dsRNA targets

| dsRNA | 1156 | 1684 | 2084 | 2275 | 4231 | 4471 | 4939 | 5010 | 5975 | 6726 | 6841 | 6975 | 7544 | 10639 | 11098 | 11310 | 12096 | 14408 |
|---|---|---|---|---|---|---|---|---|---|---|---|---|---|---|---|---|---|---|
| 1156 | 22 | 57* | | 65* | 67 | 53 | 40 | | 55 | 42 | | | | | | | | |
| 1684 | | 24 | 40 | 46 | 94* | 85* | 56* | | 63* | 50* | | | 90* | | | | | 74* |
| 2084 | | | 19 | 58* | | | | | | | | | | | | | | |
| 2275 | | | | 30 | 76* | 63 | 50 | | 56 | 45 | | 62* | | | | | | |
| 4231 | | | | | 34 | | | 80* | 88* | 89* | | | 96* | | 68* | 74* | 82* | |
| 4471 | | | | | | 27 | | | 78* | | 72* | | | | | | | |
| 4939 | | | | | | | 19 | | 48 | 42 | | | | 72* | | | | |
| 5010 | | | | | | | | 24 | | | | | | | | | | |
| 5975 | | | | | | | | | 29 | 80* | | | | | | | | |
| 6726 | | | | | | | | | | 18 | | 44* | 64* | 56* | | | | |
| 6841 | | | | | | | | | | | 25 | | | | | | | |
| 6975 | | | | | | | | | | | | 15 | | | | | | |
| 7544 | | | | | | | | | | | | | 28 | | | | | |
| 10639 | | | | | | | | | | | | | | 26 | | | | |
| 11098 | | | | | | | | | | | | | | | 22 | | | |
| 11310 | | | | | | | | | | | | | | | | 27 | 60* | |
| 12096 | | | | | | | | | | | | | | | | | 18 | |
| 14408 | | | | | | | | | | | | | | | | | | 22 |

Methods:

RNA isolation: Testes and male accessory glands (MAGs) were dissected from 2-day old male *Aedes aegypti* mosquitoes and were stored in RNAlater (Ambion). Tissues stored in RNAlater were centrifuged at 14,000 g for 5 min at 4° C., the supernatant was removed, and tissues were washed with 0.5 ml of DEPC-treated water and pelleted once again to remove the liquid supernatant. Total RNA extraction was performed using an RNeasy Mini Kit (Qiagen) and mRNA was isolated using an Oligotex mRNA Mini Kit (Qiagen) according to manufacturer's specifications. The poly-A RNA (1 µg) was used in the construction of each subtracted library.

Subtractive library construction: Suppression subtractive hybridization (SSH; Diatchenko et al. 1996) was used to identify genes that were preferentially expressed in *A. aegypti* testes relative to other tissues within the male mosquito's body. The testis-specific subtracted library was built using a PCR-Select cDNA Subtraction kit (Clontech) according to manufacturer's recommendations, using testis cDNA as the TESTER source of cDNA, and cDNA derived from the rest of the body, minus the MAGs, serving as the DRIVER cDNA. The SSH-specific adapters were ligated to the TESTER cDNAs and the two pools of cDNA were hybridized for the forward subtracted library. Reverse subtracted libraries were built for subsequent differential screening, where the TESTER and DRIVER designations were inversed. Amplification of hybrids corresponding to common sequences was suppressed, yielding a library enriched for differentially expressed sequences within the testes. The forward-subtracted library was ligated into the pDrive plasmid vector (Qiagen), which was used to transform DH5α *E. coli* cells (Invitrogen). The resulting cDNA library was plated on LB agar supplemented with 100 µg/ml ampicillin, 80 µg/ml Xgal, 0.5 mM IPTG and incubated overnight at 37° C.

Differential screening: The efficiency of the subtraction of the testes library was estimated using qRT-PCR by comparing the abundance of a predicted non-differentially expressed gene, β-tubulin, using the primers tubF (5' CGTCGTAGAACCGTACAAC, SEQ ID NO: 38) and tubR (5' CAGGCAGGTGGTAATCC, SEQ ID NO: 39). The testis subtracted library was screened for differentially expressed ESTs following the manufacturer's instructions using the PCR-select cDNA subtraction screening kit (Clontech). Briefly, 120 *E. coli* clones were selected randomly and grown in 50 µl of LB-ampicilin (100 µg/ml) for 6 h at 37° C. with moderate shaking in 96-well plates. Two microliters of each bacterial culture were then spotted in duplicate on LB agar plates, and allowed to grow for 4 h at 37C, followed by bacterial colony lifts onto Hybond+ membranes (Amersham Biosciences) using standard techniques. Probes for the forward and reverse subtracted libraries were prepared by labeling 100 ng total cDNA from each library with $^{32}$P-ATP by random priming, using the PCR-Select differential screening kit (Clontech) following manufacturer's instructions. Forward and reverse subtracted probes were hybridized to the DNA membrane at 65° C. for 2.5 h in a rotatory oven using Rapid-Hyb buffer (Amersham Biosciences). The membranes were washed with low stringency (2×SSC, 0.5% SDS; 3×, 20 min each) and high stringency (0.2×SSC, 0.5%

SDS; 3×, 20 min each) buffers at 65° C. The radiolabelled DNA was detected using a PharosFX Molecular Imaging System (Bio-Rad).

Identification of testis genes: Selected colonies (strong signal with the forward and low signal with the reverse subtracted probe) were grown overnight in 2 ml of LB-ampicillin (100 μg/μl) and purified using the Qiagen Mini-prep kit. Sequencing reactions were performed using Big Dye v3.1 chemistry. DNA sequences were compared to the *A. aegypti* genome within the VectorBase database and predicted *Drosophila melanogaster* homologues were identified using BLAST-X against the non-redundant database at NCBI with default parameters.

RT-PCR confirmation of testis expression: Tissue and sex-specific expression of the identified genes was confirmed and quantified using qRT-PCR, comparing expression of the genes' expression levels within testis, ovaries, and male bodies minus testis and MAGs. Reactions were performed in triplicate on a BioRad iQ5 Real-Time PCR Detection System using the primers listed in Table 15. S7 ribosomal protein (S7rp) gene expression was used as an internal reference to compare levels of RNAi. A single reference gene was deemed sufficient as the PCR efficiencies of the primer sets were calculated using the method of Pfaffl (2001), and were found to be essentially equivalent for all genes targeted by RNAi (β-tub, AeCS1, AeCS2, and hsp83) and for the S7rp reference gene, with values ranging between 95.2 and 98.1%. Melt curve analyses were also performed and confirmed that only a single product was amplified with each primer pair in every sample. Analysis of gene expression was performed using the $2^{-\Delta\Delta C_T}$ method (Livak and Schmittgen 2001), comparing expression in specific dsRNA treated samples to gus-dsRNA treated samples.

TABLE 15

Primers used to amplify gene fragments for dsRNA synthesis or for qRT-PCR analysis. SEQ ID NOs: are shown in parentheses.

| Gene | dsRNA primers | qRT-PCR primers |
|---|---|---|
| AAEL001033 | F TTTCAAGCAACCGGTGACAG (48)<br>R TTGAGGGACGTTTTGGAAGC (49) | ACACTTCGCTCATTCCAC (120)<br>ACCTTGCTGTCTCCATCC (121) |
| AAEL001156 | F GCAAAACTGACCATCCTGCA (50)<br>R CCGTTCTTGCAGTTTCAGCT (51) | CGATGTGGACTATACGGAAAC (122)<br>GGATTACTTGACGGTGCTTC (123) |
| AAEL001684 | F CTGTGCCGGTTATTCAGCTC (52)<br>R GGGATGTTGTTGATCGTCGG (53) | GGTATTCGTCGGTGGTATCAG (124)<br>GCCTCGTGTTCGGTTTCG (125) |
| AAEL002084 | F TTGCTGGACGAGAAGGAAGT (54)<br>R ACTGAGCTGGTTGGTGAAGA (55) | AAGGAGTACGAAGAGAAGAAG (126)<br>CGGAAGCGGTTCATTAGG (127) |
| AAEL002275 | F AGATCGAGCACTGTTTCCGA (56)<br>R CGTATACATGGGCCCGATCT (57) | GTCGTTTGGTGCGGCGTTTG (128)<br>CCTTGTTGTCCTCCTCATCCTTGG (129) |
| AAEL003501 | F CGCAAGGATCGGAAACCAAT (58)<br>R CATGCTGTAGATCGGGTTGC (59) | CAGCAGGATACGGTCTTC (130)<br>GAATAGGTCGGATTGTTGG (131) |
| AAEL003757 | F AAAGGAGCGAAGGAGACCAA (60)<br>R AGGTAGTGTTTCAGGGCCTC (61) | GCGGCGGATGCGATTCTC (132)<br>GACTCTTGGCGGAACGATAGC (133) |
| AAEL004231 | F AGCCAAAGGAAGTACGGTCA (62)<br>R CTTTCAGCTCTCCGATGTGCV | GAGCATCAGTCGCACATC (134)<br>TCCTTCTCTCGCAGTAACC (135) |
| AAEL004471 | F CGCGCCAAGAAGAAGATCAA (63)<br>R ATTTTGTCCCGCAGCATAGC (64) | AAGCACAACACCAGGAAC (136)<br>GAAACCATCAGCCAAAGC (137) |
| AAEL004696 | F GATACCGAAATGTGCACGCT (65)<br>R CCGGTTCTTTGTCACTGCAA (66) | CCGTGCTTGAGTTGATAC (138)<br>ATTGGAATCTGATGGTGAG (139) |
| AAEL004939 | F TATCCTGGGCAGCTGAACTCV<br>R CAATGCGAGAAGGTACCGTG (67) | GAACACCACCGCCATCAC (140)<br>CCTGCTTCTTCTTGACTTTCG (141) |
| AAEL005010 | F GTTTTCGTCGGTCCGGTTAG (68)<br>R TrGGCTTGGGTCTCCTTGAT (69) | CGGTGGAAGTGGATTGTC (142)<br>CGTTCTGATTCTTGCTGATG (143) |
| AAEL005975 | F TGGACAAGGCGGAACAAAAG (70)<br>R CTTGATTCGAGGCCTCAACG (71) | GAGCAGAGATGGAGGAAC (144)<br>CAGGCGTAACAGTCGTAG (145) |
| AAEL006726 | F GCATTCCTGTTCTCGTTCCC (72)<br>R TGAAGTCACATTTGGCCAGC (73) | TGGCTTTGGTTCATTErG (146)<br>TATCCGATGTTGGCTTCC (147) |
| AAEL006841 | F CATCGGGTGTTGCTTCTACG (74)<br>R TCAAAGTACACGTGCTGCAG (75) | ACGGTGCCTATCTGAGAAG (148)<br>GGATGCTGATGAACGCTAC (149) |
| AAEL006975 | F GCCATTTCGATGCCAAAACG (76)<br>R TCGACTGAAATCCGGGAACA (77) | CGTCTGGTGTAGGTGCTAAGTG (150)<br>TGCTTGTTCTGCCGCTTGC (151) |
| AAEL007144 | F AACACTTCAACACGTGTCGG (78)<br>R TCGTACACTTCAGCGGAGTT (79) | TTCGCATACGGAGTGTTAC (152)<br>CCTTGTGGATGTAGTCTCG (153) |
| AAEL007188 | F GCAGCGCCAATATCTGAACA (80)<br>R TTCCCGCTTCTTCAGGTGAT (81) | TTCGCAGTCGGATTACTTCTTC (154)<br>TGGTTCTTGGTGATATTCGTAGC (155) |

TABLE 15-continued

Primers used to amplify gene fragments for dsRNA synthesis or for qRT-PCR analysis. SEQ ID NOs: are shown in parentheses.

| Gene | dsRNA primers | qRT-PCR primers |
|---|---|---|
| AAEL007434 | F CTGTCCTCGCCCAATGAATG (82)<br>R CTGCAGTAAATCTCCGCACC (83) | TGCGTTCTGTTCATAATGGTTAC (156)<br>GTCGGGTTTGGTTTCACTCC (157) |
| AAEL007544 | F ATCGTCTATGGCCGGCTTTA (84)<br>R TAGCGCTATGATGTCGTCGT (85) | AGTTCTCCTTCCGACATC (158)<br>GTAAGCCGCACATTCATC (159) |
| AAEL007684 | F AGCGATGCAGGACGAGATTA (86)<br>R CGTGGGCCAGTTTCTTATCG (87) | CGCCACCAGATGTCCTAATG (160)<br>CAGTTGTTCCGATTGCTTCC (161) |
| AAEL008428 | F TTGGGCATGCTTCACTGATG (88)<br>R ATCGTCGGAGTATCGCTGTT (89) | TGTTGGATGATGTTGTGAGATGTG (162)<br>ATCGTCGGAGTATCGCTGTTC (163) |
| AAEL008678 | F GCCGTTTCCAGGACAACTTT (90)<br>R GTAGTAATCCCGCTCTGCCT (91) | CCAGTCAGAGGGCGAATG (164)<br>CTTCTCCGTCAGGTCATCC (165) |
| AAEL009047 | F GGAACGGTGAAATCGATGGG (92)<br>R TTCACTGCTGTCETTGTGTG (93) | CACAGAGGAGGAAGTAATTG (166)<br>CACTATTGGACTGCTAACG (167) |
| AAEL009321 | F CAGCGACGAACCACAATGTA (94)<br>R GCTTATCGCCGATGGTTACC (95) | GTATATGTCGCCTCGGTTC (168)<br>GGGTTGTATCGGTGTTCC (169) |
| AAEL009357 | F TCAAGCAAGTGCTGGACAAC (96)<br>R TGCCTTCAGGTCGTTCTCTT (97) | |
| AAEL009553 | F CAGTAGCTTTCCGTCCATGC (98)<br>R GACCAGCGGATAAATCGCAG (99) | GTTGCTCTTCGTCATTATTCC (170)<br>AAATCCATTGCCATCTTTGC (171) |
| AAEL010639 | F GCGCACGTTATGATGGGAAT (100)<br>R TTCCCTTGCATCACATCCCT (101) | GCGGAGATGTTACCTTGAAG (172)<br>GAAACTACCTGGACCTCTGG (173) |
| AAEL011098 | F TTGGCGAAATTCTGCAAGCT (102)<br>R AGCCGAAACGTTTGCTTCAT (103) | ACTCATACACTCGTTTCAAG (174)<br>TCCATATCCGAAGCACTC (175) |
| AAEL011310 | F GGATATGAGACCCGAACCGT (104)<br>R GTTTTTCTTCGGTGCCTTCGT (105) | GAAGATGCCGAGCGAGAG (176)<br>GACCGACCTGGATGGATTC (177) |
| AAEL012096 | F AATACCAGCACGCTCTCTCA (106)<br>R ATTGCATCGGTGGCAAGTTT (107) | |
| AAEL012446 | F GCTACTTGGATTTGGGCGAC (108)<br>R ATCGCTTCGGACAGGATGAT (109) | CGGAGCCAAGGAGGTCATC (178)<br>ACAGCAGCAGAAGCAGAGG (179) |
| AAEL013621 | F TTTGAACCCGGAAAAGGCAG (110)<br>R TTCGACGAAATCCTCCCACA (111) | CCAGAGCAACCGAGAGTATG (180)<br>CGACGAAATCCTCCCACAG (181) |
| AAEL013723 | F GATGAAACTGCCGCCACTAG (112)<br>R TTGCCGAACCGTTGGAAAAT (113) | TTAAGATTGTCACCTTCACC (182)<br>CGTTGTAGATGTTCTGTCC (183) |
| AAEL013737 | F AAGACTTGGGAAGAGGACGG (114)<br>R TTCTCTAGCAGCTGGATCCG (115) | TGTAGTTCGGTATCGTTCGG (184)<br>TCGGCATTCCTTCGTTCG (185) |
| AAEL014067 | F TTGCTCATACGCTCCATTGC (116)<br>R TTGCTCCTGAACGGTGAGAT (117) | ACAACAGAGCCTAAGACTATC (186)<br>CGACAATCATATTCTCACAGC (187) |
| AAEL014408 | F GACCGATCCTGCAAAAGTCC (118)<br>R TTTGCTCCTGGGTGTAGAGG (119) | TGGACGATAATGCTCAAC (188)<br>GAGGCGAATGGAGTTATG (189) |

Isolation of the dsxF gene fragment in *A. aegypti:* The two primers pairs, dsxf1-for (GGTCAAGCCGTGGTCAAT-GAAT; SEQ ID NO:40) and dsxf1-rev (CAACATTCTC-CGCGCACAGG; SEQ ID NO:41) and dsxf2-for (GCAAATGCTGTTTAACGATAATAG; SEQ ID NO:42) and dsxf2-rev (CGGAGCCGTTTGGCAACGG; SEQ ID NO:43) were used to amplify portions of the two female-specific exons of the dsxF transcript (Genbank accession numbers: DQ440532 and DQ440533). These two PCR products were subsequently used as templates to prepare dsR-NAs by in vitro transcription, and were used in equimolar concentrations for dsRNA soaking or were cloned into pL4440 plasmids, to be used to transform *E. coli,* for bacterial feeding, as described below.

Injecting dsRNA into mosquito pupae: Total RNA was extracted from late pupae and early adult male *A. aegypti,* using QIAshredders (Qiagen) to homogenize tissues and an RNeasy RNA extraction kit (Qiagen). RNA was treated with amplification grade DNase I (Invitrogen) and 1 µg was used to synthesize cDNA using a First Strand cDNA Synthesis kit (Invitrogen). The cDNA served as template DNA for PCR amplification of gene fragments ranging in size from 260 to 380 bp in length, using the primers listed in Table 15. The gene fragments were subcloned into the cloning vector pDrive (Qiagen), and later excised from pDrive using either ApaI and PstI or MluI and NotI restriction enzymes, then ligated into a similarly-digested plasmid pL4440, a vector possessing convergent T7 promoters (kindly provided by Andrew Fire, Stanford University). A 401 bp fragment of the β-glucuronidase (gus) gene, a bacterial gene specific to Escherichia coli, was amplified by PCR from the pBac-PAK8-GUS plasmid (Clontech) using the following primers: GusF 5' CCCTTACGCTGAAGAGATGC (SEQ ID NO:44) and GusR 5' GGCACAGCACATCAAAGAGA (SEQ ID NO:45)). The 401 bp PCR product was cloned into the dsRNA transcription plasmid pL4440, as described above, to be used as a negative control. DNA templates for in vitro transcription of each of the gene fragments in pL4440 were PCR-amplified using the following pL4440-specific primers: pL4440F 5' ACCTGGCTTATCGAA (SEQ ID NO:46) and pL4440R 5' TAAAACGACGGCCAGT(SEQ ID NO:47). PCR products were then purified using a QIAquick PCR purification kit (Qiagen). The MEGAscript RNAi kit (Ambion) was then used for in vitro transcription and purification of dsRNAs. DsRNAs were diluted to 0.1 mg/ml in 20 mM phosphate, pH 7, and each pupae was injected with 50 nl. To assess for RNAi, insects were allowed to develop until 3-days post-eclosion and RNA was extracted as described above.

Feeding dsRNA to mosquito larvae: Mosquito larvae were soaked in two concentrations of in vitro-transcribed dsRNA (0.02 and 0.2 mg/ml dsRNA) in dechlorinated tap water for 1 h each day, and then returned to their feeding trays. To feed larvae bacteria, the pL4440 plasmids containing the mosquito genes were used to transform HT115(DE3) E. coli cells and dsRNA production was induced by growing the liquid cultures of Luria Broth supplemented with 50 µl/ml ampicillin and 0.4 mM IPTG. Once the cultures had reached an OD of 0.7-0.8, the cells were pelleted by centrifugation and mixed with 1% LB-agar containing ampicillin and IPTG and 1 g of finely ground Purina Rabbit Chow, cooled to 42° C. to ensure the bacteria were not heat killed. The agar bacteria mixture was plated to a thickness of 5 mm, cooled, and then cubed into 5 mm cubes, to be fed to mosquito larvae. To feed heat-killed bacteria in the same mixture, following pelleting, the bacteria were exposed to 70° C. for 1 h, and then mixed with the agar-rabbit chow mixture and plated and cubed. Agar cubes were stored at 4° C. until needed. Mosquito larvae were raised in densities of 0.5 larva/ml water (groups of 10 larvae in 20 ml) and provided single cubes of bacteria-containing agar on a daily basis. As pupae developed, they were transferred to individual vials to await eclosion and sex-sorting.

Mosquito fertility assays: Individual 3-day old dsRNA-treated mosquitoes were provided virgin mates in 25 ml plastic vials for 2 days. Mosquitoes were provided 10% sucrose ad libitum, and to assess fertility and fecundity, females were provided blood meals (derived from rats) 2 days post-mating, and eggs were collected on moistened paper towels placed within the vials for a week to 10 days post-blood meal. Eggs were incubated at 25° C. for 4 days, and then immersed in water to assess hatch rates and calculate fecundity. If no eggs were produced, or all eggs failed to hatch, the dsRNA-treated insect was considered sterile. For small population mating competitions involving only 20 mosquitoes, 500 ml glass jars with screen-covered lids were used, while mating competitions using 100 mosquitoes were conducted in larger (45×45×45 cm) screened cages.

RNAi in Drosophila: Fragments of D. melanogaster genes were PCR-amplified using the primers listed in Table 16. DsRNAs were prepared as described above, and were injected (20 µl of 0.1 mg/ml) into wandering phase late instar larvae. Two days after adult eclosion, insects were collected and RNA was extracted to assess the extent of RNAi.

To test for impacts of the dsRNA on fertility, dsRNA-treated males were mated to two virgin females, and the number of progeny produced was compared to gus-dsRNA-treated males. A male's fertility/fecundity was considered to be reduced if there were more than 30% fewer progeny than the controls (Chi square, P<0.05). The dsRNA-treated males' ability to compete with fertile males for mates was assessed by mixing five dsRNA-treated males were mixed with five untreated males and 5 females. A reduction in the production of viable adult progeny of greater than 30% was considered significant, relative to control mating with 10 fertile males (ANOVA, P<0.05).

TABLE 16

Primers used to amplify gene fragments from D. melanogaster and primers used for qRT-PCR analysis of RNAi. SEQ ID NOs: are shown in parentheses.

| Gene (Aedes accession no. and FlyBase accession no.) | dsRNA primers | qRT-PCR primers |
|---|---|---|
| AAEL001684 CG4727 (bol) | F GCGGATGGTGAATGCGTGGT (190) R TGGGGATTGTGGATGCGACTG (191) | TACGGCACACTAATACCCAATC (208) TGCTCTTTACCGTGCCATAG (209) |
| AAEL002275 CG3565 | F CTGGAGAATGCCCGCTTCAACTAC (192) R GGTGAAAAGCCGCACAAAGGAC (193) | CGCATTCTCGGTCTACGATAAA (210) CTTCATCCTCGCTCTCAAAGAA (211) |
| AAEL004231 CG14271 (Gas8) | F GCCTCAAGACGCGCAACACT (194) R GTTGCCCACCCGTTCATCCA (195) | GAGGCGATGACCCAACTAAA (212) TCTCGCTCATCTCCATTCTTTC (213) |
| AAEL004471 CG4568 (fzo) | F CGCGGTGTCAGCGTTAAAAA (196) R CTGGCCTATTTGTGCTGGGA (197) | GTCCTTCAATGTCTCTCCATACC (214) CAATCCAGGCCGTAGATTAGTT (215) |
| AAEL004939 CG32396 (β-tub) | F GCTTGACCTCTCTAATAATGG (198) R GAAAATTCCAGCAGCGGTC (199) | TCCGGCTTGACCTCTCTAATA (216) CGACGGAATGGTCACATAGTr (217) |
| AAEL005975 CG15259 (nht) | F TGCGAGCATCGAACAAGCTA (200) R ATCGGAGCACCGGTCAATTT (201) | CAAGAATGGCTCCTGGATTCT (218) TCGTCGTTGTGCAGATGATAG (219) |
| AAEL006975 | F GCAACAAGCGCAAGCAGGAT (202) | CCTGACTGGAGATCGTTTATGG (220) |

TABLE 16-continued

Primers used to amplify gene fragments from D. melanogaster and primers used for qRT-PCR analysis of RNAi. SEQ ID NOs: are shown in parentheses.

| Gene (Aedes accession no. and FlyBase accession no.) | dsRNA primers | qRT-PCR primers |
|---|---|---|
| CG18369 (S-Lap5) | R CAGAGCGGCAGTACGGCCGT (203) | GCTGATGTCGAAGGTGAGATT (221) |
| AAEL007188 CG17083 | F TCGGTGAATCGCCTGTTTGA (204) R AAACACTAGCCGTCAGCTCC (205) | AAGTTTCAGCAGCAGGAGAG (222) ACAGGCGATTCACCGAATTAT (223) |
| CG9313 | F GCCCACAACATGTCCGTCTA (206) R AAGGCGAGCTTCTCGTTGAA (207) | ATATGCGTCCAGATCCGCTG (224) GTCGAAAACGTGGACCTTGC (225) |

REFEFENCES

Alphey et al., (2010) Sterile-Insect Methods for Control of Mosquito-Borne Diseases: An Analysis. Vector Borne Zoonotic Dis. 10: 295-311.

Baum J. A., Bogaert, T., Clinton, W., Heck, G. R., Feldmann, P., Ilagan, O., Johnson, S., Plaetinck, G., Munyikawa, T., Pleau, M., Vaughn, T., Roberts, J., 2007. Control of coleopteran insects through RNA interference. Nat. Biotechnol. 25, 1322-1326.

Bloem, K. A., Bloem, S., 1999. SIT for codling moth eradication in British Columbia, Canada. In Area-Wide Control of Insect Pests: Integrating the Sterile Insect and Related Nuclear and Other Techniques. Proceedings, FAO/IAEA Symposium, Penang, Malaysia Universiti Sains Malaysia, Penang, Malaysia.

Diatchenko L., Lau Y. F., Campbell A. P., Chenchik A., Moqadam F., Huang B. et al, (1996) Suppression subtractive hybridization: a method for generating differentially regulated or tissue-specific cDNA probes and libraries. Proc Natl Acad Sci USA, 93: 6025-6030.

Franz, G., Gencheva, E., Kerremans, P., 1994. Improved stability of genetic sex-separation strains for the Mediterranean fruit fly, Ceratitis capitata. Genome 37, 72-82.

Gempe and Beye, 2010, Bioessays, 33:52-60.

Helsinki, M. E. H., and Knols, B. G. J., 2008. Mating competitiveness of male Anopheles arabiensis mosquitoes irradiated with a partially or full sterilizing dose in small and large laboratory cages. J. Med. Entomol. 45, 698-705.

Hendrichs, J., Franz, G., Rendon P., 1995. Increased effectiveness and applicability of the sterile insect technique through male-only release for control of Mediterranean fruit-flies during fruiting seasons. J. Appl. Entomol. 119, 371-377.

Holbrook, F. R., Fujimoto, M. S., 1970. Mating competitiveness of unirradiated and irradiated Mediterranean fruit flies. J. Econ. Entomol. 63, 1175-1176.

Jacque et al., 2002, Nature, 418:435-438.

Klassen, W., Lindquist, D. A., and Buyckx, E. J., 1994. Overview of the Joint FAO/IAEA Division's involvement in fruit fly sterile insect technique programs. In: Fruit Flies and the Sterile Insect Technique (eds. Calkins, C. O., Klassen, W. & Liedo, P.) 3-26 (CRC Press, Boca Raton, Fla., 1994).

Knipling, E. F., 1959. Sterile-male method of population control. Science. 130, 902-904.

Knipling, E. F., 1960. The eradication of the screwworm fly. Sci. Am. 203, 4-48.

Lofgren C. S., Dame D. A., Breeland S. G., Weidhaas D. E., et al. (1974) Release of chemo sterilized males for the control of Anopheles albimanus in El Salvador. Ill. Field methods and population control. Am J Trop Med Hyg. 23: 288-297.

Mayer, D. G., Atzeni, M. G., Stuart, M. A., Anaman, K. A., Butler, D. G., 1998. Mating competitiveness of irradiated flies for screwworm fly eradication campaigns. Prey. Vet. Med. 36: 1-9.

Robinson, A. S., 2002. Genetic sexing strains in medfly, Ceratitis capitata, sterile insect technique programmes. Genetica. 116, 5-13.

Salvemini et al, 2011, BMC Evolutionary Biol., 11:41

Sambrook et al, *Molecular Cloning: A Laboratory Manual.*, Cold Spring Harbor Laboratory Press (1989).

Sui et al., 2002, Proc. Nat'l. Acad. Sci. USA, 99:5515-5520

Vreysen, M. J. B., Saleh, K. M., Ali, M. Y., Abdulla, A. M., Zhu, Z. R., Juma, K. G., Dyck, V. A., Msangi, A. R., Mkonyi, P. A., Feldmann, H. U., 2000. *Glossina austeni* (Diptera: Glossinidae) eradicated on the island of Unguja, Zanzibar, using the sterile insect technique. J. Econ. Entomol. 93, 123-135.

Whyard, S., Singh, A., Wong, S., 2009. Ingested double-stranded RNAs can act as species-limited insecticides. Insect Biochem. Mol. Biol. 39, 824-832.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A modified insect comprising decreased expression of a testis-specific coding region compared to a control insect,
    wherein the modified insect is a member of the family Culicidae or the family Tephritidae,
    wherein the testis-specific coding region is selected from SEQ ID NO: 1-7 or 9-13, or a homologue thereof,
    wherein the modified insect is male, and
    wherein the modified insect comprises, when compared to the control insect, reduced fertility, reduced fecundity, or a combination thereof.

2. The modified insect of claim 1 wherein the insect is a mosquito.

3. The modified insect of claim 2 wherein the mosquito is *Aedes aegypti*.

4. The modified insect of claim 1 wherein the expression of more than one testis-specific coding region is decreased.

5. The modified insect of claim 1 wherein the modified insect further comprises decreased expression of a coding region encoding a sex differentiation polypeptide compared to a control insect.

6. The modified insect of claim 5 wherein the sex differentiation polypeptide is a doublesex female splice variant.

7. A method for producing an insect comprising:
    administering to a juvenile insect a composition comprising a double stranded RNA (dsRNA) that inhibits expression of a testis-specific coding region, wherein the testis-specific coding region is selected from SEQ ID NO: 1-7 or 9-13, or a homologue thereof, wherein the juvenile insect is a member of the family Culicidae or the family Tephritidae; and
    allowing the juvenile insect to mature into an adult, wherein the adult insect has reduced fertility, reduced fecundity, or a combination thereof, compared to a control insect.

8. The method of claim 7 wherein the administering comprises feeding the composition to the juvenile insect.

9. The method of claim 8 wherein the dsRNA is present in bacteria that are fed to the juvenile insect.

10. The method of claim 9 wherein the bacteria are inactivated.

11. The method of claim 7 wherein the juvenile insect is a larva or a pupa.

12. method of claim 7 wherein the dsRNA is a first dsRNA, further comprising administering to the juvenile insect a second dsRNA that inhibits expression of a coding region encoding a doublesex female splice variant.

13. An insect produced by the method of claim 7.

14. A population of an insect produced by the method of claim 7.

* * * * *

SEQUENCE LISTING

```
<160> NUMBER OF SEQ ID NOS: 250

<210> SEQ ID NO 1
<211> LENGTH: 546
<212> TYPE: DNA
<213> ORGANISM: Aedes aegypti

<400> SEQUENCE: 1
atgtcgatac cgaaccctgc gggacagata gacggcgcac tggctgcgcc caagtacggt      60
acgctcattc cgaaccgggt attcgtcggt ggtatcagtg cgacacgac  ggaagcggaa     120 ctgtgccggt tattcagctc gtacggcaac gtcaagtcaa cgaaaatcat cgtagatcgg    180
gcgggcgtca gcaaaggcta cggattcgta acgttcgaaa ccgaacacga ggcacaaaga    240
ctgcagagcg atggagactg tatcgtgctg agggaccgta agctaaacat agcaccagcg    300
attaagaagc aagtaagttg gcaccataca atctgcgcga cgaacggtgc cgtgtactac    360
gcagccacac ccccgacgcc gacgatcaac aacatcccca tcgagcagtt tgcgacggca    420
gtctatccgc ccggtgtgcc aacaatctat cctccgacga tgacgcccta ccagccgttc    480
taccagtact acagcgtgcc aatgaatgta ccgacaattt ggcctcagaa ctatcaaggt    540
atgtaa                                                               546

<210> SEQ ID NO 2
<211> LENGTH: 654
<212> TYPE: DNA
<213> ORGANISM: Aedes aegypti

<400> SEQUENCE: 2
atgtctttgg atttgaccct ggacgcgggc gaggagatgc gtttcctgaa caaagttagt     60
cgtttggtgc ggcgtttgga aagaaaacc  catttcacgc accgggagtt ggaggtttgt   120
ctgttgatct actacaaact gaccaaggat gaggaggaca caaggggca  tgtttcccgg   180 catcagttgg acgtcctgtt tgatagcgtt ttcgggatat ctgatagcga aactgttgga    240
aggatttgta cggcgctgga caaaagtgtc acgaccttta tgagtatgga atcgtgggtc    300
aaaatgttgt cgttgttctt gaaaggaaca ttcgacgaga agatcgagca ctgtttccga    360
gcttatgata tcggcggaga agagttactt cggagagaac acatgatgat attgttgcgg    420
agttgtttca tcaagcacca agaagaggaa gtcgaagaat cggttaagga catggtcgaa    480
attcttatcc gtcgaatgga cgttgatcga gatggagcca tttccttgga tgacttccga    540
caatccgttc acaagtcacc agaacttcta gagtgcttcg gccaggcact tccagatcgg    600
gcccatgtat acgctttctc taaaaccttc ctcgaccagt cggctgagtt ctaa           654

<210> SEQ ID NO 3
<211> LENGTH: 1464
<212> TYPE: DNA
<213> ORGANISM: Aedes aegypti
```

<400> SEQUENCE: 3

```
atgcaacatt tctatttcaa ggcactctgt atgggtccca aaaaagccaa aggaagtacg      60
gtcatcgatg gggtggacac atccagtatg tcccgcgaac agctagaaca gtttgcgctc     120
cggcttcgca acgagatgga acgggaacgc gaggagcgaa acttcttcca gctggagcgg     180
gacaaactgc gcacgttctg ggaaatcacg cgcaaacagc tcgaggaagc gaaagccgtg     240
atacgcaaca agaacgtgac gtagaggtt gcccaagaac ttgccgacca ggacacgaaa      300
aatgtgatgc aggagatgaa gcatctgcag tacgagcatc agtcgcacat cggagagctg     360
aaagcggaaa tgatgacaca gctgaagatg gctcaggaag atcactcgct acaggaacga     420
gaacttctca cgacaaacg tgacctgcga cggttactgc gagagaagga ggaaaactct      480
gaactagaag tacagcagct taaactaaag cacagcgaac tgctgagcca gaacgcgga      540
aagtttaaag aggaaattga cgcaatgacc aaattgtttg aacagcgcct acagagctat     600
aaagaagaag ctgaagtgcg ccacgaaatg gaattgtcag aggtcgaaga acgaaagaac     660
ggccaaattt ccgaactgat ccaaaccaat gaaaacgcct acaaggaaat gaagggttac     720
tacaacgaca ttaccctgaa caacttggca ctcatcaaca gtatgaaaga acagatggaa     780
gagttgcgta ttcaatcaga caaggacctg aagaaccatt cggaagtgat ggcggagaac     840
agaagactcg ttgaaccgtt gaagcagtcc caatcagagt tggtcgagtt gcgcaaaaag     900
ttgcaatact acgatcgcga caaggctacg ctcaatcgag tgaaaactcg gctcgcttcg     960
acgcagaaac agctcagtag cttgaagctc gaatcggacg tcctgcagat gcgctgcgag    1020
aagctggtcg aagaacgcga tcagctgaag aatatgttcg agaagtctat actggagctg    1080
caacagaagt caggtttgaa aaattcctta ttggagcgaa aactagaata catcgagaag    1140
caaacggaac aacgggaagc catttaggg gaggtgctat cgcttgccgg aatcgaaccg     1200
cagtcgttga gtatccgaat tgaaaaactt ctggtgcaga aaaacgacaa atccaagac     1260
ctacgctacg aactggcccg cgttagcaaa atgtacgacg acttgctgtc gatgatggag    1320
gctaaattgg caaagtatgg cataactta aaggatctgg agctgagcag catgagattg     1380
gaaaagtgaa tttggcacaa gagaaaaact tccgacttta ataagttgt tgcacaggtt     1440
tgcaaataaa cttttggaca cagt                                            1464
```

<210> SEQ ID NO 4
<211> LENGTH: 3091
<212> TYPE: DNA
<213> ORGANISM: Aedes aegypti

<400> SEQUENCE: 4

```
atggccgcct atcttaaccg taccctgtcg atggtgacgg gctcgaatgg gtcggcctcg      60
acgggatacg acacggcggc actgatcgat gcgaacacat cgtcgccgcg gggtctgcac     120
acggccactg gtggcgggc tgccggccac aacgacgtct cgccgttgca gattttcgtc      180
cgcgccaaga agaagatcaa cgacatcttc ggcgagatcg aggactatgt ggtggagaca     240
accggattca tcgatgccct cccgacgatg gtggaaatcg tggacaaagc cgagtcggag     300
ctattccgga gctatgtgct gaaagtgtcc ggcatccggg aggtgctcgc ccgtgaccac     360
atgaaggtgg ccttctttgg gcgcacctcc aacgggaaaa gttcagtgat caacgctatg     420
ctgcgggaca aaatcctacc gagtggtatc ggccacacca cccattgctt ctgccaggtg     480
gagggcatcg atggcgacga ggcataccta gtcaaggaag ttgtgatga aagctgaat      540
gtaacgtcga ttaaacaact tgccaatgcg ctatgccagg ataaactctc ggaaagctca     600
```

```
ttgatcagga tattctggcc acgtaaacga tgtaacttgc taagggatga tgtagttttc    660
gttgattcgc ccggagtcga tgtgtcacct aatttgaacg attggataga caatttctgc    720
ttaaatgctg acgttttcgt gttggttctc aatgctgaat ccactatgac cttggcggaa    780
aaacacttct tccacgaagt ctcaacccgg ctttcgaaac cgaacatttt tgtgctgaac    840
aaccgttggg atgcatcggc ctcagagccg gagttccagg aatcggtcaa agcacaacac    900
caggaacgat gcgtcgattt cctcgtgaag gagttgaagg ttgcatccgg aaaggaggca    960
gaggaacgcg tcttcttcgt gtcagcgcgt gaaacactgc aggcccgatt gaaggaagcc   1020
gaaggtctgc cagcgattgc cggcgctttg gctgatggtt ccagaaccg gtactttgag    1080
ttccaggact tcgaacggaa gttcgaggaa tgcatctcga aaagtgcagt cagaaccaaa   1140
tttgaacaga cagctctcg cggcaagagc atctcaacgg agatgcgcat gatgctggac    1200
aacatcttcg accgggcgaa tgtcctgcgc aatcagaagc tggaacagaa gaagaaactg   1260
actgatcgga tcgcaaatac cgaaacacaa ctgatgcaag tgacacgaga gatgaaaatg   1320
aagatccaca acatggtcga ggaagtcgag caaaaagtgg ccaaggcact gaacgaggaa   1380
atttggcgac taaacgtgct ggtggatgag ttcaacctgc ctttccacac ggatccattg   1440
gttctgaacg tttacaaaaa agaaatcaac gcccacgtgg aaagtggcct tggttcgaat   1500
ctgagggcgc gacttagcac agcttttagcc atgaacgtcg aaacagcgca agggaaatg    1560
accgaccgca tgactgcgct gatcccgtcg gaaaagatca tcacccacac gcatcacgtc   1620
gttgcgcgga atcaaccgtt cgagatgctg tacacgctga actgtcaaaa cctatgttcc   1680
gatttccaag aggatctgaa tttccgcttc tcctggggaa tcactgcgtt catagcgagg   1740
tttaatggca aaatgcgagc gaacagcaag aaagcaattt cgcacaatag gcaaagtagc   1800
aatatgaatg tatcgcaagt aatgtctcct acttcaccga tgtgtcttat gccggataac   1860
gaactgatca cagaagagca gctgtcggtg atatcgaagg tggcgatagc ttcgatcgga   1920
tcccagggca ccctggggct tctggtggcc ggtgtgctcc tgaaaacaat tggctggcga   1980
gtgattgtgg gtgccggcat cctgtatggc agcgtgtatc tctacgagcg cctgtcctgg   2040
accaacgccg ccaaagagaa gaatttcaaa accagtatg tgcagcacgc cacacggaag    2100
ctgaagttga ttgtcgatct cacttcggcc aactgcagcc accaggtgca acaggagctg   2160
tccagcacct tcgcccgatt gtgtcgcgtt gtcgataccg ctaccacaga gatgaacact   2220
gaactgaagg acatcgaaac ctccctggcc gtgatcgagg ccaaccagaa gcaaatcaag   2280
gtgctcagca ataaggccaa cttcatccag cgcgagctgg aaatcttcga cagcaactat   2340
atcaaggaga actaagttga acccttctga agagggtagc aagagttaat gtttaatata   2400
ttgtattctc gccaggagac agcgtcactc aaaccggtat cgaaaccaaa caagtttgt    2460
agcttggatg gatgtgacag aaagtttagt tacatagaac ctacgttcct tgttcacact   2520
ttttacctga ttcgatactt tgcaaacatt gctatattta tattttaaa tgttatatgc    2580
tttagtttcc aattttgatt agttgctgtg caccaacata tttggttgga tagttatcgt   2640
cacctccaaa gcaagaatct acacaccaac cgaatatgta ctacaaagat tattgatgca   2700
agtgagtgaa acttacttag agaatacgct aatgaatccc taacaaaata tttcaatgta   2760
actgtgtata atatatccta agacttagta ctgtaggaga ggtcgttttc ttgtacaggt   2820
attaccgtac agactaaagg cagttagata tttctgttca acgatagatg agggctgttg   2880
taaaaataaa ttaaatctat cgaaaaagct aaaatcggaa actagaccaa gcgttgattg   2940
```

| cagaagctag accgcaaacc gttagataaa ttgggtatcc ctgttttgta ctgttgtacc | 3000 |
| acgttgactc aatccttgat ttacttcgat caaattgtac cgaaaattat aactgaaaaa | 3060 |
| ttgaaccctg aaataaagta tttccaactt c | 3091 |

<210> SEQ ID NO 5
<211> LENGTH: 1329
<212> TYPE: DNA
<213> ORGANISM: Aedes aegypti

<400> SEQUENCE: 5

| atgcgtgaaa tcgttactct tcatcttgga caatgtggca acaaaatcgc ccagacattc | 60 |
| tgggaaacta tctgcgagga gcactgccta acgagcgcg gccagtttat agggaaacac | 120 |
| tttctgccac ttcaacggat caacgtgtac tttgaggagg ctccctgctg caatttcgta | 180 |
| ccaagggcaa tctttgccga cctggaaccg ggtgcgatgg tcggtttgaa atgcagccgc | 240 |
| ttcgggcagc tcttttcccc ggaaagcatg gtcaacggga tgctcggagc tgggaataac | 300 |
| tgggctcgag gctaccacac ggaaggcgcc gaaatgttgg acaggatcat gaatgtggct | 360 |
| cggaaaatgg tggaaggttg tgattgtttc caggggttcc aaatggtaca ttcgattggc | 420 |
| ggcggaaccg gatccggatt gggaacgctg atgatgaga catgaaaga tgaatttcct | 480 |
| cggaagatac tcaacacttt cagtgtgatc ccgtccgaaa aggtttcgga ggtcgttgta | 540 |
| gaaccataca atgcagtttt cgctttaaac tccatgacgg attgcagtga tgaaacgttc | 600 |
| tgcctggata cgaagcccct gtacaacata aatatgacaa cgcttcgagt cgacaaaccc | 660 |
| accatagacg atttgaatca ccttatttcg atggcaatgt ctggcattac ctgcagtttc | 720 |
| cggtatcctg gcagctgaa ctcggatctt cgaaaacttc tgaccaacat ggtaccctat | 780 |
| aggaaacttc acttttttcgt accgggtatt gcgccgctaa catcgaagga agtcaatgc | 840 |
| tacagaagtc tctccgtttc ggagttagtc tatcaaattt ttgatgaaca aaacctcatg | 900 |
| gcagcttgct cgccatccag aggaaaatat ctaacggctg ctgccctctt ccggggacga | 960 |
| gtatctacca gaaatgtgga agaacaaatc gccaacgtaa ggcagaaaaa tcacggtacc | 1020 |
| ttctcgcatt ggatcccaaa taatgtcaaa tcagccattt gtgacattcc gcctgccgga | 1080 |
| atgaagatgt ctgcaacatt tatagcgaac accaccgcca tcactcagtt gtttcaacgg | 1140 |
| ttgctgaatc agtttggaac catgtatcgg aggaaagctt tccttcactg gtacacggga | 1200 |
| gagggaatgg aagaaaagga gtttgtcgac gccgagcaaa gcttgaggga gctgatcaag | 1260 |
| gagtacgaaa gtcaagaaga agcaggcccg gcaggatcta cgaagggttc gatgcttgat | 1320 |
| gacgaataa | 1329 |

<210> SEQ ID NO 6
<211> LENGTH: 1011
<212> TYPE: DNA
<213> ORGANISM: Aedes aegypti

<400> SEQUENCE: 6

| atgtccacca agactgacac cgggagcaag aaggccgtcg agtcaaacgg tggaagtgga | 60 |
| ttgtccgtat tcgggtcgaa gtcctccatt acacgggcgc tgaatctgca tggataccac | 120 |
| atgggcataa agatcgggaa gggatcgttt tcgtcggtcc ggttagccaa atacatcagc | 180 |
| aagaatcaga acgtccaaac gctggcctgt aaggtgatcg acgtccgcaa ggggactgaa | 240 |
| gaattcatca agaagttctt tccccgggag ctcagcgtgt tgatgaagat ccgccatcca | 300 |
| aacatcatca aaatccacag cattctgaag cgggaacgga tggtgttcat ctttatggat | 360 |

```
tacgccgaag gtggagacct gctgaagtac atcaacaaga acggaatcat caaggagacc      420
caagccaagc gatggtttgc gcagttggtc agtgccctgc aatatctgca ctcgatcgac      480
atcgcccatc gggatctgaa gtgcgagaac atccttattt cgaagaaggg aacagtccta      540
ctcgctgact tcggcttcgc cagggtctgc ggcgaagaga acgggacctt tcgaacacc       600 tactgcggtt cggcagccta cgcagctccg gaagtgatcc tcggtaaacc ctacaatccg      660
atgcgggctg acgtttggtc actcggaatc attctgttcg tgatgctcaa cgctgcgatg      720
ccttttgacg atcggaatct gaagaagctg gtcgaggacc attggagtcg aaacttcggg      780
ttcgaccaga ccgtggacaa acagctgagc gtggctgcca agcggacggt gtttgagttg      840
ttgaatccgg atccggcgga gagagtggag ctggagcagt tgaagggact gggatggatc      900
gacgaagact cgggtaagga aagaaaacga aggatgggag agctttgcgt gaggggagcg      960
agtaagggcg gccgaagtgg atcggggacc aagaccggat gtaattgttg a              1011
```

<210> SEQ ID NO 7
<211> LENGTH: 2512
<212> TYPE: DNA
<213> ORGANISM: Aedes aegypti

<400> SEQUENCE: 7

```
atgaagtccg agcaaatgcc gcctgctaaa cctatcgtct gcactgcaat gctgcaaatt       60
cgcgctccgg ccggtacggc aataacgcgt acgccagcga ccctccaaat ccgtgcgacc      120
acgcccacaa tagtatcgcg ccaaaccgca gccaccaaca cacgacggt taccaccaaa       180 acgatccgta gtcaaacacc ggccgtggtc tcggtagcag ctgctgcagc agcagcggcc      240
gctgcggcat ctggttccac ggccactcag gtcaagcaag tgacagcaat tagtaacagc      300
aatgtagtcg tcgcagcctc aacaccatca acggcacctg gtcttgtagt gacccgggaca    360 caaccgttgc cagcgttagc acttagtctct tccgccgtgg ccactttgaa taatgctagt    420
aatagtaata gttctacgag tttgatcagt acaagcatcc cttctacgac gaccgtagtt      480
gtcagtacgg ctcctagtat cagtactgca atcactagca gtattactag taataatagt      540
agtgccagtc aggtaactac tgctagcact agcagttctt ccaccacggt caccacttcc      600
agtagtaaat caagttcagg atcaaaatca cagggctcgt cggcgggcac gaaaaagaaa      660
gcaaatgcta gtgctgccgt gagttctgtt gatcctaacg atccgacagc agctaagaaa      720
gcagcctcta tgcaatcctc tttttatcag catcacgtgt cttcctcaat gtacggggat      780
gatgatatca acgacgttgc ggccatgggt ggtgtcaact ggcggagga aacccaacga       840 attctcggtt caacggaatt tgtggggaca cagattcgat cttgtaaaga cgaaatattt      900
ttgcacatgt cggcgctgca agcgaaaata cgggggattg tcgcgaggca cggactggag      960
gaaccgagca gtgaggtcgc agtactaata tcccatgcct gccaagaacg actgaaaaac     1020
atcgtggaaa agtggccgt agttgccgag catcgaatcg atattatcaa ggttgaccca      1080
cggtacgaag tgacgaagga cgtacggggg caaatcaagt tcctagaaga gttggacaag     1140
gcggaacaaa agcgacacga ggaacaggaa cgtgaaatgt tgatgcgagc agccaagtct     1200
cgatcaaaaa cggaagatcc ggagcaagct aaacttaagg ctaaggcgaa ggaaatgcaa     1260
cgagcagaga tggaggaact tcgacagcga cgctaatt tgacggccct gcaagccatt      1320
ggaccacgga aaaagcctaa actgaggag ggagcaacta cgactgttac ggttagttgt     1380
ccagcacttg tttcggtctt cacatgtttt tcaactccgt ttttctgttt tttttttagcc   1440
```

-continued

| | | | | | |
|---|---|---|---|---|---|
| tggtgcatcc | ggcattggag | tgggagcaag | cgggaagacc | gccacccgt | tgaggcctcg | 1500 |
| aatcaagagg | gtcaacttgc | gtgacatgct | cttctatctg | gaacaggaga | aggaaagctg | 1560 |
| cagaagtcaa | atgctctaca | aggcctacct | caagtgatcg | attgtggtgg | taaaacagct | 1620 |
| aaaaatggtg | ataaaaaata | tgacgatcgt | tctctgctga | agccgtgaac | ggcgcccaag | 1680 |
| gtaaggacca | accaccgatc | cacgccgcca | gcgaaggagg | tttaaactag | aaatccggtg | 1740 |
| gcaagtgtgt | ttcagcttgg | aagcgcgcga | aagaggtttt | ggcccaatca | aaatgcgttt | 1800 |
| catggtcagt | tcaggtcaga | tgtcaagagt | cagaggaaga | ttggagcaca | gtttgtgtaa | 1860 |
| aagtgagagc | gaatcatcag | gatgtttatg | tgtatgcgtg | tgtgcgtgat | ttttgagatt | 1920 |
| tttttgtaaa | tatttcaatt | ggccgctacg | gtggaatatc | aggaatcgtg | cgcatgagtg | 1980 |
| atgacgagaa | ggatttgccg | ggtagaccag | tttggtatgg | attcgccgac | cgaactgttt | 2040 |
| ttgacgtttt | atttaatttg | gaaaactaac | ttcgaaatca | agtgtacaga | aacaacaca | 2100 |
| ttatagggta | aagtgcacga | gcgagtctag | gtatgtaggt | aaaacagaga | agaaaggaaa | 2160 |
| aaataggtct | aaaatagtga | aaacagattt | aaaaacaatt | gtgtaattaa | ttttgagtcc | 2220 |
| tctagagctg | tgtgcttggc | ggaacaaaag | aaaaaaaaaa | ctggtcagcc | gcaagcattg | 2280 |
| tttttgtttg | tttatcattt | taagtctata | tcgataggaa | caaaataaaa | ctcaatagaa | 2340 |
| atcataaaaa | aacattaagg | aaaacaaaaa | tctgaaaatt | tcaaccgaaa | ggataaaaaa | 2400 |
| tagtttatat | atctcattgaa | tcgccgtttt | ctcggaaaca | aaaatcgata | tgttataaat | 2460 |
| tatattgacg | aacagtcaat | gagtaacaag | ctttgtttgt | gattatatca | ct | 2512 |

<210> SEQ ID NO 8

<400> SEQUENCE: 8

000

<210> SEQ ID NO 9
<211> LENGTH: 1659
<212> TYPE: DNA
<213> ORGANISM: Aedes aegypti

<400> SEQUENCE: 9

| | | | | | |
|---|---|---|---|---|---|
| ttttgccctg | caatcgatgc | gtgccttccg | gaatgcatat | ggagctctcc | tgcgacgcaa | 60 |
| attttccacc | aacatcggag | aaaatcgggc | agaggtgagt | tggttaaccg | tttgatccag | 120 |
| tccgaagact | tcaacatttc | cttgaatttc | cagaaaggat | tggttctggg | cctgtacgag | 180 |
| caggaaattg | aaacgacga | gcctcgcttg | actccagtgg | ccggccattt | cgatgccaaa | 240 |
| acggaaggac | agctcgtaaa | tctaatcaaa | gagtcaaatc | tgaaaggaaa | agttggacaa | 300 |
| gtcaaggtgt | tcaacaacat | cgatccggac | ttcggttcgg | tggccgttgt | aggactcggt | 360 |
| ttggaagggc | tcgggtacaa | tgagcttgaa | cagctggacg | aaggcctcga | aacgttcgt | 420 |
| atcgcgtctg | gtgtaggtgc | taagtgtcta | gcgaagcaag | gatgttcccg | gatttcagtc | 480 |
| gacccaatgc | aagcggcaga | acaagcagcg | gaaggaagcg | gtcttgccac | ctggaagtac | 540 |
| caggccaatc | gaatgaagtc | ggagcggatt | ccaacgccga | agttggagtt | gttcgattcg | 600 |
| ccggacggag | atgcatggac | gagagagcttg | ttcaaagctg | atgcgcagaa | tctagcacga | 660 |
| agcttatccg | atgcaccggg | aaatcagatc | actccgacgg | cctttgcgca | agcagctgtg | 720 |
| gacgctcttt | gccatgtgg | agttagcacc | gaggtgagaa | acatggactg | gattgagtcg | 780 |
| aaaagcctgg | gcagcttctt | ggcggtggcc | aagagctcgt | gtgaaccacc | aatcttcctg | 840 |

| | |
|---|---:|
| gaaatcagct actgtggaga acacgattca ggacgtccga ttatgctggt tggcaaagga | 900 |
| attacgttca acagtggtgg tttatgcctg aaggagccgc atggtatgtc acagtaccgt | 960 |
| gcgagtatgt ccggagcggc ctccatcgtt gccaccattc gagccgcggc agcgctttca | 1020 |
| cttccggtca atctagtagg cctcatccca ctgtgtgaga acatgccttc aggaatggca | 1080 |
| ttcaagccgg gagatgtcat tactaccctt aacggaaaga cggttgccat acacgacacc | 1140 |
| agcaatgcag gacgtctgat catggccgat acgttcatct acggccagaa tacattcaaa | 1200 |
| cccaaggtgg tgatggacgt tgcgacgctt acgaatggag taacacacgc actgggtgga | 1260 |
| gccgccagtg gagtattctc caactcggac ttcttgtgga agcagatgca gaaagccgga | 1320 |
| gccatcaccg gagaccgtgt gtggagaatg cccctgtgga agtactacac gcataaagtt | 1380 |
| acaaattata cgaatgtgga catcagcaac actggccagg gcaagggcag tgcctgtttg | 1440 |
| ggtgccgcat tcctgaaaga gtttgtcccg tgcgtggact ggattcatct ggacattacc | 1500 |
| ggcgtcggaa tgctgaagaa aggagtcggt attccgtacc tcgcggaaga gcgcatgact | 1560 |
| ggccgaccaa cgaggacgct ggtgcagttc ttgtaccaga tggcatgccc ggatgagcag | 1620 |
| gtgaagagcc tttcgaagga atcgtgcggt gcaaattag | 1659 |

<210> SEQ ID NO 10
<211> LENGTH: 1581
<212> TYPE: DNA
<213> ORGANISM: Aedes aegypti

<400> SEQUENCE: 10

| | |
|---|---:|
| aaggagatta ctcgcttgca gcgccaatat ctgaacatag ccaattcaac tgccgcttcc | 60 |
| aaagatgtcc agattatgcg atgtctggag aagaagctca agtacttgca acgggaaaag | 120 |
| acggaactca aaaccaagct taaggttgcg tacgctccct gccacgttcg acgatacgat | 180 |
| cgacaggttc aactggtgga agcccacgtt cgcgtgcagg atgatctggt cttgaaaatg | 240 |
| aacggccttc gaacggagat tcgtcacctg gaatcgcaaa tgaagcggct cgataaggag | 300 |
| aggaaggagc ttcagaaggt ttcgcagtcg gattacttct tctacaatcg ggttacgaaa | 360 |
| gctaagaaac gactagcgac gttggaagat cgattgtatc acctgaagaa gcggaaagct | 420 |
| acgaatatca ccaagaacca caaactgaag agcgtgatta aggatatgtt ggtggatagg | 480 |
| aagctgtttc accagcattg gagaaggatg atagacactt tggggtacga taagaagttt | 540 |
| ttgatcgata tgattgaaag gacgatactg gcgttcaacc aggggggagga gctgtgccac | 600 |
| aaaattgacg ccgtcaagaa tcacgctgca agagaagaga agtctcaacg acaggaaatg | 660 |
| atggagctac aacgaagaat caataacgac caaaagaatc atgagttttt gcgggtgaaa | 720 |
| ggcttccatc gggatatgtg cgatttggat ccaagagagg ttcgccgaag aaatatgatg | 780 |
| aaagacgatt acggaaggaa gcttgaactg taccaaaaaa tcatcgaaaa gacaaaactg | 840 |
| ttctgtggag ttgaagatat ctcgcatttg atttgagaagt atcaaaaaca ggaagacacg | 900 |
| ttttcgctc atttcaatta cctgaacgaa ttgaatcacc agtatgaaca gctgaactgt | 960 |
| atcctcatgg atttgtacac aagtgtgaat gacttgaagg aacagaagct tagaaaagaa | 1020 |
| gtaagccaag atcatgcttt caagcagctg cacgaaaagc tactaaagga gacagagaaa | 1080 |
| actcaaaaac tgcagtcaac ggtgaaatca acgattcgg agctccttga gcaatttgaa | 1140 |
| gaaattgacg aaatttttgtt ggatgtcggg tatgatcgat cggacgtgaa aaacctccta | 1200 |
| ggtgagcatc ggaaagtgac caaacacaac gtgaacgat tcctagcggc actgaaaatc | 1260 |
| aaactgaacg agcgtctggc ggtagtctac actcatctac aacccgagga agaaccagct | 1320 |

| | |
|---|---|
| ctgaggcgac ctgttgctcg cagctcgcag gaaattattc gcatcgaaga agttgtaact | 1380 |
| actcaacaat gtgcggaatg tgccgaggga caggacgtca ataagtacga tgaggccatt | 1440 |
| gtgctcccga aggagatgtc tgaaatccgg gagggaatga agcaaaggt taaagccccg | 1500 |
| gatatgcagt accggttgca taatttaagc aagtgcaagc ttcctcggtc gcggattctg | 1560 |
| gtcaataaga gataccaatg a | 1581 |

<210> SEQ ID NO 11
<211> LENGTH: 918
<212> TYPE: DNA
<213> ORGANISM: Aedes aegypti

<400> SEQUENCE: 11

| | |
|---|---|
| atggaatatt cgtcgacgaa aaatttgagt tcagacacat tcaacaacgc tctgtcctcg | 60 |
| cccaatgaat ggaaccgcaa agaggttaaa aaacaacttt cggagcgagg ttatctgatc | 120 |
| gggcaatcca tcggcgaggg ttcctactcg aaggtgtact actcggaata ccgtaaatca | 180 |
| ggccaacagc agcatttccc ggaacggaga gcatgcaaaa tcatcaatcg aaacaaaagt | 240 |
| tcaatggagt attcgcagtt ccttccgagg agatcaaaa cgatgatagc gctgtcccat | 300 |
| ccgaatatcg tttcggttta ttcggtgttt gaatttggtc cttatgtttg cattttcatg | 360 |
| gattattgcc ggtgcggaga tttactgcag aggatccaaa gccatgggaa attgtccgag | 420 |
| tcgaaagcta gactactctt tcggcagttg gcttccgctg ttcagcacat gcattcgcga | 480 |
| ggattctgcc atcgggacat taagtgcgaa acgtgttgc tctgcagccc atcgcatgtc | 540 |
| aagctgtctg actttacgtt tgcaaagaag tgtccctgcg aggaagcgtc gcaaaagctt | 600 |
| agcgccactt tctgcggctc tgcggcttat gcagccccgg agatcctcaa gggcattccc | 660 |
| tatcatccca aaggtatga catgtggtcg ttagggtgcg ttctgttcat aatggttacc | 720 |
| ggaacgatgc cattcgacga gcgcaatatt ccggaaacga ttgagcgaca ggaacggaaa | 780 |
| cagtacttct accccgatgg agtgaaacca aacccgacaa ttatcgaact gattgacagc | 840 |
| ctaatcgaac cggatgtgaa cgccagggca agcatcgatc aggtcgtgga ctgtgcgtgg | 900 |
| ttgcaggaag tggagtag | 918 |

<210> SEQ ID NO 12
<211> LENGTH: 807
<212> TYPE: DNA
<213> ORGANISM: Aedes aegypti

<400> SEQUENCE: 12

| | |
|---|---|
| atggcgcaaa gaaggattga tgagcaaatt ttcgatgaat atgaaccaac cgaggaggag | 60 |
| aaacattttg aatttaatat tcaaaaatac aatggcccaa ggaattctcg gtttgaaccg | 120 |
| catggtgaag gcagagcaaa attctttgct ggcggtcgat acgagggaca gtttagaaaa | 180 |
| ggcttacttc atgggaaagg tcgtttggta ttgcaagaca gccacaggta cgatgggcat | 240 |
| tggcgcaaag gcatgaagca tggcatgggt cgaatgtatt acccagactg ttcgcgatac | 300 |
| gaaggagagt tcagaaaaga ccaacggcaa ggtattggta tttattacta tccgaatggc | 360 |
| gcacgttatg atgggaattg gttcaagaac aagcgccacg gtgtaggaaa ttacgttttt | 420 |
| agccgcggag atgttacctt gaagggaaca tggatcgaag gaatcgctcg cggtcccgca | 480 |
| gagatcgtct ttgaagagta tcggttccat ggatattggg atgtagacaa acccagaggt | 540 |
| ccaggtagtt tcactttga cgccaaagtt atgatcagtg gaaagtactt cgtcgatgag | 600 |

```
aaagagggat gtgatgcaag ggaattggtg tggcaaccgt ttttgattga gaaatacgac    660
tattcaaagc taccactgga accccttcct tttccagtag acgagtcgga cgtgtcagac    720
ataagctctt ctgaagatga agattgtgat tcagaagggt cgtctaacaa ggaattactc    780
acgacgtttg tgtcggcca tgtttga                                        807
```

<210> SEQ ID NO 13
<211> LENGTH: 2142
<212> TYPE: DNA
<213> ORGANISM: Aedes aegypti

<400> SEQUENCE: 13

```
atggcttctc cagcatcatt cctaagctta gaaagcgatg ctagcgaaat tcgtggatca     60
tccatgcaga aaccgggcaa aggagaaccc gtcgacaacg atgagttcga gtcgtgggtc    120
aagtccaagc agctgctcaa accggatgat caactggatc taacggaggc cgagctgggt    180
gaagagattc ccaagcttct gtcaacggag aatcgacatc taccgaggaa tttggtgatc    240
tacaacttcc atgagggaac atacgaaccg gttccaccac cggaaaacac agtaactctc    300
ttggagtttg aaggaacttc tcttcataag gatacacccg aggcgaagga acaaattgcg    360
cgcaaaggaa ctgatgaact gaatgtcacc ttggataaac caccggaacc gagcccggaa    420
gaggaagtac cgccgccccc atcagaaact ccggacggtg aagatgccga gcgagaggaa    480
gatgaaggag aagccgatgg cgaagcgcag gaacaggaag aagaagttca ggctgctcca    540
gaggaggaag ctccgaagaa gaagttaacc aaccagttta acttttgcga acgcgctgcg    600
ctgactatag cgaatccatc caggtcggtc gatacgcaaa cgattccgcc gccccggtcc    660
acctatggat ccagcgtgct gcagtgggtt atttacgact cgtactccga ggactacgca    720
cagcagcagc gcgaaaagga gcgggaaaag gagaagaagc cgatgctgca caagcgtgat    780
gaaaaatcgc gcaaggacga caaggcaaag cagacggaag agttcaacaa gcgctatctg    840
caggcctgtc agattatcga gcggatggtg aaccagaaca tttacgacga aatcgcacaa    900
gattaccgct actgggagga tccttcggac gagttccgcg aggaagaggg caccctgctg    960
cctctgtgga agttctccta cgagaagacc aagaagatgt gcgtaactga tttgtgcttc   1020
aatacgctgt actacgattt gtttgctgtg tgcttcggaa cgttggattt catgaaacaa   1080
ggcaacgaag gagcagtgtg tttattcacg atcaaaaatc catccttttcc ggattacaga   1140 ataacgaccg agagtggagc catgtgctgc gatattcacc cgaagtatcc gtatctaatt   1200
gcggttggat tgtacgacgg gaacgtgatc gtttacaacc tacaggttgg caccaaggag   1260
ccggtctata tgtcccatgg cgtcaatggc aaacactcgg aatcggtgtg ggaactcaag   1320
tggggaccgg acatgcagga tggagagatt aacttcttca cggtttccgg agacgggcgg   1380
gtgtttaact gggtgttgat gcagaataag ctcgctatta cgacgattat atcgctgttt   1440
ttggacattg acacggttgg gggaccggat gggagcagtc tgaagttgaa gggttgcggc   1500
atgtgtatgg tgtttcatcc caataacccg agacgttttt ggttggaac ggaggaggga   1560 tacattttca agtgcagtac cgcgtatagc tccaaatatc tgatgaccta ttatgcgcac   1620 taccttttccg ttcaccgcat ggactacaac aaattcaact cgaacatttt cgcatcctgc   1680
agcggcgact ggcgcgtcaa gatatgggag gatatgagac ccgaaccgtt gttcatcttc   1740
gacctgggcg cttcggtggg cgatgtcaag tgggctccat actccagtac ggtgtttgcg   1800
gcggtcacaa ccgagggcaa agtgtttgta ttcgacctga gcgtgaacaa gtacaaagcg   1860
atttgtgtgc aggcggtcgt ctctaagcgg aagaacaaac tctctcggat tgccttcaat   1920
```

| | |
|---|---|
| cacaagctac cgttcatcat cgtcggggat gacaagggca caacaattac gctcaaactg | 1980 |
| tcgcccaacc tgcgcatcaa gacgaaggca ccgaagaaaa ccgtcccggt agatccacac | 2040 |
| tcgctggaag tacagaaact ggaccgattg ctgtcgctgg tgagggagct gccggaaggt | 2100 |
| gaactggtga aggagacggt ttccaccgta gcttccaact ag | 2142 |

<210> SEQ ID NO 14
<211> LENGTH: 278
<212> TYPE: DNA
<213> ORGANISM: Aedes aegypti

<400> SEQUENCE: 14

| | |
|---|---|
| ctgtgccggt tattcagctc gtacggcaac gtcaagtcaa cgaaaatcat cgtagatcgg | 60 |
| gcgggcgtca gcaaaggcta cggattcgta acgttcgaaa ccgaacacga ggcacaaaga | 120 |
| ctgcagagcg atggagactg tatcgtgctg agggaccgta agctaaacat agcaccagcg | 180 |
| attaagaagc aagtaagttg gcaccataca atctgcgcga cgaacggtgc cgtgtactac | 240 |
| gcagccacac ccccgacgcc gacgatcaac aacatccc | 278 |

<210> SEQ ID NO 15
<211> LENGTH: 273
<212> TYPE: DNA
<213> ORGANISM: Aedes aegypti

<400> SEQUENCE: 15

| | |
|---|---|
| agatcgagca ctgtttccga gcttatgata tcggcggaga agagttactt cggagagaac | 60 |
| acatgatgat attgttgcgg agttgtttca tcaagcacca agaagaggaa gtcgaagaat | 120 |
| cggttaagga catggtcgaa attcttatcc gtcgaatgga cgttgatcga gatggagcca | 180 |
| tttccttgga tgacttccga caatccgttc acaagtcacc agaacttcta gagtgcttcg | 240 |
| gccaggcact tccagatcgg gcccatgtat acg | 273 |

<210> SEQ ID NO 16
<211> LENGTH: 320
<212> TYPE: DNA
<213> ORGANISM: Aedes aegypti

<400> SEQUENCE: 16

| | |
|---|---|
| agccaaagga agtacggtca tcgatgggggt ggacacatcc agtatgtccc gcgaacagct | 60 |
| agaacagttt gcgctccggc ttcgcaacga gatggaacgg gaacgcgagg agcgaaactt | 120 |
| cttccagctg gagcgggaca aactgcgcac gttctgggaa atcacgcgca acagctcga | 180 |
| ggaagcgaaa gccgtgatac gcaacaaaga acgtgacgta gaggttgccc aagaacttgc | 240 |
| cgaccaggac acgaaaaatg tgatgcagga gatgaagcat ctgcagtacg agcatcagtc | 300 |
| gcacatcgga gagctgaaag | 320 |

<210> SEQ ID NO 17
<211> LENGTH: 254
<212> TYPE: DNA
<213> ORGANISM: Aedes aegypti

<400> SEQUENCE: 17

| | |
|---|---|
| cgcgccaaga agaagatcaa cgacatcttc ggcgagatcg aggactatgt ggtggagaca | 60 |
| accggattca tcgatgccct cccgacgatg gtggaaatcg tggacaaagc cgagtcggag | 120 |
| ctattccgga gctatgtgct gaaagtgtcc ggcatccggg aggtgctcgc ccgtgaccac | 180 |

```
atgaaggtgg ccttctttgg gcgcacctcc aacgggaaaa gttcagtgat caacgctatg      240
ctgcgggaca aaat                                                        254

<210> SEQ ID NO 18
<211> LENGTH: 308
<212> TYPE: DNA
<213> ORGANISM: Aedes aegypti

<400> SEQUENCE: 18
tatcctgggc agctgaactc ggatcttcga aaacttctga ccaacatggt accctatagg       60
aaacttcact ttttcgtacc gggtattgcg ccgctaacat cgaaggaaag tcaatgctac      120
agaagtctct ccgtttcgga gttagtctat caaattttg atgaacaaaa cctcatggca      180
gcttgctcgc catccagagg aaaatatcta acggctgctg ccctcttccg gggacgagta      240
tctaccagaa atgtggaaga acaaatcgcc aacgtaaggc agaaaatca cggtaccttc       300 tcgcattg                                                              308

<210> SEQ ID NO 19
<211> LENGTH: 222
<212> TYPE: DNA
<213> ORGANISM: Aedes aegypti

<400> SEQUENCE: 19
gttttcgtcg gtccggttag ccaaatacat cagcaagaat cagaacgtcc aaacgctggc       60
ctgtaaggtg atcgacgtcc gcaagggac tgaagaattc atcaagaagt tctttccccg      120
ggagctcagc gtgttgatga agatccgcca tccaaacatc atcaaaatcc acagcattct      180
gaagcgggaa cggatggtgt tcatctttat ggattacgcc ga                        222

<210> SEQ ID NO 20
<211> LENGTH: 375
<212> TYPE: DNA
<213> ORGANISM: Aedes aegypti

<400> SEQUENCE: 20
tggacaaggc ggaacaaaag cgacacgagg aacaggaacg tgaaatgttg atgcgagcag       60
ccaagtctcg atcaaaaacg gaagatccgg agcaagctaa acttaaggct aaggcgaagg      120
aaatgcaacg agcagagatg gaggaacttc gacagcgaga cgctaatttg acggccctgc      180
aagccattgg accacggaaa aagcctaaac tggaggaggg agcaactacg actgttacgg      240
ttagttgtcc agcacttgtt tcggtcttca catgtttttc aactccgttt ttctgttttt      300
ttttagcctg gtgcatccgg cattggagtg ggagcaagcg ggaagaccgc caccccgttg      360
aggcctcgaa tcaag                                                      375

<210> SEQ ID NO 21
<211> LENGTH: 367
<212> TYPE: DNA
<213> ORGANISM: Aedes aegypti

<400> SEQUENCE: 21
gcattcctgt tctcgttccc caaacacttg tggcgatttt gcgaacgcgg tcgtcttgaa       60
acgttgtgtc acaatctgac ttctatcctt tcacctggtg cgtggactcg aagcgtaaa       120 gccttaactc tactttattt gacccaagag agccgcaagg gacacaacaa atacgcattg      180 attttttatcg gatgtgagat tctcaacttt ttcatagtcc tcctgaacat gttcttgatg      240
aacttcttgt tcggaggttt ttgggccagt taccaaccgg ccattcaggc actgctttca      300
```

```
ctggacatga acgcctggac ttcgtataat tctctggtct ttccgaagct ggccaaatgt    360
gacttca                                                              367

<210> SEQ ID NO 22
<211> LENGTH: 259
<212> TYPE: DNA
<213> ORGANISM: Aedes aegypti

<400> SEQUENCE: 22
gccatttcga tgccaaaacg gaaggacagc tcgtaaatct aatcaaagag tcaaatctga    60
aaggaaaagt tggacaagtc aaggtgttca acaacatcga tccggacttc ggttcggtgg   120
ccgttgtagg actcggtttg gaagggctcg ggtacaatga gcttgaacag ctggacgaag   180
gcctcgagaa cgttcgtatc gcgtctggtg taggtgctaa gtgtctagcg aagcaaggat   240
gttcccggat ttcagtcga                                                259

<210> SEQ ID NO 23
<211> LENGTH: 403
<212> TYPE: DNA
<213> ORGANISM: Aedes aegypti

<400> SEQUENCE: 23
gcagcgccaa tatctgaaca tagccaattc aactgccgct tccaaagatg tccagattat    60
gcgatgtctg gagaagaagc tcaagtactt gcaacgggaa aagacggaac tcaaaaccaa   120
gcttaaggtt gcgtacgctc cctgccacgt tcgacgatac gatcgacagg ttcaactggt   180
ggaagcccac gttcgcgtgc aggatgatct ggtcttgaaa atgaacggcc ttcgaacgga   240
gattcgtcac ctggaatcgc aaatgaagcg gctcgataag gagaggaagg agcttcagaa   300
ggtttcgcag tcggattact tcttctacaa tcgggttacg aaagctaaga aacgactagc   360
gacgttggaa gatcgattgt atcacctgaa gaagcgggaa gct                     403

<210> SEQ ID NO 24
<211> LENGTH: 339
<212> TYPE: DNA
<213> ORGANISM: Aedes aegypti

<400> SEQUENCE: 24
ctgtcctcgc ccaatgaatg gaaccgcaaa gaggttaaaa acaactttc ggagcgaggt     60 tatctgatcg ggcaatccat cggcgagggt tcctactcga aggtgtacta ctcggaatac   120
cgtaaatcag gccaacagca gcatttcccg gaacggagag catgcaaaat catcaatcga   180
aacaaaagtt caatggagta ttcgcagttc cttccgaggg agatcaaaac gatgatagcg   240
ctgtcccatc cgaatatcgt ttcggtttat tcggtgtttg aatttggtcc ttatgtttgc   300
attttcatgg attattgccg gtgcggagat ttactgcag                          339

<210> SEQ ID NO 25
<211> LENGTH: 266
<212> TYPE: DNA
<213> ORGANISM: Aedes aegypti

<400> SEQUENCE: 25
gcgcacgtta tgatgggaat tggttcaaga acaagcgcca cggtgtagga aattacgttt    60
ttagccgcgg agatgttacc ttgaagggaa catggatcga aggaatcgct cgcggtcccg   120
cagagatcgt ctttgaagag tatcggttcc atggatattg ggatgtagac aaacccagag   180
```

```
gtccaggtag tttcactttt gacgccaaag ttatgatcag tggaaagtac ttcgtcgatg      240
agaaagaggg atgtgatgca agggaa                                          266

<210> SEQ ID NO 26
<211> LENGTH: 312
<212> TYPE: DNA
<213> ORGANISM: Aedes aegypti

<400> SEQUENCE: 26
ggatatgaga cccgaaccgt tgttcatctt cgacctgggc gcttcggtgg gcgatgtcaa      60
gtgggctcca tactccagta cggtgtttgc ggcggtcaca accgagggca aagtgtttgt     120
attcgacctg agcgtgaaca agtacaaagc gatttgtgtg caggcggtcg tctctaagcg     180
gaagaacaaa ctctctcgga ttgccttcaa tcacaagcta ccgttcatca tcgtcgggga     240
tgacaagggc acaacaatta cgctcaaact gtcgcccaac ctgcgcatca agacgaaggc     300
accgaagaaa ac                                                         312

<210> SEQ ID NO 27
<211> LENGTH: 380
<212> TYPE: DNA
<213> ORGANISM: Drosophila melanogaster

<400> SEQUENCE: 27
gcggatggtg aatgcgtggt actaagagat cggaagctga acattgcacc ggccatcaaa      60
aagcagccca atcctctgca gtcaattgtg gccacaaacg gagccgtcta ctataccacc     120
acgccgccgg caccgatcag caatatamacc atggatcagt tcgcagccgc tgtatatccg     180
ccagccgctg gagtgccagc catctaccca ccttcagcca tgcaatatca gccattctat     240
cagtactaca gtgtgccaat gaatgtaccc accatttggc ctcagaacta ccaagaaaac     300
cattcgccat tgctgcactc gccgacgtca aacccgcatt cgccacactc ccagtcgcat     360
ccacaatccc catgctggag                                                 380

<210> SEQ ID NO 28
<211> LENGTH: 320
<212> TYPE: DNA
<213> ORGANISM: Drosophila melanogaster

<400> SEQUENCE: 28
ctggagaatg cccgcttcaa ctacgtgtat atgaaggaca ttgctcgcct ggcaaaggac      60
tcgatcttct cgcataacga gctgattagc attgtaatgc tctaccataa gtttgtgctg     120
gtcaatgggc cgagagcaaa gtacatgacc attcagcaac tctctgcgct gatggagctc     180
ttgtttgaga tcgtggatcg cgatctcatt gcgaccattg tgtatagaat agcccataca     240
ccaggttcca ggcctcctga cttcttttcc gacaagcata tacacttgga gtcctttgtg     300
cggcttttca ccgtatactt                                                 320

<210> SEQ ID NO 29
<211> LENGTH: 302
<212> TYPE: DNA
<213> ORGANISM: Drosophila melanogaster

<400> SEQUENCE: 29
gcctcaagac gcgcaacact cggctggaaa agaaggtgaa gggtctcact tgggaggcgg      60
aaactctgat cctgcgcaac gactcgctgg tggcagaacg ggagggcctg aaggagcgtt     120
tcaacgacgt gatcgtcgag ctgcagcaga agacaggact aaagaatgtc cttctggagc     180
```

| | |
|---|---|
| gcaagattgc cgcattgatg cgcgaggatg agaagcgcag cattgtccta cacgaaacga | 240 |
| ttgccacctg cgctcccaat ttcgccgaaa agttaaccag cttggatgaa cgggtgggca | 300 |
| ac | 302 |

<210> SEQ ID NO 30
<211> LENGTH: 349
<212> TYPE: DNA
<213> ORGANISM: Drosophila melanogaster

<400> SEQUENCE: 30

| | |
|---|---|
| cgcggtgtca gcgttaaaaa ccaaatttgg tccacacttg ctaagtgcgc agaagatttt | 60 |
| aaaccagtta aaatcaactc tgatatgccc tttcatagag aaagtaagtc gtcttatcga | 120 |
| tgagaataag gagagaagag ctaacttgaa tgccgaaata gaggactggt taatactaat | 180 |
| gcaagaggat agagaagcgc ttcaatattg tttcgaagaa ctgactgaaa tgacacaaag | 240 |
| agtaggtcgg tgcgttttga acgaccagat aaaaacgtta ataccctcgt ctgtgctatc | 300 |
| attctcgcaa ccatttcacc cggaattccc agcacaaata ggccagtac | 349 |

<210> SEQ ID NO 31
<211> LENGTH: 517
<212> TYPE: DNA
<213> ORGANISM: Drosophila melanogaster

<400> SEQUENCE: 31

| | |
|---|---|
| gcttgacctc tctaataatg gaggccctgg tggagcagta tccggataat ttactctgca | 60 |
| actatgtgac cattccgtcg ccgaatatgt cgcaggtggt tgtggaaccc tataatgccc | 120 |
| tacttagtac tcccgccttg gttaacaatt cgcatttaac cttctgcctt gataacgagg | 180 |
| cactgttcca aatctgcaat agaaacctga agctcaagat gtccggctac gagcacatta | 240 |
| accacatagt agccctgacc atgtcgggta taaccacttg cctgcggttt cctggccaac | 300 |
| tgaatgctgg attgcgcaag atctatgtaa atatggtgcc attcccgcgg ctgcacttcc | 360 |
| tcataccggg attcgcacca ttggtcactt gcaagcagca gcagttcagc aagggtaccg | 420 |
| tttcggagct ggtgcagcag atcttctaca gtaataatct gctctgtgcc atcgatcttc | 480 |
| gaaagggcaa actgctgacc gctgctggaa ttttccg | 517 |

<210> SEQ ID NO 32
<211> LENGTH: 308
<212> TYPE: DNA
<213> ORGANISM: Drosophila melanogaster

<400> SEQUENCE: 32

| | |
|---|---|
| tgcgagcatc gaacaagcta tcatctgcac aacgacgaac gttgtgtgat gaagaacgat | 60 |
| atgagggtca cgatgatgtt cctcaacgat ctcgagattg ccgactatgg atcatcggat | 120 |
| gacgagaccg gcttttatcg caagcgccgg gcagagaaca tcgacgagga gagaaaggtg | 180 |
| gctcgtctgg aatcggtgaa tgatacggcc ttgctagcca tctccggtcg aaagcgcccg | 240 |
| ggagaacaac tagccccaga atctgctcca agtggttcga aagtcgccaa attgaccggt | 300 |
| gctccgat | 308 |

<210> SEQ ID NO 33
<211> LENGTH: 529
<212> TYPE: DNA
<213> ORGANISM: Drosophila melanogaster

<400> SEQUENCE: 33

```
gcaacaagcg caagcaggat cgcactcagg tacccaaact ggatctgtac gactcaccgg        60
atgtggatgc ctggacgagg ggtctcttca aggcggaatc tcagaacttg gctcgaagat       120
tgagcgattc gccggctaat cagatgaccc ccaccatatt cgcccaatcg gcggtggatg       180
ccctgtgtcc gtgcggcgtt tccgtggagg tgcgatccat ggattggata gaaatgaatc       240
atctcaattc gtttctaatg atagccaaag gcagctgcga gccaccggtg gtcctggagg       300
tcagctactg cggcacagca cccgaggatc ggcccattct gctgttgggc aagggtttga       360
cctacaacag tggcggattg tgcctgcggc aaaaggattg cctgcatatg taccgcggct       420
gcatggcggg agcagccgtt tgtgtggccg ccgttcgagc tgcggcagcc ctttccctgc       480
ctgtaaacat cacggccgta ctgccgctct gcgagaatat gccatcggg                   529
```

<210> SEQ ID NO 34
<211> LENGTH: 328
<212> TYPE: DNA
<213> ORGANISM: Drosophila melanogaster

<400> SEQUENCE: 34

```
tcggtgaatc gcctgtttga ggatatagtt aacctgaaaa aggataactc caacacgctg        60
caggaccaac tggatcagat ttccagtctg gagaacaagg tgcgtaacaa acaggaatcc       120
aacatggaac tgcacaaggc gcgggaaaac aacgatgcac gtttggagaa tcttctacag       180
ggcgtggaga cggtctgcga gatgtgttcc atagatgcca gtccgctgac caaactcctt       240
ggtgaccaca cccacgtcaa tctggttaat gtcaatcgat tcttgaagct gctcgagaca       300
agggtccagg agctgacggc tagtgttt                                          328
```

<210> SEQ ID NO 35
<211> LENGTH: 320
<212> TYPE: DNA
<213> ORGANISM: Drosophila melanogaster

<400> SEQUENCE: 35

```
gcccacaaca tgtccgtcta tcgcattgac ttcaatcgct tcaacagcaa catcttcgtg        60
tcctgtggcg ccgactggat ggtcaaggtg tgggaggata tgcgtccaga tccgctgttc       120
atattcgatc ttggtgccgc cgttggcgat gtcaagtggg caccttactc gagcaccgtc       180
ttcgcagcgg tgaccaccga gggcaaggtc cacgttttcg acctaaatgt gaataagtac       240
aaggccatct gcatccaggc cgtggtgccc aagcgaaaga acaagctcac caggttatcc       300
ttcaacgaga agctcgcctt                                                   320
```

<210> SEQ ID NO 36
<211> LENGTH: 460
<212> TYPE: DNA
<213> ORGANISM: Aedes aegypti

<400> SEQUENCE: 36

```
ggtcaagccg tggtcaatga atactcacga ttgcacaatc tgaacatgtt tgacggtgtg        60
gagttgcgca gtacgacgcg ccagtccgga tgatagactt tttacacgat cagcacgacc       120
cactgcgctg tggcaaaggt cgaaccgaaa caagaataaa gcacgaagat cagatgatcg       180
atttgacgga agaagcaatc gaatacaaag aagaatcgga acgaagaaaa ctctaaagca       240
tcgcatattt acaaagcata acggaaaacc cgcaagttca aactagtgat tagtgtaaga       300
tgaagcaaag cagaaatgtg gtatgtagat ttttcgacgt tagtttacaa agataagaaa       360
```

```
tgaggttgga cacacaatcg tgggtattcg tctgagttcg tcacaactgc accggaaact      420
gtgaaacaga atagagccaa cctgtgcgcg gagaatgttg                            460

<210> SEQ ID NO 37
<211> LENGTH: 463
<212> TYPE: DNA
<213> ORGANISM: Aedes aegypti

<400> SEQUENCE: 37
gcaaatgctg tttaacgata atagcgacat gcagccattc tggggctacc acgtgtagct       60
ctacttgtga gacagcgttc ctaaagagtg tgaaagtgca aacaagtgat gaaaccaata      120
gtgcaaagca agtttagagg gaaaatttaa aaaaatgcaa aacagcagta gtacttaact      180
tttaagattg tgtttcgaaa gccgaagtgt gttccatctg ccaccggaaa aaaacgacga      240
cagcagaatc atcaacaagc aacatccatc cgaaaaaatc cgggaaaccg gatcttcaac      300
caaccatcct acaatctaca aaccagagat tatatctctt caatcgtttc cgacatcggt      360
cggtttcggt gcccaaaatg atctgataaa cacttatctc tctgtagctt gcatgccatt      420
gcgagcgtat tttggtagct ggccgttgcc aaacggctcc gac                        463

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgtcgtagaa ccgtacaac                                                   19

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caggcaggtg gtaatcc                                                     17

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggtcaagccg tggtcaatga at                                               22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
```
caacattctc cgcgcacagg                                          20

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gcaaatgctg tttaacgata atag                                     24

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cggagccgtt tggcaacgg                                           19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cccttacgct gaagagatgc                                          20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggcacagcac atcaaagaga                                          20

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acctggctta tcgaa                                               15

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
taaaacgacg gccagt                                              16

```
<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tttcaagcaa ccggtgacag                                            20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttgagggacg ttttggaagc                                            20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcaaaactga ccatcctgca                                            20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccgttcttgc agtttcagct                                            20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctgtgccggt tattcagctc                                            20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gggatgttgt tgatcgtcgg                                            20
```

```
<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ttgctggacg agaaggaagt                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
actgagctgg ttggtgaaga                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agatcgagca ctgtttccga                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgtatacatg ggcccgatct                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cgcaaggatc ggaaaccaat                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
catgctgtag atcgggttgc                                              20
```

```
<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aaaggagcga aggagaccaa                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aggtagtgtt tcagggcctc                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
agccaaagga agtacggtca                                              20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cgcgccaaga agaagatcaa                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
attttgtccc gcagcatagc                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gataccgaaa tgtgcacgct                                              20

<210> SEQ ID NO 66
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66 ccggttctttt gtcactgcaa                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
caatgcgaga aggtaccgtg                                               20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gttttcgtcg gtccggttag                                               20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ttggcttggg tctccttgat                                               20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tggacaaggc ggaacaaaag                                               20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cttgattcga ggcctcaacg                                               20

<210> SEQ ID NO 72
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gcattcctgt tctcgttccc                                                     20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tgaagtcaca tttggccagc                                                     20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
catcgggtgt tgcttctacg                                                     20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tcaaagtaca cgtgctgcag                                                     20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gccatttcga tgccaaaacg                                                     20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tcgactgaaa tccgggaaca                                                     20

<210> SEQ ID NO 78
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 78
aacacttcaa cacgtgtcgg                                                  20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tcgtacactt cagcggagtt                                                  20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gcagcgccaa tatctgaaca                                                  20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ttcccgcttc ttcaggtgat                                                  20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ctgtcctcgc ccaatgaatg                                                  20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ctgcagtaaa tctccgcacc                                                  20

<210> SEQ ID NO 84
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 84
atcgtctatg gccggcttta                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tagcgctatg atgtcgtcgt                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
agcgatgcag gacgagatta                                              20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cgtgggccag tttcttatcg                                              20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ttgggcatgc ttcactgatg                                              20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
atcgtcggag tatcgctgtt                                              20

<210> SEQ ID NO 90
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 90
gccgtttcca ggacaacttt                                                   20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gtagtaatcc cgctctgcct                                                   20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggaacggtga aatcgatggg                                                   20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ttcactgctg tcgttgtgtg                                                   20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cagcgacgaa ccacaatgta                                                   20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gcttatcgcc gatggttacc                                                   20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 96
tcaagcaagt gctggacaac                                                 20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tgccttcagg tcgttctctt                                                 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cagtagcttt ccgtccatgc                                                 20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gaccagcgga taaatcgcag                                                 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gcgcacgtta tgatgggaat                                                 20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ttcccttgca tcacatccct                                                 20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ttggcgaaat tctgcaagct                                              20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
agccgaaacg tttgcttcat                                              20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ggatatgaga cccgaaccgt                                              20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gttttcttcg gtgccttcgt                                              20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
aataccagca cgctctctca                                              20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
attgcatcgg tggcaagttt                                              20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gctacttgga tttgggcgac                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
atcgcttcgg acaggatgat                                              20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tttgaacccg gaaaaggcag                                              20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ttcgacgaaa tcctcccaca                                              20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gatgaaactg ccgccactag                                              20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ttgccgaacc gttggaaaat                                              20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
aagacttggg aagaggacgg                                               20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ttctctagca gctggatccg                                               20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ttgctcatac gctccattgc                                               20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ttgctcctga acggtgagat                                               20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gaccgatcct gcaaaagtcc                                               20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tttgctcctg ggtgtagagg                                               20

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120

```
acacttcgct cattccac                                            18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
accttgctgt ctccatcc                                            18

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cgatgtggac tatacggaaa c                                        21

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ggattacttg acggtgcttc                                          20

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ggtattcgtc ggtggtatca g                                        21

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gcctcgtgtt cggtttcg                                            18

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
aaggagtacg aagagaagaa g                                        21
```

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
cggaagcggt tcattagg                                                 18

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gtcgtttggt gcggcgtttg                                               20

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ccttgttgtc ctcctcatcc ttgg                                          24

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
cagcaggata cggtcttc                                                 18

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gaataggtcg gattgttgg                                                19

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gcggcggatg cgattctc                                                 18

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gactcttggc ggaacgatag c                                              21

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gagcatcagt cgcacatc                                                  18

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tccttctctc gcagtaacc                                                 19

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
aagcacaaca ccaggaac                                                  18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gaaaccatca gccaaagc                                                  18

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ccgtgcttga gttgatac                                                  18

```
<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
attggaatct gatggtgag                                                  19

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gaacaccacc gccatcac                                                   18

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cctgcttctt cttgactttc g                                               21

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
cggtggaagt ggattgtc                                                   18

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
cgttctgatt cttgctgatg                                                 20

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gagcagagat ggaggaac                                                   18

<210> SEQ ID NO 145
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
caggcgtaac agtcgtag                                                 18

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
tggctttggt tcattgtg                                                 18

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
tatccgatgt tggcttcc                                                 18

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
acggtgccta tctgagaag                                                19

<210> SEQ ID NO 149
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ggatgctgat gaacgctac                                                19

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
cgtctggtgt aggtgctaag tg                                            22

<210> SEQ ID NO 151
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
tgcttgttct gccgcttgc                                                  19

<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ttcgcatacg gagtgttac                                                  19

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ccttgtggat gtagtctcg                                                  19

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ttcgcagtcg gattacttct tc                                              22

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
tggttcttgg tgatattcgt agc                                             23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
tgcgttctgt tcataatggt tac                                             23

<210> SEQ ID NO 157
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 157
gtcgggtttg gtttcactcc                                              20

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
agttctcctt ccgacatc                                                18

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gtaagccgca cattcatc                                                18

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
cgccaccaga tgtcctaatg                                              20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
cagttgttcc gattgcttcc                                              20

<210> SEQ ID NO 162
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
tgttggatga tgttgtgaga tgtg                                         24

<210> SEQ ID NO 163
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 163
atcgtcggag tatcgctgtt c                                              21

<210> SEQ ID NO 164
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ccagtcagag ggcgaatg                                                  18

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
cttctccgtc aggtcatcc                                                 19

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
cacagaggag gaagtaattg                                                20

<210> SEQ ID NO 167
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cactattgga ctgctaacg                                                 19

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gtatatgtcg cctcggttc                                                 19

<210> SEQ ID NO 169
<211> LENGTH: 18
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 169
gggttgtatc ggtgttcc                                                        18

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gttgctcttc gtcattattc c                                                    21

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
aaatccattg ccatctttgc                                                      20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gcggagatgt taccttgaag                                                      20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gaaactacct ggacctctgg                                                      20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
actcatacac tcgtttcaag                                                      20

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 175
tccatatccg aagcactc                                                18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gaagatgccg agcgagag                                                18

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gaccgacctg gatggattc                                               19

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
cggagccaag gaggtcatc                                               19

<210> SEQ ID NO 179
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
acagcagcag aagcagagg                                               19

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
ccagagcaac cgagagtatg                                              20

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
cgacgaaatc ctcccacag                                            19

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
ttaagattgt caccttcacc                                           20

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cgttgtagat gttctgtcc                                            19

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
tgtagttcgg tatcgttcgg                                           20

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tcggcattcc ttcgttcg                                             18

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
acaacagagc ctaagactat c                                         21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
cgacaatcat attctcacag c                                                    21

<210> SEQ ID NO 188
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
tggacgataa tgctcaac                                                        18

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
gaggcgaatg gagttatg                                                        18

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gcggatggtg aatgcgtggt                                                      20

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
tggggattgt ggatgcgact g                                                    21

<210> SEQ ID NO 192
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
ctggagaatg cccgcttcaa ctac                                                 24

<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193

```
ggtgaaaagc cgcacaaagg ac                                          22
```

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194

```
gcctcaagac gcgcaacact                                             20
```

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195

```
gttgcccacc cgttcatcca                                             20
```

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196

```
cgcggtgtca gcgttaaaaa                                             20
```

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197

```
ctggcctatt tgtgctggga                                             20
```

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198

```
gcttgacctc tctaataatg g                                           21
```

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199

```
gaaaattcca gcagcggtc                                                  19
```

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 200

```
tgcgagcatc gaacaagcta                                                 20
```

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 201

```
atcggagcac cggtcaattt                                                 20
```

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 202

```
gcaacaagcg caagcaggat                                                 20
```

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 203

```
cagagcggca gtacggccgt                                                 20
```

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 204

```
tcggtgaatc gcctgtttga                                                 20
```

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 205

```
aaacactagc cgtcagctcc                                                 20
```

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
gcccacaaca tgtccgtcta                                                 20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
aaggcgagct tctcgttgaa                                                 20

<210> SEQ ID NO 208
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tacggcacac taatacccaa tc                                              22

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tgctctttac cgtgccatag                                                 20

<210> SEQ ID NO 210
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
cgcattctcg gtctacgata aa                                              22

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
cttcatcctc gctctcaaag aa                                              22

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
gaggcgatga cccaactaaa                                                   20

<210> SEQ ID NO 213
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tctcgctcat ctccattctt tc                                                22

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gtccttcaat gtctctccat acc                                               23

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
caatccaggc cgtagattag tt                                                22

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
tccggcttga cctctctaat a                                                 21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
cgacggaatg gtcacatagt t                                                 21

```
<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
caagaatggc tcctggattc t                                          21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tcgtcgttgt gcagatgata g                                          21

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
cctgactgga gatcgtttat gg                                         22

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
gctgatgtcg aaggtgagat t                                          21

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
aagtttcagc agcaggagag                                            20

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
acaggcgatt caccgaatta t                                          21

<210> SEQ ID NO 224
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
atatgcgtcc agatccgctg                                                       20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
gtcgaaaacg tggaccttgc                                                       20

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000
```

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240
<211> LENGTH: 687
<212> TYPE: DNA
<213> ORGANISM: Drosophila melanogaster

<400> SEQUENCE: 240

```
atgcacaaaa tagcagcagc gccgcctcca tcggcaacgc ccggcggagg actggagacg      60
cccctggcgg cgccaaaata cggcacacta atacccaatc gcatctttgt gggtggcatc     120
agcggcgata ccaccgaggc tgatctaacc cgcgtcttca gcgcctatgg cacggtaaag     180
agcaccaaaa tcatcgtgga tcgagcaggt gtgagcaagg gctacggatt cgtcaccttc     240
gagacggagc aggaggcgca aagactgcaa gcggatggtg aatgcgtggt actaagagat     300
cggaagctga acattgcacc ggccatcaaa aagcagccca atcctctgca gtcaattgtg     360
gccacaaacg gagccgtcta ctataccacc acgccgccgg caccgatcag caatataccc     420
atggatcagt tcgcagccgc tgtatatccg ccagccgctg gagtgccagc catctaccca     480
ccttcagcca tgcaatatca gccattctat cagtactaca gtgtgccaat gaatgtaccc     540
accatttggc ctcagaacta ccaagaaaac cattcgccat tgctgcactc gccgacgtca     600
aacccgcatt cgccacactc ccagtcgcat ccacaatccc catgctggag tatcgaggat     660
ctgagggata cttttgccga ggtatag                                         687
```

<210> SEQ ID NO 241
<211> LENGTH: 735
<212> TYPE: DNA

<213> ORGANISM: Drosophila melanogaster

<400> SEQUENCE: 241

| | |
|---|---|
| atgaaggacc tggacggctc cttggacact ctggagaatg cccgcttcaa ctacgtgtat | 60 |
| atgaaggaca ttgctcgcct ggcaaaggac tcgatcttct cgcataacga gctgattagc | 120 |
| attgtaatgc tctaccataa gtttgtgctg gtcaatgggc cgagagcaaa gtacatgacc | 180 |
| attcagcaac tctctgcgct gatggagctc ttgtttgaga tcgtggatcg cgatctcatt | 240 |
| gcgaccattg tgtatagaat agcccataca ccaggttcca ggcctcctga cttcttttcc | 300 |
| gacaagcata tacacttgga gtcctttgtg cggcttttca ccgtatactt caccaaagat | 360 |
| cttcagctga aaatggaatt cgcattctcg gtctacgata aaagcgattc caagcagttg | 420 |
| aatggcgagc aagttgggtt cttcgtcggc aagttctttg agagcgagga tgaagacgaa | 480 |
| tccattgagc tgcgcttgga catgaaggag atgctgttcc tcaaattcga cttggacaag | 540 |
| gataccaaca ttgggggttga tgagtactac gaggtggtcc gccgacagcc catgctgctg | 600 |
| gagtgctttg gtcgcgtgtt tcccccgaat ccccagatgg aggtccttgc gctgtgcgcc | 660 |
| aatgtaatgt cttggtttga cgattcgccc aatcccagga ttatgataaa accagacggc | 720 |
| ggcaaggcca gctag | 735 |

<210> SEQ ID NO 242
<211> LENGTH: 1440
<212> TYPE: DNA
<213> ORGANISM: Drosophila melanogaster

<400> SEQUENCE: 242

| | |
|---|---|
| atgccgccta aagggaaaaa gggcaaaaaa ggcaaaaaat tgccagtgct catcgatggc | 60 |
| gtggacacct cggcgatgac tcgcgaccag ctggaggcat ttgctctccg gctaaaagcg | 120 |
| gaaatggatc gtgagcggga ggagcgtaac tacttccagt tggagcggga caagattcgc | 180 |
| actttctggg agatcacgcg ccagcagctg gatgagaccc gctacgagct gcagcagaag | 240 |
| gacaaggaga tcgaggccac gcaggatctg gcggatatcg ataccaagca tgtgatgcag | 300 |
| cagatgaagc atctgcagtt tgagaaccac aataggctcg gtgaggttcg ggctgaggcg | 360 |
| atgacccaac taaagctggc gcaggagcac catgttctgc aggaaaacga gcttcagcgg | 420 |
| gacaagcgac agttgcgccg aatgctgcgc gaaagaatgg agatgagcga gatgcagctg | 480 |
| cgccaaatgg aggctcactt caatgagaaa ctgctagagc agcgcatcac cttcgaacgc | 540 |
| gagcgcaagg acaacgagat gctgcacgag gagaaaatga tcgagcagaa ggccaagcta | 600 |
| gacctttcct acggcacaca aatgttcgag gtagaggagc gaaagaacca gcagataaag | 660 |
| gacctacagg accaccatga cctagccttt aacgatatga gaactatta caacgatatc | 720 |
| acgcttaaca acctggcgct aattggcagc atgaaggagc agctagagca tctgcgcaag | 780 |
| caggccgaga gatccgatag aatcgccgca gacacggcag ctgagaatcg gcgactgaag | 840 |
| gagcctttgg agcatgccaa tatccagttg aacgagtatc gtcgcaaact ggagttctac | 900 |
| gagcgggata gcagcaatt gagtcgcctc aagacgcgca acactcggct ggaaaagaag | 960 |
| gtgaagggtc tcacttggga ggcggaaact ctgatcctgc gcaacgactc gctggtggca | 1020 |
| gaacgggagg gcctgaagga gcgtttcaac gacgtgatcg tcgagctgca gcagaagaca | 1080 |
| ggactaaaga atgtccttct ggagcgcaag attgccgcat tgatgcgcga ggatgagaag | 1140 |
| cgcagcattg tcctacacga aacgattgcc acctgcgctc ccaatttcgc cgaaaagtta | 1200 |
| accagcttgg atgaacgggt gggcaacatc atcgatgaga agaacaagat aatccttgac | 1260 |

```
ctgcgctatg aggtaactaa ggcgcgaaag gcacacgacg atctactgga aacctacgag     1320
tgcaagctca agcaatatgg tgtgcccact gacgagttgg gcttcaagcc catcaggaat     1380
cgggaccaac agcagctgta cgtgtgcggt cctgcgggaa taatcaccga gaataagtag     1440
```

<210> SEQ ID NO 243
<211> LENGTH: 2157
<212> TYPE: DNA
<213> ORGANISM: Drosophila melanogaster

<400> SEQUENCE: 243

```
atggcggaat ctgactccgg agaaagtacg tcgtcggtgt cctcgtttat atcctcatcg       60
tcgtcttcgc gattaagtga gtttgtggac gcaaagacag aactgcagga tatatatcac      120
gatttgagta attacctgtc caatttccta accattttgg aggagactgt cctgttaaaa      180
gatcgacaaa tgctggagca cctgtgcgcc ttctccagca gggtggaggc cattgcaaag      240
gttctttcac gtgatcgaat gaaggtggca ttttttggac gcacctcaaa tggaaaaagt      300
gccgtgatca atgcacttct gcatgaaaaa atcctgccca cgcgccatgg ccataccacc      360
agctgttttt gtcaagtgca agctaatggc tcgaatgaaa ccgagcacgt aaaggtcgag      420
caggaggatg agcatatgga actgagtgcc ctaagccaac tggccagtgc acattctcct      480
ggggccctaa aaccctcaac tctgctgcag gtcaatatgg ccaagaaccg ttgctcgata      540
ttggattacg atgtggtttt gatggataca cctggagtgg atgtaacagc gcaactggac      600
gattgcctag atagctactg catggatgcg gatgttttca ttctagttct caacgccgag      660
tccactgttt cgcgcgtgga aaggcagttc ttcaaggacg tggcatccaa actctcgcgt      720
ccaaatctct ttatactcaa caatcgatgg gataaggcca gcagtctgga ccggaaaatg      780
gagcagaagg taaaggatca gcatatggaa cgttgcgtta acctgctcgt ggatgaatta      840
ggtgtttatt caactgcaca ggaagcgtgg gaaaggatct atcatgtttc agcactggag      900
gcattgcata aaggaatggg tcagattacg aatccctcgg acaaaccca acagcgatat      960 caggagtttc tgcgtttcga aaatgatttt tcgaattgcc tcgcggtgtc agcgttaaaa     1020
accaaatttg gtccacactt gctaagtgcg cagaagattt taaaccagtt aaaatcaact     1080
ctgatatgcc ctttcataga gaaagtaagt cgtcttatcg atgagaataa ggagagaaga     1140
gctaacttga atgccgaaat agaggactgg ttaatactaa tgcaagagga tagaagcg      1200 cttcaatatt gtttcgaaga actgactgaa atgacacaaa gagtaggtcg gtgcgttttg     1260
aacgaccaga taaaaacgtt aatacccctcg tctgtgctat cattctcgca accatttcac     1320
ccggaattcc cagcacaaat aggccagtac caacgctcgt tatgtgccca tttggataaa     1380
cttcttgaag atcgtgtcct tcaatgtctc tccatacccc tacaaagaaa aatattagat     1440
atagagaaag aaattgggct tccgatcgcc gagaactctt gcgattggca actaatctac     1500
ggcctggatt gccaatccta tatgagtgac tttcagccag atcttaggtt tcgatttct     1560 ttgggtttta ctgccctgtg gcatcgtctt gaaggcaacc taccgttgca cgcaagtcca     1620
tttcgaattc aaaagttaca aagtggtcac aagaaatgtt cgccccctgcc accttttagtt    1680 aacgaaaacc attggcagat gctggaatct ttggtgaagt ctaaaggtag cttgggcacc     1740
gttttactga gcgccatggc catccgttcg ttcaactggc caattgtatt gatccttggt     1800
gggctcgtcg gatcctttta catctacgag tacgccgctt ggacaactgc cgcccaagag     1860
cgaagtttca agagccagta cgccaggctc ttgcaacaac gtctgcggtc ggatgtgcag     1920
```

| | |
|---|---:|
| caaactgtta gcggttttga gctccagttg cgacagcacc tggcaacggt ccgaaattgc | 1980 |
| tgggaagccc agtccaatga cactgaat gacctgaacg taaggaccgc ggagctgacc | 2040 |
| aaacaaatac aatcgatgga ggtgttgcag ctcagcctga agaagtttcg ggacaaggga | 2100 |
| cagctgctgg ccagtcggtt gggagacttt caagagacct acttgaccaa gagctga | 2157 |

<210> SEQ ID NO 244
<211> LENGTH: 1389
<212> TYPE: DNA
<213> ORGANISM: Drosophila melanogaster

<400> SEQUENCE: 244

| | |
|---|---:|
| atgagggaga ttgtcacact gcagatcggc ggagccggaa atgccatcgg agattctttc | 60 |
| tggcacgtga tttcacatga acacggtgtg gattatgctt ctggtcgatt tggcggcacc | 120 |
| agtccacttc agctggagcg gatcaatgtg ttctttaacg caacggccag caaacggttc | 180 |
| tatgcccgca ccatactgat agacacggaa gccagcacca ttcagcgtct caacgccagc | 240 |
| agtcagctgt ataggccgga gaactttgtg gctggatcgg agagtgctgg gaacaacttt | 300 |
| gcacgtggct atcatacgga tggtgccgcc attctagatc aggtgctaga aaatacgcgc | 360 |
| cgggaggtcg aatcggtgga ttcgttgcag ggctttcagt tgctccactc tatcggaggc | 420 |
| ggaactggct ccggcttgac ctctctaata atggaggccc tggtggagca gtatccggat | 480 |
| aatttactct gcaactatgt gaccattccg tcgccgaata tgtcgcaggt ggttgtggaa | 540 |
| ccctataatg ccctacttag tactcccgcc ttggttaaca attcgcattt aaccttctgc | 600 |
| cttgataacg aggcactgtt ccaaatctgc aatagaaacc tgaagctcaa gatgtccggc | 660 |
| tacgagcaca ttaaccacat agtagccctg accatgtcgg gtataaccac ttgcctgcgg | 720 |
| tttcctggcc aactgaatgc tggattgcgc aagatctatg taaatatggt gccattcccg | 780 |
| cggctgcact tcctcatacc gggattcgca ccattggtca cttgcaagca gcagcagttc | 840 |
| agcaagggta ccgtttcgga gctggtgcag cagatcttct acagtaataa tctgctctgt | 900 |
| gccatcgatc ttcgaaaggg caaactgctg accgctgctg gaattttccg aggaagaatg | 960 |
| tcaccgcgtg aggtggatca actgatgact ggggtgagaa ataagaatat caacaatttc | 1020 |
| gtggactgga tacccaacaa tatcaagacg gctatttgcg atataccgcc gagggggcctc | 1080 |
| aagatgtcag ctacattcat tggcaacaca acggcgattc agacgctgtt ccagcgatta | 1140 |
| ctggacgctt ccatgtccat gttgcggcgc aaggcccatc ttcactggta cacgggagag | 1200 |
| ggaatggagg aacaggagtt ccaggatgcg cagcaggagt tacaagccat catcgatgat | 1260 |
| taccgcagta gtgctgaggg cgaggattcc ggtggtggcg gtggaggagg cggtggccga | 1320 |
| agtggaagcg ccgaaagcgg tgaagaggag gccacgcccg aagcccattg tcaatattgc | 1380 |
| accgaataa | 1389 |

<210> SEQ ID NO 245
<211> LENGTH: 738
<212> TYPE: DNA
<213> ORGANISM: Drosophila melanogaster

<400> SEQUENCE: 245

| | |
|---|---:|
| atgtcaatta tttcccttga agttcctatt cagccgtatg ctggtcagct gctcatcatc | 60 |
| aatgatctga ttctgccgga ctcaggctct caggatgcaa gcaaggcaaa agtctccata | 120 |
| aagaaaaatc aacgtgcatc cttctttgac cgcagcagta tctacaaaaa gataatgaag | 180 |
| cacttgtccc agggcaacca ggcggatgat atcaacattt ccgagcaaga atggctcctg | 240 |

```
gattctttt  tggccgcctt  ggagacctac  atgaaacatg  tggtcaagaa  gactatcgaa     300
ttgtgcgagc  atcgaacaag  ctatcatctg  cacaacgacg  aacgttgtgt  gatgaagaac     360
gatatgaggg  tcacgatgat  gttcctcaac  gatctcgaga  ttgccgacta  tggatcatcg     420
gatgacgaga  ccggctttta  tcgcaagcgc  cgggcagaga  acatcgacga  ggagagaaag     480
gtggctcgtc  tggaatcggt  gaatgatacg  gccttgctag  ccatctccgg  tcgaaagcgc     540
ccgggagaac  aactagcccc  agaatctgct  ccaagtggtt  cgaaagtcgc  caaattgacc     600
ggtgctccga  tccagcgagc  atgtgctccg  cgatttaagc  atatgaacat  cagggatgta     660
ctgcagttta  tggaggagga  cagacgatac  gcccggtcca  acatgctctt  cgaagcatat     720
ttaaaataca  agtcataa                                                      738

<210> SEQ ID NO 246
<211> LENGTH: 1650
<212> TYPE: DNA
<213> ORGANISM: Drosophila melanogaster

<400> SEQUENCE: 246
atggcatcca  cacgcatgat  cagtgctttt  acgcgcaatc  caagattata  tcaacaggtc      60
acggcaccct  ggaaatcgta  caatctgttt  ggaacaccac  tttttaacca  cagacttcag     120
ccagcggatt  ctcaaatctg  gaggggatta  gcagacaagt  gtgacaacaa  gactgttatc     180
aagggcgtgg  tggtgggcgt  ctactccaag  gagggcgacg  gtaaggaggt  caagatgacg     240
tccagcggcg  agaagttcga  cgaccgaact  cagggcaagg  tctcggagct  gttgcgcgaa     300
actggaatca  aggggggaact  gggcaagggt  aaggtcttca  tgaacgtgga  tgccgaattc     360
cgggcagtgg  ctgtggtggg  tttgggccaa  gaaggtgccg  gcttcaatga  cctggagaat     420
atcgacgagg  gtatggagaa  tgcccgcgtt  gccgctggcg  tcggagctcg  ggcattgcaa     480
ctgcagggtt  gcacggaagt  ctttgtggac  tccatggaat  atccggagca  ggcggcggag     540
ggcagtgctc  tggccatctg  gcgttacaat  agcaacaagc  gcaagcagga  tcgcactcag     600
gtacccaaac  tggatctgta  cgactcaccg  gatgtggatg  cctggacgag  gggtctcttc     660
aaggcggaat  ctcagaactt  ggctcgaaga  ttgagcgatt  cgccggctaa  tcagatgacc     720
cccaccatat  tcgcccaatc  ggcggtggat  gccctgtgtc  cgtgcggcgt  tccgtggag      780 gtgcgatcca  tggattggat  agaaatgaat  catctcaatt  cgtttctaat  gatagccaaa     840
ggcagctgcg  agccaccggt  ggtcctggag  gtcagctact  gcggcacagc  acccgaggat     900
cggcccattc  tgctgttggg  caagggtttg  acctacaaca  gtggcggatt  gtgcctgcgg     960
ccaaaggatt  gcctgcatat  gtaccgcggc  tgcatggcgg  gagcagccgt  ttgtgtggcc    1020
gccgttcgag  ctgcggcagc  cctttccctg  cctgtaaaca  tcacggccgt  actgccgctc    1080
tgcgagaata  tgccatcggg  aatggctgta  agccgggtg  atgtggtcac  cctgctcaat    1140
ggcaagacga  tgggtattgt  ggatgtgagc  aaagctggaa  cggtggtatt  ggctgatccc    1200
ctgctctttg  cccagacgac  gtacaagcct  cgtctggtgg  tggacttggc  caccgttggc    1260
tatggcgtct  gtgctggcct  tggagaatcg  gctgccggat  tgtttaccaa  ttccaatttc    1320
atagccaagc  agttcgagaa  ggctggcggc  ctgactggag  atcgtttatg  gaggctgccc    1380
ttgtggcgct  acttcaagca  gctggtaacc  cgaatctca  ccttcgacat  cagcaatagg    1440
ggcattggtc  ccgcctccag  ttgcattgct  gccgccgtgc  tgcacgaact  ggttccatgc    1500
gcggattggg  cccacattga  tatccggaat  gtgggcatgc  tgacacgcca  caatccgctg    1560
```

```
ccgtatctgc tcaaggatcg gatgaccggc cgacccaccc gcaccatcgt acagttcctg    1620
tatcagatgg cctgtccgga aagcaagtag                                    1650

<210> SEQ ID NO 247
<211> LENGTH: 1653
<212> TYPE: DNA
<213> ORGANISM: Drosophila melanogaster

<400> SEQUENCE: 247
atggaggaaa tcaagaagtt tgacaagctt gccttcctgg aaagctacct gctgaagcac     60
aaggaattgg caagcgaca cgcgagtac aagaagatcc tgtccagcaa actcaagacc     120
cgcaaggaga ccatcatcga ggccagcttt gagacggcca tcgatcagct ggaggaggag    180
aaaaacgatc tgcgtgccca gatctgggtg ccagtggta cgaccacaa aaaacagaac    240 aatcgctggc tggagctgat tcgctgccat gtcgagtgcc aggagaatct gtcgcaggac    300
attaactctc tgaagacatc gatttccaac atggagaagg ataagtcg catgtccaag     360 caaatataca acctgaatcg tttaaccatt ccggatcagc aacatcaggc ctatgtaatg    420
cgagcacgga aaaggatgac cattttggag aattccctgg aggtgggagt gcgtcaggag    480
tgcggtttta cggcagccaa tgcggatctg cgagagcagc ttatccgcat cctgaatcat    540
cgcaccttct tcaatgattc atacaccaaa atggtgcaga agctgaacag cgagaaaaag    600
tatctcatag atctgatcga atcgctctg aataccttcg atggctgcat tgaggtgtac    660
gagaaaattg atttgttggc caaaagggag gccaaggagc gcgatatgag acgtgtggag    720
atgcagggta ttatgcgaaa ggtggcagcc gatggtgata cacccgcctt cctgaattgc    780
aagtctaagc ctcgagagct ggccgatttg cagcccaagg agtacaagcg aagggatgaa    840
ttccgacggg tgcacaacaa aaagatcaat ctctacaact cggtgctgca gaagattctc    900
cagtatacgg aatctagcaa tatggacgag gtgatcgata agtttcagca gcaggagagt    960
ctctattact cgttcttcaa ctatgccaac gaaatgagct accacataac tatgctgaat    1020
aattcggtga atcgcctgtt tgaggatata gttaacctga aaaaggataa ctccaacacg    1080
ctgcaggacc aactggatca gatttccagt ctggagaaca aggtgcgtaa caaacaggaa    1140
tccaacatgg aactgcacaa ggcgcgggaa acaacgatg cacgtttgga gaatcttcta    1200
cagggcgtgg agacggtctg cgagatgtgt tccatagatg ccagtccgct gaccaaactc    1260
cttggtgacc acacccacgt caatctggtt aatgtcaatc gattcttgaa gctgctcgag    1320
acaagggtcc aggagctgac ggctagtgtt tatgtgatgg agcgccaaga ggagggccgc    1380
ttcgactatg tggtcaagca gatcgagaag atctgcgagc tgcccaccga tctcaatgac    1440
attgtgctca cccagcagtg tcccgagtgc gccgagggtg aagccttcaa catggatgag    1500
ggcggcgatg gtgtccttgt ccacacggtc gccgaggcca agaagaagct gtacgagaag    1560
gttacgcagc cggagatgca gtaccgcctg cacagcatca gccagtgtcg tctgccgcga    1620
tcccgtctcc tggccgccaa gcgcaacatg tag                                1653

<210> SEQ ID NO 248
<211> LENGTH: 2220
<212> TYPE: DNA
<213> ORGANISM: Drosophila melanogaster

<400> SEQUENCE: 248
atggccacaa aaccgggaaa aggtgacggc aagcaggtga agggaaaaag gacctccaag     60
aacaagacag atggccccgg cggtggtggc ggcgatgccg atgacttcga tgcctggatg    120
```

```
aagtcgcgcc agctgctcaa gcccgatgac cagctcgatc tcaccgaggc ggaactgggc      180
gaggagatca ccaaggtgct gactcccacc aacacgaaca tcgttcgcaa tctcgtggtc      240
tatagcttca aggaaggcga gtttgttccg gctccgttgc ccggcaatac ggtcaccta       300 atcgcctttg ccggcaactc acttcacgtg gactccgatg agggtcgccg tcagatcgag      360
gagtccgacg agattggcta cccactgccc atgcccaact acactgtggt ggagcagcgc      420
gagacggata acgtcgacgg tgaggaggga gagggcgagg aggatgatga tggggccacc      480
gcaaaggacg ccgccgtaga agacgaggat gtcgaggagg aggacgacga ggaggccaag      540
ggcaccgaag gcgatgaggg cgagggcgaa ggcgagggag agggtgctgc tgcccgccag      600
gaggacgatg agcccgccca ccaagcggcg gccgtttcat ccaagaaacg caagctaatc      660
aaccagttca actactgcga acgtggtgcc ctcacctaca caaatcccaa aggaatgta       720 gacacccaga ccataccccc accccgttcc cagtttggag ccaatgtgct gcagtgggtc      780
atctatgatt cctatatgga aactttgcg gagtcccaga aggacggcac caagaaggag       840
gagcgcaagc gcggcaagag ggagaagaag ttccgggata agtcggccat tgccgagcag      900
ctcaacaaga agtatctcaa atgctggcag atactcgagc gcatgatcaa tcagaatatc      960
tacgatgaca tcgcccacga ctatcgctac tgggaggatc cggctgatga gtttcgtgag     1020
ggtgagggca acctgctgcc actctggaag tttcagtacg acaagaccaa gaagatgaac     1080
gtcaccgaca tcctgttcaa tccgagctac tatgatctct tcgccgtctg tttcggatcg     1140
catgacttca tgaagcagac caatgagggt tacttgtgtc tgttcaccgt taagaatccc     1200
tcattcccgg actatataat tcaaaccgac tgtggtgtca tgtgctgtga catccaccca     1260
acgtatcctt tcctggccgt aatcggtctc tatgacggca atgtggcggt ctacaatctg     1320
cgcgaggact gcaaggaacc actctatgtg tccagaggag tcaactgcaa gcacggcgag     1380
tgcgtgtggc agatcaagtg gggtttggac atggccgatg gcgaggtgaa cttcttttcg     1440
gtgtcctccg atgggcgcgt cttcaactgg attctcatgc agaacaaact gtgggtaacc     1500
accatcatca cattgtaccg cgaaaacgga ctggttgacg gaccagatgg cacaaaggtc     1560
acgctgaaga gcggaggatc ctgcatggtg ttccatccag tggataataa gatatttctg     1620
gtgggcaccg agtgtggtta catctacaag tgcagcacgg cgttcagctc caaatacctg     1680
atgacctact atgcccacaa catgtccgtc tatcgcattg acttcaatcg cttcaacagc     1740
aacatcttcg tgtcctgtgg cgccgactgg atggtcaagg tgtgggagga tatgcgtcca     1800
gatccgctgt tcatattcga tcttggtgcc gccgttggcg atgtcaagtg ggcaccttac     1860
tcgagcaccg tcttcgcagc ggtgaccacc gagggcaagg tccacgtttt cgacctaaat     1920
gtgaataagt acaaggccat ctgcatccag gccgtggtgc ccaagcgaaa gaacaagctc     1980
accaggttat ccttcaacga gaagctcgcc ttcattgtgg tgggcgatga aagggcgtc      2040 accacttcgc tgaagctatc gcccaatctc cggatgatgg tgaagccgcc gaagaagcag     2100
ctgtatctcg accagaacac cctccagatt ggcaagttgg agaagctgct ttccctggtg     2160
cgggaacttc cggaaggttc aactgcggtg cccgatgcag ccacaaccgt gcgaagttaa     2220
```

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 249
ctttcagctc tccgatgtgc v                                                    21

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
tatcctgggc agctgaactc v                                                    21
```

UNITED STATES PATENT AND TRADEMARK OFFICE
CERTIFICATE OF CORRECTION

PATENT NO. : 10,039,287 B2
APPLICATION NO. : 15/022759
DATED : August 7, 2018
INVENTOR(S) : Steve Whyard Page 1 of 1

It is certified that error appears in the above-identified patent and that said Letters Patent is hereby corrected as shown below:

In the Claims

Column 148, Line No. 37, Claim 12, --method of claim 7-- should read --The method of claim 7--.

Signed and Sealed this
Twenty-fifth Day of June, 2019

Andrei Iancu
*Director of the United States Patent and Trademark Office*